US012751939B2

(12) United States Patent
Htoo et al.

(10) Patent No.: US 12,751,939 B2
(45) **Date of Patent: *Oct. 6, 2026**

(54) TOPICAL OCULAR DELIVERY OF CROMAKALIM

(71) Applicants: QLARIS BIO, INC., Dedham, MA (US); MAYO FOUNDATION FOR MEDICAL EDUCATION AND RESEARCH, Rochester, MN (US)

(72) Inventors: Thurein M. Htoo, Westwood, MA (US); Michael P. Fautsch, Rochester, MN (US); Gary Allred, Wake Forest, NC (US); Ralph Casale, Westford, MA (US); Barbara M. Wirostko, Park City, UT (US)

(73) Assignees: QLARIS BIO, INC., Dedham, MA (US); MAYO FOUNDTATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/313,605

(22) Filed: Aug. 28, 2025

(65) Prior Publication Data

US 2025/0387366 A1 Dec. 25, 2025

Related U.S. Application Data

(63) Continuation of application No. 18/907,300, filed on Oct. 4, 2024, which is a continuation of application No. PCT/US2023/078754, filed on Nov. 3, 2023.

(60) Provisional application No. 63/523,616, filed on Jun. 27, 2023, provisional application No. 63/424,434, filed on Nov. 10, 2022, provisional application No. 63/422,805, filed on Nov. 4, 2022.

(51) Int. Cl.

| | |
|---|---|
| ***A61K 31/4025*** | (2006.01) |
| ***A61K 9/00*** | (2006.01) |
| ***A61K 47/10*** | (2017.01) |
| ***A61K 47/14*** | (2017.01) |
| ***A61K 47/26*** | (2006.01) |
| ***A61K 47/32*** | (2006.01) |
| ***A61K 47/44*** | (2017.01) |
| ***A61P 27/06*** | (2006.01) |

(52) U.S. Cl.

CPC ........ *A61K 31/4025* (2013.01); *A61K 9/0048* (2013.01); *A61K 47/10* (2013.01); *A61K 47/14* (2013.01); *A61K 47/26* (2013.01); *A61K 47/32* (2013.01); *A61K 47/44* (2013.01); *A61P 27/06* (2018.01)

(58) Field of Classification Search

CPC .. A61K 9/0048; A61K 31/4025; A61K 47/10; A61K 47/26; A61K 47/32; A61K 47/44

See application file for complete search history.

(56) References Cited

U.S. PATENT DOCUMENTS

| | | | |
|---|---|---|---|
| 2,986,573 | A | 5/1961 | Topliss et al. |
| 3,361,816 | A | 1/1968 | Topliss et al. |
| 4,200,640 | A | 4/1980 | Nagano et al. |
| 4,409,222 | A | 10/1983 | Arrigoni-Martelli |
| 5,013,853 | A | 5/1991 | Gericke et al. |
| 5,965,620 | A | 10/1999 | Sorgente et al. |
| 5,985,856 | A | 11/1999 | Stella et al. |
| 7,186,707 | B2 | 3/2007 | Prokai et al. |
| 8,063,054 | B2 | 11/2011 | Lazdunski et al. |
| 8,980,839 | B2 | 3/2015 | Mitra et al. |
| 9,937,225 | B2 | 4/2018 | Mitra et al. |
| 10,441,630 | B2 | 10/2019 | Mitra et al. |
| 10,918,694 | B2 | 2/2021 | Weiss et al. |
| 2005/0244339 | A1 | 11/2005 | Jauernig et al. |
| 2013/0023550 | A1 | 1/2013 | Gupta et al. |
| 2014/0206626 | A1 | 7/2014 | Acheampong et al. |

(Continued)

FOREIGN PATENT DOCUMENTS

| | | | |
|---|---|---|---|
| EP | 120428 | A1 | 10/1984 |
| WO | WO-1989/10757 | A1 | 11/1989 |

(Continued)

OTHER PUBLICATIONS

Ashwood et al., "Synthesis and Antihypertensive Activity of 4-(Cyclic Amido)-2H-1-benzopyrans" *J. Med. Chem.* 29, 2194, 1986.

Attwood et al., "Synthesis of Homochiral Potassium Channel Openers: Role of the Benzopyranyl 3-Hydroxyl Group in Cromakalim and Pyridine N-Oxides in Determining the Biological Activities of Enantiomers" *Bioorg. Med. Chem. Lett.* 2, 229, 1992.

Brayden, J.E. et al., "Role of potassium channels in the vascular response to endogenous and pharmacological vasodilators" *Journal of Vascular Research* 28.1-3 147-153, 1991.

Călugăru, D., "Etiology, pathogenesis, and diagnosis of neovascular glaucoma" *Int J Ophthalmol.*, 15(6), 1005-1010, Jun. 18, 2022.

(Continued)

*Primary Examiner* — Clinton A Brooks

*Assistant Examiner* — Josmalen M. Ramos-Lewis

(74) *Attorney, Agent, or Firm* — Knowles Intellectual Property Strategies, LLC

(57) ABSTRACT

Aqueous ocular topical pharmaceutical formulations are provided that deliver an effective amount of (lev)cromakalim or a pharmaceutically acceptable salt thereof to treat an anterior or a posterior ocular disorder that responds to (lev)cromakalim, including glaucoma.

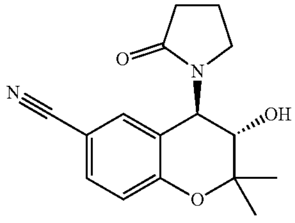

levcromakalim

29 Claims, 6 Drawing Sheets

(56) References Cited

U.S. PATENT DOCUMENTS

Figure 1:
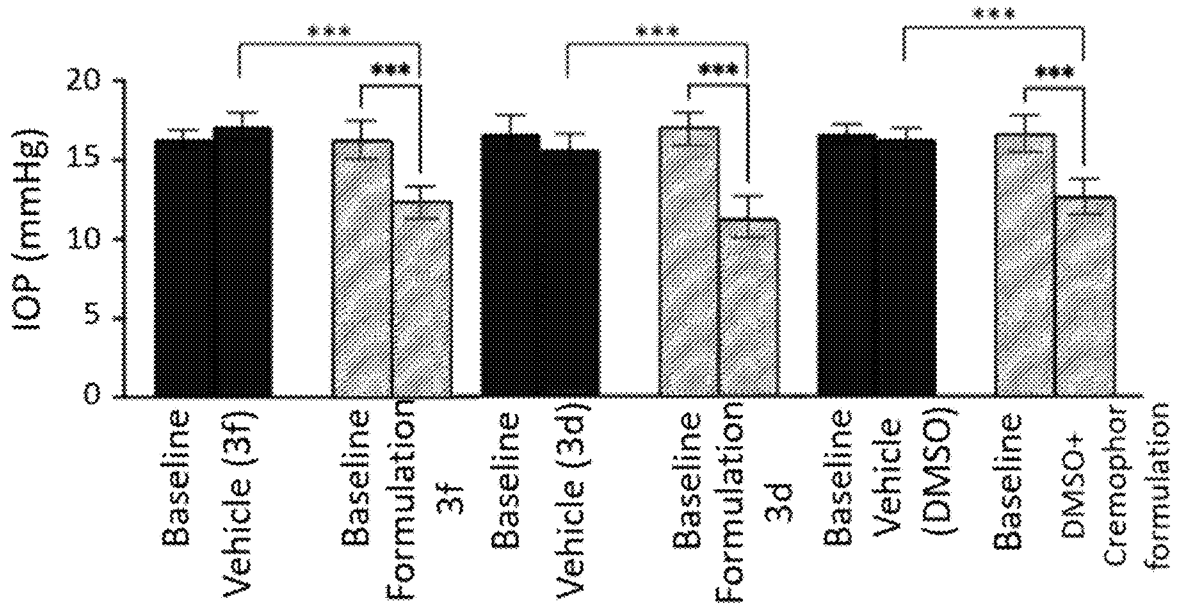

| | | | |
|---|---|---|---|
| 2019/0060397 A1 | 2/2019 | Weiss et al. | |
| 2019/0224120 A1 | 7/2019 | Horn | |
| 2020/0306218 A1 | 10/2020 | Valdivia | |
| 2021/0299046 A1 | 9/2021 | Chang et al. | |

FOREIGN PATENT DOCUMENTS

| | | | | |
|---|---|---|---|---|
| WO | WO-2008/027341 A2 | 3/2008 | | |
| WO | WO-2009/120656 A1 | 10/2009 | | |
| WO | WO-2015/117024 A1 | 8/2015 | | |
| WO | WO-2020/139525 A1 | 7/2020 | | |
| WO | WO-2021/119503 A1 | 6/2021 | | |
| WO | WO-2021158992 A1 * | 8/2021 | | A61P 9/12 |
| WO | WO-2021213512 A1 * | 10/2021 | | A61K 9/10 |
| WO | WO-2021/262916 A1 | 12/2021 | | |
| WO | WO-2022/207773 A1 | 10/2022 | | |
| WO | WO-2023/018958 A1 | 2/2023 | | |

OTHER PUBLICATIONS

Cequa Prescribing information, Available from https://cequapro.com/CeguaPI.pdf, revised Jul. 2022.

Chiang and Lin, "Effects of Cromakalim and Nicorandil on Intraocular Pressure After Topical Administration in Rabbit Eyes" *J. Ocular Pharmacology*; vol. 11(3), 195-202, 1995.

Chowdhury et al., "ATP-Sensitive Potassium (KATP) Channel Activation Decreases Intraocular Pressure in the Anterior Chamber of the Eye" *IOVS.*, 52(9):6435-6442, Aug. 2011.

Chowdhury, et al., "ATP-Sensitive Potassium (KATP) Channel Openers Diazoxide and Nicorandil Lower Intraocular Pressure in Vivo" *Investigative Ophthalmology and Visual Science*, 54, 7, 4892-4899, Jul. 2013.

Chowdhury et al., "Ocular Hypotensive Effects of the ATP-Sensitive Potassium Channel Opener Cromakalim in Human and Murine Experimental Model Systems" *PLOS One*, 10, e0141783, 2015.

Chowdhury et al., "Analogs of the ATP-Sensitive Potassium (KATP) Channel Opener Cromakalim with in Vivo Ocular Hypotensive Activity" *J. Med. Chem.* 59, 6221, 2016.

Chowdhury et al., "Effect of Cromakalim Prodrug 1 (CKLP1) on Aqueous Humor Dynamics and Feasibility of Combination Therapy with Existing Ocular Hypotensive Agents" *IOVS*, 58, 5731-5742, 2017.

Chowdhury et al., "Pharmacological and Pharmacokinetic Profile of the Novel Ocular Hypotensive Prodrug CKLP1 in Dutch-belted Pigmented Rabbits" *PLoS One*, 15, e0231841, 2020.

Chowdhury, U. R. et al., "Preclinical Pharmacokinetic Profile of Topical Ophthalmic and Intravenous Delivery of QLS-101, a Novel ATP-Sensitive Potassium Channel Opening Ocular Hypotensive Agent" *Journal of Ocular Pharmacology and Therapeutics*, 39, 5, 322-346, May 17, 2023.

Fautsch et al., "Effect of ATP-Sensitive Potassium (KATP) Channel Openers on Intraocular Pressure (IOP) and Aqueous Humor Dynamics in Preclinical Ocular Hypertensive Models" *Ocular hypertension*, ISER, 1 page, Oct. 2021.

Fautsch et al., "Effect of ATP-sensitive potassium channel openers on intraocular pressure in ocular hypertensive animal models" Pharmacology abstract—*TM Society*, Dec. 11, 2021.

Hamilton et al., "Levcromakalim" *Cardiovascular Drug Reviews*, vol. 11, No. 2 pp. 199-222, 1993.

Kaplan et al., "Emerging drugs for the treatment of glaucoma: a review of phase II & III trials" *Expert Opinion on Emerging Drugs*, 27:3, 321-331, Aug. 12, 2022.

Mandal et al., "Polymeric micelles for ocular drug delivery: From structural frameworks to recent preclinical studies" *Journal of Controlled Release* 248: 96-116, 2017.

NCT04830397—Study to Evaluate QLS-101 Compared to Timolol Maleate Eye Drops in Subjects With High Eye Pressure (Glaucoma or Ocular Hypertension), ClinicalTrials.gov, first posted Apr. 1, 2021, last update posted Jan. 17, 2025.

NCT04857827—A Study to Evaluate Safety and Tolerability of QLS-101 in NTG, ClinicalTrials.gov, first posted Apr. 22, 2021, last update posted Jan. 20, 2025.

NCT04947124—A Study to Determine the Safety and Tolerability of 2 Concentrations of QLS-101, ClinicalTrials.gov, first posted Jun. 23, 2021, last update posted Jan. 20, 2025.

NCT05495269—Safety and Tolerability Study of QLS-101 in Adolescents With Sturge- Weber Syndrome (SWS)-Related Glaucoma Due to Elevated Episcleral Venous Pressure (EVP), ClinicalTrials.gov, first posted Aug. 8, 2022, last update posted Jan. 20, 2025.

NCT06016972 (Osprey)—Qlaris Phase 2 Study of QLS-111 in POAG And/or OHT Patients, ClinicalTrials.gov, first posted Aug. 29, 2023, last update posted Jan. 20, 2025.

NCT06030193—Qlaris Phase 2 Study in NTG Patients, ClinicalTrials.gov, first posted Sep. 6, 2023, last update posted Jan. 17, 2025.

NCT06249152 (Apteryx)—Qlaris Study of QLS-111 in Combination With a PGA for OAG and/or OHT Patients, ClinicalTrials.gov, first posted Jan. 31, 2024, last update posted Jan. 20, 2025.

Noma, A., "ATP-regulated $K^+$ channels in cardiac muscle" *Nature*, 305, 147-148, 1983.

Patel, A. et al., "Ocular drug delivery systems: An overview" *World J. Pharmacol.* vol. 2, Issue 2, pp. 47-64. Available from: https://www.ncbi.nlm.nih.gov/pmc/articles/PMC4289909/pdf/nihms641436.pdf, 2013, Accessed Jul. 6, 2018.

Popov, "Mucus-Penetrating Particles and the Role of Ocular Mucus as a Barrier to Micro- and Nanosuspensions" *J. Ocul Pharmacol Ther*, 36(6): 366-375, 2020.

Qlaris Bio, Inc., "Qlaris Bio Enrolls First Patient in Phase 1/2 Studies of QLS-101" Press release, Apr. 15, 2021, accessed Mar. 12, 2025.

Qlaris Bio, Inc., "Qlaris Bio Reports Phase 2 Clinical Trial Results Demonstrating Favorable Safety and Tolerability Profile and Positive Efficacy Signal for QLS-101" Press release, May 18, 2022, accessed Mar. 12, 2025.

Qlaris Bio, Inc., "Qlaris Bio Named 2022 Scrip Awards Finalist for Biotech Company of the Year" Press release, Oct. 4, 2022, accessed Mar. 12, 2025.

Qlaris Bio, Inc., "Qlaris Bio's Novel IOP-Lowering Product, QLS-111, Is Dosed In Phase II Trials" Press release, Apr. 2, 2024, accessed Mar. 12, 2025.

Qlaris Bio, Inc., "Qlaris Bio Completes $24 Million Series B Financing Round to Advance QLS-111, a First-in-class IOP-lowering Drug Candidate for Glaucoma" Press release, Apr. 30, 2024, accessed Mar. 12, 2025.

Qlaris Bio, Inc., "Qlaris Bio Announces Positive Topline Data From Two Phase II Trials Of QLS-111 In Patients With Primary Open Angle Glaucoma And Ocular Hypertension" Press release, Feb. 5, 2025, accessed Mar. 12, 2025.

Quast, U. et al., "In vitro and in vivo comparison of two K + channel openers, diazoxide and cromkalim, and their inhibition by glibenclamide" *Journal of Pharmacology and Experimental Therapeutics*, 250, 261, 1989.

Singh and Verma, "Preparation and characterization of nanomicelle for ocular delivery of fluoroquinolone derivative" *Journal of Drug Delivery and Therapeutics* 9.2-s: 355-365, 2019.

Steel, C. L., "Preclinical Efficacy and Safety Profile of QLS-101, a Novel ATP-Sensitive Potassium Channel Opener for the Reduction of IOP" *AOPT Talk*, Qlaris Bio, Inc., Feb. 24, 2021.

Steel, C. L. et al., "Preclinical Efficacy and Safety Profile of a Novel Episcleral Venous Pressure (EVP)-Lowering Agent" *American Glaucoma Society*—Poster, 1 page, Feb. 28, 2021.

Steel, C. L. et al., "Ocular Tissue Conversion and Activity Profile of QLS-101, a Novel Topical IOP-Lowering Therapeutic" *Association for Research in Vision and Ophthalmology* (*ARVO*), Qlaris Bio, Inc. Poster, 1 page, Apr. 28, 2021.

Steel, C. L. et al., "Ocular Hypotensive Properties and Biochemical Profile of QLS-101, a Novel ATP-Sensitive Potassium ($K_{ATP}$) Channel Opening Prodrug" *iovs*, 63, 26, Apr. 29, 2022.

Trinh et al., "Clear, aqueous topical drop of triamcinolone acetonide" *AAPS PharmSciTech* 18: 2466-2478, Feb. 9, 2017.

Vadlamudi and Dhanaraj, "Significance of excipients to enhance the bioavailability of poorly water-soluble drugs in oral solid dosage

(56) References Cited

OTHER PUBLICATIONS forms: A Review" *IOP Conference Series: Materials Science and Engineering*. vol. 263. No. 2. IOP Publishing, 2017.
Vyzulta Prescribing information revised May 2019, available from https://www.bausch.com/globalassets/pdf/packageinserts/pharma/vyzulta-prescribing-information.pdf.
WebPage: Unique NCELL® Technology and formulation provide superior delivery over cyclosporine emulsion 0.05% https://cequapro.com/ncell-technology, Accessed: Sep. 27, 2022.
Whidden, M. A. et al., "Altered potassium ATP channel signaling in mesenteric arteries of old high salt-fed rats" *J Exerc Nutri Biochem*. 20(2), 58-64, 2016.
Wirostko, B. M. et al., "Systemic and Ocular Toxicology and Pharmacokinetic Profiles of QLS-101, a Novel topical IOP-Lowering Therapeutic" *Association for Research in Vision and Ophthalmology*, Qlaris Poster—In vivo preclinical data, 1 page, Apr. 28, 2021.
U.S. Pat. No. 10,981,951, B2, U.S. Appl. No. 15/113,773, Fautsch et al., Apr. 20, 2021.
U.S. Pat. No. 11,505,572, B2, U.S. Appl. No. 17/077,859, Fautsch et al., Nov. 22, 2022.
U.S. Pat. No. 12,209,140, B2, U.S. Appl. No. 17/991,558, Fautsch et al., Jan. 28, 2025.
US, 2022/0324890, A1, U.S. Appl. No. 17/836,871, Htoo et al., Oct. 13, 2022.
US, 2022/0387457, A1, U.S. Appl. No. 17/882,270, Htoo et al., Dec. 8, 2022.
US, 2023/0381343, A1, U.S. Appl. No. 18/343,437, Fautsch et al, Nov. 30, 2023.
US, 2024/0285580, A1, U.S. Appl. No. 18/439,552, Htoo et al., Aug. 29, 2024.
US, 2025/0108035, A1, U.S. Appl. No. 18/907,296, Htoo et al., Apr. 3, 2025.
US, 2025/0108002, A1, U.S. Appl. No. 18/907,300, Htoo et al., Apr. 3, 2025.
U.S. Pat. No. 12,454,539-B2, Oct. 28, 2025, Htoo et al., U.S. Appl. No. 17/836,871.

* cited by examiner

TOPICAL OCULAR DELIVERY OF CROMAKALIM

CROSS-REFERENCE TO RELATED APPLICATIONS

This application is a continuation of U.S. patent application Ser. No. 18/907,300, filed Oct. 4, 2024, which is a continuation of International Patent Application No. PCT/US2023/078754, filed in the U.S. Receiving Office on Nov. 3, 2023, which claims the benefit of priority to U.S. Ser. No. 63/422,805, filed Nov. 4, 2022; U.S. Ser. No. 63/424,434, filed on Nov. 10, 2022; and U.S. Ser. No. 63/523,616, filed on Jun. 27, 2023. The entirety of each of these applications is hereby incorporated by reference herein for all purposes.

STATEMENT REGARDING FEDERALLY SPONSORED RESEARCH

This invention was made with government support under Grant No. EY021727 awarded by the National Institutes of Health. The government has certain rights in the invention.

FIELD OF THE INVENTION

This application provides a pharmaceutical formulation for the topical ocular delivery of cromakalim, including levcromakalim, for therapeutic uses as further described herein, including to lower intraocular pressure, and to treat glaucoma generally, including normal tension glaucoma.

BACKGROUND OF THE INVENTION

Cromakalim and its use as an anti-hypertensive was first described in European Patent EP 0120428B1 that claims priority to applications filed in 1983, issued in 1990 and assigned to the Beecham Group, Inc. Disclosures of cromakalim's effects on intraocular pressure and glaucoma were reported in PCT Application WO 89/10757; Lin et al., "Effects of Cromakalim and Nicorandil on Intraocular Pressure after Topical Administration in Rabbit Eyes" *Journal of Ocular Pharmacology and Therapeutics,* 1995, 11, 195; and Chowdhury et al., "Ocular Hypotensive Effects of the ATP-Sensitive Potassium Channel Opener Cromakalim in Human and Murine Experimental Model Systems" *PLOS One,* 2015, 10, e0141783.

Cromakalim was reported to lower blood pressure in Quast et al., "In vitro and in vivo comparison of two K+ channel openers, diazoxide and cromakalim, and their inhibition by glibenclamide" *J Pharmacol Exp Ther* 1989, 250, 261. Cromakalim placed in membrane patches from rabbit mesenteric arterial smooth muscle cells increases the open-state probability ($P_{open}$) of single $K_{ATP}$ channels more than 9-fold in the presence of ATP (Brayden, J. E. et al., *Blood Vessels,* 1991, 28, 147). Cromakalim exists as a mixture of stereoisomers in the trans-configuration (a mixture of (3R,4S) and (3S,4R) stereoisomers).

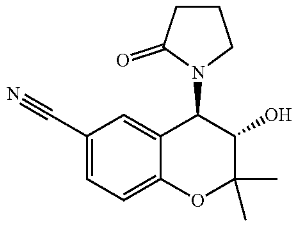

-continued

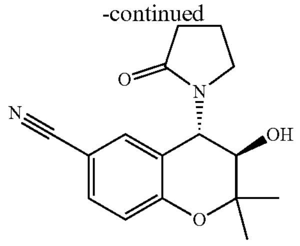

Cromakalim (mixture of trans-stereoisomers)

The (3S,4R)-stereoisomer is referred to as (−)-cromakalim or levcromakalim and the (3R,4S)-stereoisomer is referred to as (+)-cromakalim or dexcromakalim.

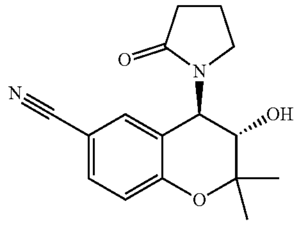

(-)-cromakalim
levcromakalim

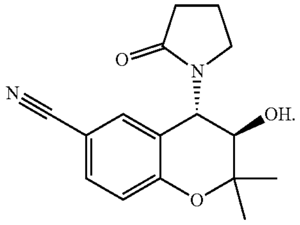

(+)-cromakalim
dexcromakalim

The majority of cromakalim's reported activity stems from the (3S,4R)-stereoisomer levcromakalim (Ashwood et al. Synthesis and Antihypertensive Activity of 4-(Cyclic Amido)-2H-1-benzopyrans" *J. Med. Chem.* 1986, 29, 2194 and Attwood et al. "Synthesis of Homochiral Potassium Channel Openers: Role of the Benzopyranyl 3-Hydroxyl Group in Cromakalim and Pyridine N-Oxides in Determining the Biological Activities of Enantiomers" *Bioorg. Med. Chem. Lett.* 1992, 2, 229).

Cromakalim is poorly soluble in water and aqueous buffer formulations and readily crystallizes or co-crystallizes and precipitates from solution. It is also poorly soluble in oil or non-polar hydrophobic solvents. Cromakalim is soluble in highly polar "universal" organic solvents such as DMSO (dimethyl sulfoxide), DMF (dimethyl formamide) or NMP (1-methylpyrrolidone) which are capable of hydrogen bonding interactions and hydrophobic interactions, however these are not preferred solvents for in vivo delivery of drugs. It is also somewhat soluble in alcohol such as ethanol, but these low molecular weight monoalcohols are unsuitable for topical human ocular administration.

Despite the strong biological activity of cromakalim, it has never been approved as a drug. Cromakalim has been tested in human clinical trials for systemic hypertension, but the program was terminated. Insolubility in water prevented levcromakalim from being considered for local administration for ophthalmic uses, such as via topical or intraocular routes.

Cromakalim has been solubilized with DMSO and cremophor, that is also used for the non-water-soluble anti-cancer drug taxol (Cremophor EL, now referred to as Kolliphor EL by BASF). However, cromakalim has exhibited low solubility even in DMSO co-solvent mixtures necessitating the use of high percentage of DMSO, as demonstrated in Whidden, M. A. et al. *J Exerc Nutri Biochem.* 2016, 20(2), 58-64 or in combination with Cremophor as demonstrated in Roy Chowdhury, U et al. *PLOS ONE.* 2015, 10 (11), e0141783.

Chiang and Lin researched the effect of cromakalim in rabbit eyes using three levels of ocular tension (Chiang and Lin, "Effects of Cromakalim and Nicorandil on Intraocular Pressure After Topical Administration in Rabbit Eyes", *J. Ocular Pharmacology;* 1995 Vol 11(3), 195-202. The laboratory cromakalim test solution was reported as 0.5% (assumed w/w) cromakalim in 0.02 M phosphate buffer. The authors reported that cromakalim tended to increase IOP after topical administration and that this could be contraindicated for patients with glaucoma. They did report that cromakalim reduced IOP in an α-chymotrypsin model after a delay that included an increase in IOP for the first few hours. That said, the Chiang Lin report must be discounted because it had already been reported that levcromakalim has a solubility limit in water of 0.48 mg/ml by SmithKline Beecham Pharmaceuticals in Harlow U.K. in 1993 (see Hamilton, et al, Levcromakalim, *Cardiovascular Drug Reviews*, Vol 11, No. 2 pp 199-222), which corresponds to 0.048% w/w, i.e., ten times lower than that used by Chiang and Lin at the National Defense Medical Center of Taiwan in 1995. Therefore, the Chiang Lin tested material undoubtedly had insoluble material which would have a deleterious effect on the eye and nullify the results. The Hamilton article also stated that cromakalim is soluble in ethanol, DMSO and PEG, none of which would be acceptable as the topical ocular carrier for human administration.

In response to the need to create a cromakalim formulation that has appropriate solubility for administration into aqueous environments in vivo, Mayo Foundation for Medical Education and Research and Reagents of the University of Minnesota created the phosphate ester prodrug CKLP1 (also referred to as QLS-101), also reported as a sodium salt.

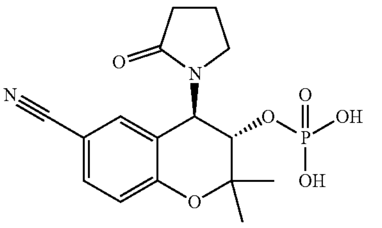

CKLP1

CKLP1 provides an improvement of increased water solubility for ease of administration in combination with hydrolysis in vivo to the parent levcromakalim. See WO 2015/117024 filed by Mayo Foundation for Medical Education and Research and the Regents of The University of Minnesota. See also WO2021/1119503 and WO 2021/158992 filed by Mayo Foundation for Medical Education and Research and Qlaris Bio, Inc. However, it is a prodrug that presents the typical range of prodrug issues of increased cost and complexity of manufacture and as well as complexity of metabolism.

Roy Chowdhury et al. "Analogs of the ATP-Sensitive Potassium (KATP) Channel Opener Cromakalim with in Vivo Ocular Hypotensive Activity" *J. Med. Chem.* 2016, 59, 6221, reported that the phosphate prodrug is more water soluble than cromakalim and was reported to lower intraocular pressure (IOP) in a normotensive (i.e., normal IOP) mouse model, however, the drug was only administered for 7 days. The article also reported the efficacy of increasing doses of certain cromakalim derivatives in rabbit eyes over an 8-day period.

The effect of CKLP1 on episcleral venous pressure and distal outflow resistance was described in Roy Chowdhury et al. "Effect of Cromakalim Prodrug 1 (CKLP1) on Aqueous Humor Dynamics and Feasibility of Combination Therapy with Existing Ocular Hypotensive Agents" *IOVS,* 2017, 58, 5731. Pharmacokinetic parameters in rabbits following topical and intravenous administration were described in Roy Chowdhury et al. "Pharmacological and Pharmacokinetic Profile of the Novel Ocular Hypotensive Prodrug CKLP1 in Dutch-belted Pigmented Rabbits" *PLoS One,* 2020, 15, e0231841). The synthesis of CKLP1 and the corresponding (3R,4S)-enantiomer is described in Roy Chowdhury et al. (*J. Med. Chem.* 2016, 59, 6221).

Qlaris Bio, Inc. reported the Phase 2 clinical trial results of QLS-101 demonstrating a favorable safety and tolerability profile and positive efficacy signal for the cromakalim prodrug. The clinical trial was conducted to investigate the ability to lower intraocular pressure in the treatment of glaucoma. The study demonstrated no evidence of hyperemia (eye redness) and a positive efficacy signal in patients with primary open-angle glaucoma.

It is a particularly difficult challenge to deliver a drug for ocular therapy through the ocular mucosal barrier. Along with other functions, the mucus barrier layer traps and eliminates foreign substances, such as allergens, pathogens, and debris, which means it can also trap drugs. One solution has been the use of mucus-penetrating particles such as nanoparticles with a particle size smaller than the mucus mesh size. See A. Popov; Mucus-Penetrating Particles and the Role of Ocular Mucus as a Barrier to Micro- and Nanosuspensions, *J. Ocul Pharmacol Ther*, July/August 2020; 36(6): 366-375.

Qlaris Bio and Mayo Foundation for Medical Education and Research have filed a patent application describing polymeric controlled release formulations of levcromakalim for medical uses, including ocular delivery. See PCT/US2022/040197.

In addition to these stated challenges, while solutions and suspensions remain the preferred dosage form for ocular drug delivery (when the drug is adequately soluble), only a small portion of the drug administered as a conventional eye drop reaches the anterior ocular tissues necessary to treat glaucoma (sometimes as little as 0.1-5% of the dispensed dose) due to poor corneal permeability, reflex blinking, tear secretion, dose spillage and nasolacrimal drainage.

Given the potential yet unrealized therapeutic benefits of cromakalim, it would be beneficial to provide new routes to unlock the activity of this drug to lower intraocular pressure and treat the variety of disorders affected by elevated IOP, or normotensive disorders such as normal tension glaucoma, or ocular disorders which otherwise respond to treatment with cromakalim.

SUMMARY OF THE INVENTION

It has been surprisingly discovered that the parent cromakalim drug, for example, levcromakalim (referred to together as (lev)cromakalim), or a pharmaceutically acceptable salt thereof, can be delivered topically and efficiently in drop form in an effective therapeutic amount to treat the anterior portion of the human eye without the use of a covalent prodrug approach, a polymeric delivery system or a high level of toxic components, and with at least 4 or 5 months of shelf life stability, through the use of specifically discovered combinations of excipient components. The topical formulation of the present invention can be used to treat an anterior or posterior ocular disorder that is responsive to cromakalim. For example, the cromakalim formulation described herein can be used to lower intraocular pressure, and to treat glaucoma generally, including normal tension glaucoma, open angle glaucoma, and closed angle glaucoma among other therapeutic uses as described further herein.

It is a significant advance that a stable topical pharmaceutically acceptable formulation of (lev)cromakalim for humans is finally provided, almost 40 years after the discovery of the drug.

The formulations of the present invention comprising levcromakalim are well-tolerated and can be used as efficacious topical intraocular pressure (IOP) lowering agents even in a generally healthy normotensive host such as a human. A study on Dutch Belted Rabbit (Example 11) demonstrates that the formulation of the present invention exhibits a benign toxicology profile with no notable adverse events up to its maximally formulatable concentration (5 mM). No significant ocular or systemic AEs such as hyperemia (eye redness) was observed in this study.

Human clinical data has established that the levcromakalim formulation of the present invention has a safe and tolerable profile with daily ophthalmic administration, and the formulation demonstrates IOP lowering in a facile fashion. In certain embodiments, IOP is lowered within several hours, for example 4 hours following the first topical administration at two different concentrations (0.5 mM and 5 mM) of (lev)cromakalim. Additionally, the formulation has an IOP lowering effect throughout the 14-day illustrative non-limiting treatment period (See Example 8 and Example 9). The formulation is also effective in a hypertensive host, as well as a normotensive host.

The formulations of the present invention comprising leveromakalim lower IOP by relaxing vessels of the vascular and vascular-like tissues distal to the trabecular meshwork (TM), thereby reducing the distal outflow resistance and lowering episcleral venous pressure (EVP). Current therapies target only three of the four components of IOP, namely the aqueous humor inflow rate, uveoscleral outflow rate, and conventional outflow facility. The (lev)cromakalim formulation of the present invention targets the fourth component, reduction of EVP. This fills the gap in the potential to maximally lower IOP as EVP can be the largest determinant of overall IOP, while maintaining normal vascular integrity of the venous system without causing hyperemia.

In certain embodiments, the (lev)cromakalim formulation is a clear aqueous solution including but not limited to an aqueous micellar or nanomicellar solution. In another embodiment, the topical formulation is not an emulsion, which for example, could be less clear or even milky and may disturb vision. In another embodiment, the topical formulation does not include an oil as that term is defined specifically below.

In certain embodiments, the topical formulation provided herein has the potential to provide a paradigm shift in the use of (lev)cromakalim for ocular delivery to lower intraocular pressure which can reduce the risk of damage to the optic nerve, and thus can be used for the treatment of glaucoma, and diseases resulting from or exacerbated by increased intraocular pressure, as well as diseases where the further lowering of intraocular pressure is beneficial to reducing disease progression, for example normal tension glaucoma (NTG). This invention does not require micro- or nano-particle formulation or the manufacture of a covalent prodrug. The (lev)cromakalim formulation can be advantageously used as a topical drop or via other route for ocular delivery.

In certain aspects of the embodiments, the topical pharmaceutical ocular formulation that can be used as an eye drop includes at least 0.01 mM or at least 0.05 mM, and typically not more than about 5 mM of cromakalim, typically levcromakalim, or a pharmaceutically acceptable salt thereof, in an aqueous liquid that is stable under ambient conditions for at least five months without significant crystallization or undue separation of cromakalim from the liquid and does not include DMSO, DMF or NMP or other unacceptable topical carrier for human use and has at least two excipients in addition to optional buffer, as described in more detail herein.

In certain aspects of this embodiment, the topical pharmaceutical ocular formulation that can be used as an eye drop includes at least 0.1 mM, and typically not more than about 5 mM of cromakalim, typically levcromakalim, or a pharmaceutically acceptable salt thereof, in an aqueous liquid that is stable under ambient conditions for at least five months without significant crystallization or undue separation of cromakalim from the liquid and does not include DMSO, DMF or NMP or other unacceptable topical carrier for human use and has at least two excipients in addition to optional buffer, as described in more detail herein.

In certain aspects of this embodiment, the topical pharmaceutical ocular formulation that can be used as an eye drop includes at least 0.25 mM or even at least 0.5 mM of (lev)cromakalim, typically levcromakalim, and may range up to 1, 1.5, 2.0, or 2.5, and typically not more than about 5 mM of (lev)cromakalim, or a pharmaceutically acceptable salt thereof, in an aqueous liquid that is stable under ambient conditions for at least five months without significant crystallization or undue separation of cromakalim from the liquid and does not include DMSO, DMF or NMP or other unacceptable topical carrier for human use and has at least two excipients in addition to optional buffer, as described in more detail herein.

In additional aspects of these embodiments, the topical pharmaceutical ocular formulation for humans is stable under ambient conditions for at least six, seven, eight or nine months. The term "significant" when used in this context means that the cromakalim, or levcromakalim, or its pharmaceutically acceptable salt, does not crystallize or separate enough to materially decrease the concentration below +/−5% from the initial concentration.

In certain embodiments, the present invention provides an ocular topical formulation comprising cromakalim, such as levcromakalim (e.g., (lev)cromakalim)), that is meant to mean cromakalim that may be a mixture of enantiomers or primarily or solely in the levo configuration), or a pharmaceutically acceptable salt thereof, and mixtures of selected pharmaceutically acceptable components, which provide (i) at least about 0.05, 0.5, 1.0, 1.5, 2.0, or 2.5, and typically not more than about 5 mM of (lev)cromakalim or a pharmaceutically acceptable salt thereof and (ii) stability of cromakalim, such as levcromakalim, in the formulation of at least 4 months, and typically 5, 6 or 7 or more months under ambient conditions (i.e., without significant crystallization or separation from the formulation that reduces the concentration of cromakalim, such as leveromakalim below +/−5% or below +/−10% of the original amount). The components of the formulation are required to be stable with each other for the same time period under ambient conditions. The topical formulation of the present invention using an effective amount of cromakalim, for example, levcromakalim, thereof, in certain advantageous embodiments does not result in significantly meaningful or prolonged hyperemia (which can result in moderate to severe "red eye", vascular congestion, small bleeds, small punctate bleeds or microhemorrhages) when provided to a host in need thereof. Where mM or mg/mL concentrations are used herein, the active compound is measured without regard to any salt form.

In addition, the (lev)cromakalim formulation of the present invention optionally exhibits an osmolarity between about 200 and 400 Osm/L, and more typically, between about 250 and 350 Osm/L. This is a measure of the total solute concentration within a specific volume of a solvent expressed in osmoles per liter (Osm/L). Hyperosmolarity can damage ocular tissue and stimulate epithelial cell death, which then initiates an inflammatory cascade which can lead to cell death via apoptosis.

In one aspect, therefore, the invention provides an aqueous formulation that comprises, includes, consists essentially of or consists of cromakalim (for example levcromakalim), which may be a pharmaceutically acceptable salt, Kolliphor® (which may be for example, but not limited to, EL, HS, RH, ELP or etc.), polysorbate (which may be, for example, but not limited to polysorbate 20, 40, 60, 80 or etc.), PVP (polyvinylpyrrolidone; which may be, for example, but not limited to, PVP-K30, PVP-K90, etc.), poloxamer (which may be, but not limited to, poloxamer 407 or etc.), mannitol, water, phosphate buffer, and optionally benzalkonium chloride (BAK) and/or a pH adjusting agent; wherein the formulation satisfies (i) and (ii) above; i.e., has a concentration of cromakalim of at least 0.01, 0.05, 0.5, 1, 1.5, 2, or 2.5, and typically not more than about 5 mM, is stable at ambient conditions for at least 5 months, and has a pH of about 6-8 or more particularly 6.5-7.5.

In primary embodiments, the aqueous formulation is not an emulsion, and certainly not an emulsion that has decreased transparency or is even milky, that could disturb the vision. For example, in certain embodiments the aqueous formulation is clear (e.g., a solution with a percent transmittance of greater than 85%, 90%, or 95%). In additional aspects the cromakalim formulation is a clear aqueous solution including but not limited to an aqueous micellar or nanomicellar solution. In certain embodiments, the topical formulation does not include an oil as it is specifically defined below.

In another aspect, the invention provides an aqueous formulation that comprises, includes, consists essentially of or consists of cromakalim (for example levcromakalim) or a pharmaceutically acceptable salt thereof, glycerin, Kolliphor® (which may be for example, but not limited to, EL, HS, RH or ELP), polysorbate (which may be, for example, but not limited to polysorbate 20, 40, 60 or 80), poloxamer (which may be, but not limited to, poloxamer 407), hypromellose, mannitol, water, phosphate buffer, and optionally benzalkonium chloride and/or a pH adjusting agent; wherein the formulation satisfies (i) and (ii) above; i.e., has a concentration of cromakalim of at least 0.01, 0.05, 0.5, 1, 1.5, 2, or 2.5, and typically not more than about 5 mM, is stable at ambient conditions for at least 5 months, and has a pH of about 6-8 or more particularly 6.5-7.5.

In yet another aspect, the invention provides an aqueous formulation that comprises, includes, consists essentially of or consists of (lev)cromakalim (for example levcromakalim) or a pharmaceutically acceptable salt thereof, glycerin, Kolliphor® (which may be for example, EL, HS, RH or ELP), polysorbate (which may be, for example, but not limited to polysorbate 20, 40, 60 or 80), poloxamer (which may be, for example, but not limited to poloxamer 407), PVP, mannitol, water, phosphate buffer, and optionally benzalkonium chloride and/or a pH adjusting agent; wherein the formulation satisfies (i) and (ii) above; i.e., has a concentration of cromakalim of at least 0.01, 0.05, 0.5, 1, 1.5, 2, or 2.5, and typically not more than about 5 mM, is stable at ambient conditions for at least 5 months, and has a pH of about 6-8 or 6.5-7.5.

In some aspects, the ocular formulation is an aqueous formulation containing a mixture of components selected from glycerin, polysorbate 80, poloxomer 407, Pluronic® F127, tyloxapol, Kolliphor® ELP, Kolliphor® RH 40, Kolliphor® HS 15, polyoxyl-25 castor oil, carboxymethyl cellulose (CMC), hypromellose, sodium-CMC, PVP, Premulen™ (which may be, for example, TR-1 or TR-2), and octoxynol-40 which satisfy (i) and (ii) above; has a concentration of (lev)cromakalim or a pharmaceutically acceptable salt thereof of at least 0.01, 0.05, 0.5, 1, 1.5, 2, or 2.5, and typically not more than about 5 mM, is stable at ambient conditions for at least 5 months, and has a pH of about 6-8 or 6.5-7.5.

In another aspect, the present invention provides an aqueous formulation of cromakalim, such as levcromakalim or a pharmaceutically acceptable salt thereof of at least 0.01, 0.05, 0.5, 1, 1.5, 2, or 2.5, and typically not more than about 5 mM, that is stable for at least 5 months under ambient conditions, has a pH of about 6-8 or 6.5-7.5, and comprises, includes, consists essentially of or consists of cromakalim (for example levcromakalim), and a polyethoxylated polyhydroxy (for example glycerol) ester. Non-limiting examples of a polyethoxylated polyhydroxy (for example glycerol) ester includes Kolliphor® EL, Kolliphor® ELP, Kolliphor® HS 15, Kolliphor® RH 40, Kolliphor® RH 60, Eumulgin® B25, polyoxyl 100 stearate, polyoxyl 40 stearate, polyoxyl 75 stearate, polyoxyl 6 stearate, and polyoxyl 32 stearate.

In yet another aspect, the present invention provides an aqueous formulation of cromakalim, such as levcromakalim or a pharmaceutically acceptable salt thereof of at least 0.01, 0.05, 0.5, 1, 1.5, 2, or 2.5, and typically not more than about 5 mM, with stability under ambient conditions of at least 5 months, has a pH of about 6-8 or 6.5-7.5, and comprises, includes, consists essentially of, or consists of cromakalim (for example levcromakalim), and a polyethoxylated furanose fatty acid ester. Non-limiting examples of a polyethoxylated furanose fatty acid ester includes polysorbate 20, polysorbate 40, polysorbate 60, polysorbate 65, and polysorbate 80.

In yet another aspect, the present invention provides an aqueous formulation of cromakalim, such as levcromakalim or a pharmaceutically acceptable salt thereof which has at least 0.01, 0.05, 0.5, 1, 1.5, 2, or 2.5, and typically not more than about 5 mM and has stability of at least 5 months under ambient conditions, has a pH of about 6-8 or 6.5-7.5, and comprises, includes, or consists essentially of cromakalim (for example levcromakalim), and a polymeric lactam. Non-limiting examples of a polymeric lactam includes polyvinylpyrrolidone (PVP) such as Kollidon® 12 PF, Kollidon® 17 PF, Kollidon® 25, Kollidon® 30; and polyvinylpolypyrrolidone (PVPP) such as Kollidon® VA 64, Kollidon® VA-fine, Kollidon® CL, Kollidon® CL-F, Kollidon® CL-SF, and Kollidon® CL-M.

In yet another aspect, the present invention provides an aqueous formulation of cromakalim, such as levcromakalim or a pharmaceutically acceptable salt thereof which has at least 0.01, 0.05, 0.5, 1, 1.5, 2, or 2.5, and typically not more than about 5 mM of cromakalim, such as levcromakalim, and has stability of cromakalim, such as levcromakalim, in the formulation of at least 5 months under ambient conditions, has a pH of about 6-8 or 6.5-7.5, and comprises, includes, consists essentially of or consists of cromakalim (for example levcromakalim), and a triblock polyalkylene glycol or a poloxamer. Non-limiting examples of a triblock polyalkylene glycol includes poloxamer 407, poloxamer 188, poloxamer 237, poloxamer 338, Pluronic® 127, and Synperonic 108.

In yet another aspect, the present invention provides an aqueous formulation of cromakalim, such as levcromakalim or a pharmaceutically acceptable salt thereof which has at least 0.01, 0.05, 0.5, 1, 1.5, 2, or 2.5, and typically not more than about 5 mM and has a stability of at least 5 months under ambient conditions, has a pH of about 6-8 or 6.5-7.5, and comprises, includes, consists essentially of, or consists of cromakalim (for example levcromakalim), and a hydroxyalkylcellulose. Non-limiting examples of a hydroxyalkylcellulose includes hypromellose or hydroxypropyl methylcellulose, hydroxyethylcellulose, hydroxymethylcellulose, hydroxypropylcellulose, (2-hydroxypropyl)-γ-cyclodextrin, hydroxypropyl-guar, dextran, xanthan gum, and guar gum.

In yet another aspect, the present invention provides an aqueous formulation of cromakalim, such as levcromakalim or a pharmaceutically acceptable salt thereof which has at least 0.01, 0.05, 0.5, 1, 1.5, 2, or 2.5, and typically not more than about 5 mM of cromakalim, such as levcromakalim, and has a stability of (lev)cromakalim in the formulation of at least 5 months under ambient conditions, has a pH of about 6-8 or 6.5-7.5, and comprises, includes or consists essentially of cromakalim (for example levcromakalim), and a polyol, for example a triol. Non-limiting examples of a triol includes glycerin, polyglycerol, and polyglycerol polyricinoleate.

In yet another aspect, the present invention provides an aqueous formulation of cromakalim, such as levcromakalim or a pharmaceutically acceptable salt thereof, of at least 0.01, 0.05, 0.5, 1, 1.5, 2, or 2.5, and typically not more than about 5 mM and stability of (lev)cromakalim the formulation is at least 5 months under ambient conditions, has a pH of about 6-8 or 6.5-7.5, and comprises, includes or consists essentially of cromakalim (for example levcromakalim), and a polyol of the subtype sugar alcohol. Non-limiting examples of a sugar alcohol includes mannitol, ethylene glycol, glycerol, mannitol, sorbitol, erythritol, threitol, arabitol, xylitol, ribitol, galactitol, fucitol, iditol, inositol, volemitol, isomalt, maltitol, lactitol, maltotriitol, maltotetraitol, and polyglycitol.

In yet another aspect, the present invention provides an aqueous formulation of cromakalim, such as levcromakalim or a pharmaceutically acceptable salt thereof, which has at least 0.01, 0.05, 0.5, 1, 1.5, 2, or 2.5, and typically not more than about 5 mM of cromakalim, such as levcromakalim, and the stability of the formulation is at least 5 months under ambient conditions, has a pH of about 6-8 or 6.5-7.5, and comprises, includes or consists essentially of cromakalim (for example levcromakalim), and a polyol of the subtype polymeric alkyl or aryl polyol. Non-limiting examples of a polymeric polyol includes polyethylene glycol, polypropylene glycol, poly(tetramethylene ether) glycol, sorbitol polyether polyol, sucrose polyether polyol, tyloxapol, and polyvinyl alcohol.

In some aspects, the present invention provides an aqueous formulation of cromakalim, such as levcromakalim which has at least 0.01, 0.05, 0.5, 1, 1.5, 2, or 2.5, and typically not more than about 5 mM of cromakalim, such as levcromakalim or a pharmaceutically acceptable salt thereof, the stability of (lev)cromakalim in the formulation is at least 5 months under ambient conditions, and the formulation has a pH of about 6-8 or 6.5-7.5, and optionally includes or comprises of BAK (benzalkonium chloride).

The cromakalim formulation of the present invention in an effective amount can be topically delivered, for example, to treat glaucoma associated with elevated intraocular pressure, including but not limited to primary open angle glaucoma (POAG), (also known as chronic open angle glaucoma, chronic simple glaucoma and glaucoma simplex), primary angle closure glaucoma, pediatric glaucoma, pseudo-exfoliative glaucoma, pigmentary glaucoma, traumatic glaucoma, neovascular glaucoma, irido corneal endothelial glaucoma (ICE), uveitic glaucoma, steroid induced glaucoma, acute glaucoma resulting from advanced cataracts and/or from intravitreal injections.

In certain embodiments, the levcromakalim formulation of the present invention can be used in an effective amount to treat elevated intraocular pressure associated with diabetic retinopathy or diabetic retinopathy induced glaucoma.

In another embodiment, the present formulation is used to treat glaucoma that is not associated with elevated intraocular pressure, including but not limited to normal tension glaucoma (NTG) (also known as low tension glaucoma or normotensive glaucoma).

An effective amount of the topical formulation of cromakalim, for example, levcromakalim, or a pharmaceutically acceptable salt thereof as described herein can also be used to treat a host in need thereof either as primary or secondary or adjunctive treatment as part of the protocol for MIGS (Microinvasive Glaucoma Surgery), including but not limited to miniature version of trabeculectomy (microtrabeculectomy), trabecular bypass surgery, totally internal or suprachoroidal shunts, milder/gentler versions of laser cyclo photocoagulation, and in an alternative embodiment, a Schlemm's canal stent that dilates Schlemm's canal, goniotomies, canaloplasties, and laser trabeculoplasties.

In other aspects, the present ocular formulation can also be used in an effective amount to treat Sturge Weber Syndrome, which is not limited to but includes Glaucoma associated with elevated episcleral venous pressure (EVP). Sturge Weber Syndrome is a congenital disorder that affects the skin, neurological system and sometimes the eyes. It is sometimes referred to as a neurocutaneous disorder. Sturge Weber Syndrome can result in Sturge Weber Syndrome-induced glaucoma, which affects 30-70% of the patients with this disorder.

In certain embodiments, the ocular formulation of the present invention has (lev)cromakalim at the concentration of at least 0.01 mg/mL, 0.05 mg/mL, 0.1 mg/mL, 0.15 mg/mL, 0.5 mg/mL, 1 mg/mL, or 1.4 mg/mL, and typically not more than 1.5 mg/mL.

Specific non-limiting illustrative examples of the invention are described herein. In certain embodiments, the ocular formulation includes at least (lev)cromakalim or a pharmaceutically acceptable salt thereof, polysorbate, Kolliphor, and PVP and has a concentration of (lev)cromakalim of at least 0.01, 0.05, 0.4, 0.5, 0.8, 0.9, 1, 1.5, 2, or 2.5, and typically not more than about 5 mM and is stable at ambient conditions for at least 5 months.

In other aspects, the ocular formulation includes at least (lev)cromakalim or a pharmaceutically acceptable salt thereof, Kolliphor, polysorbate, and poloxamer and has a concentration of (lev)cromakalim of at least 0.01, 0.05, 0.4, 0.5, 0.8, 0.9, 1, 1.5, 2, or 2.5, and typically not more than about 5 mM and is stable at ambient conditions for at least 5 months.

In additional aspects, the ocular formulation has at least Kolliphor, polysorbate, PVP, and poloxamer and has a concentration of at least 0.01, 0.05, 0.4, 0.5, 0.8, 0.9, 1, 1.5, 2, or 2.5, and typically not more than about 5 mM of (lev)cromakalim or a pharmaceutically acceptable salt thereof and is stable at ambient conditions for at least 5 months.

In other embodiments, the ocular formulation has at least Kolliphor® EL or ELP, polysorbate 80, PVP, poloxamer 407, and mannitol and has a concentration of (lev)cromakalim or a pharmaceutically acceptable salt thereof of at least 0.01, 0.05, 0.4, 0.5, 0.8, 0.9, 1, 1.5, 2, or 2.5, and typically not more than about 5 mM and is stable at ambient conditions for at least 5 months.

In further aspects, the ocular formulation has at least glycerin, Kolliphor® EL or ELP, polysorbate 80, poloxamer 407, hypromellose, and PBS, and has a concentration of (lev)cromakalim or a pharmaceutically acceptable salt thereof of at least 0.01, 0.05, 0.4, 0.5, 0.8, 0.9, 1, 1.5, 2, or 2.5, and typically not more than about 5 mM and is stable at ambient conditions for at least 5 months.

In certain other embodiments, the ocular formulation includes at least Kolliphor® EL or ELP, polysorbate 80, PVP, poloxamer 407, mannitol; and benzalkonium chloride and has a concentration of (lev)cromakalim or a pharmaceutically acceptable salt thereof of at least 0.01, 0.05, 0.4, 0.5, 0.8, 0.9, 1, 1.5, 2, or 2.5, and typically not more than about 5 mM and is stable at ambient conditions for at least 5 months.

In other aspects, the ocular formulation has at least Kolliphor® EL or ELP, polysorbate 80, PVP, poloxamer 407, mannitol, and benzalkonium chloride and has a concentration of (lev)cromakalim or a pharmaceutically acceptable salt thereof of at least 0.01, 0.05, 0.4, 0.5, 0.8, 0.9, 1, 1.5, 2, or 2.5, and typically not more than about 5 mM and is stable at ambient conditions for at least 5 months.

Another aspect is an ocular formulation that has at least glycerin, Kolliphor® EL or ELP, polysorbate 80, poloxamer 407, hypromellose, and mannitol, and has a concentration of (lev)cromakalim or a pharmaceutically acceptable salt thereof of at least 0.01, 0.05, 0.4, 0.5, 0.8, 0.9, 1, 1.5, 2, or 2.5, and typically not more than about 5 mM and is stable at ambient conditions for at least 5 months.

In certain nonlimiting embodiments, the topical dosage can be administered once a day in the morning (QAM), once a day in the evening (QPM), every morning and at bedtime (QAM HS), every morning and evening (QAM PM), or once a day at bedtime (QHS).

In certain embodiments, the ocular formulation may be prepared as an aqueous solution or clear emulsion via heating, cooling, incubating, centrifuging, vortexing, standing, stirring, shaking, sonicating, or any combination thereof, including as described herein.

For example, in certain embodiments, the ocular formulation is prepared using a process wherein (lev)cromakalim or salt thereof and the other components are first individually or in groups dissolved in ethanol or other low volatile organic solvent(s), mixed and then evaporated under vacuum to produce a film which is then resuspended in buffer, typically a phosphate buffer, and deionized water, and optionally autoclaved, and filtered to yield the formulation.

In certain embodiments, the ocular formulation of (lev)cromakalim is delivered for storage in ocular tissues and are then released. The release from ocular tissue leads to the efficient absorption and pharmacological effect of levcromakalim, following administration of the immediate release formulation.

Therefore, in certain aspects, the present invention provides the efficient delivery of (lev)cromakalim or a pharmaceutically acceptable salt thereof via the topical administration of an effective amount of an ocular formulation to a host, including a human, to treat any of the disorders described herein, including but not limited to, for example, to lower intraocular pressure, or to treat glaucoma regardless of whether it includes the condition of increased pressure (such as normal tension glaucoma). In certain embodiments, the efficient delivery of (lev)cromakalim to the eye is achieved by the topical administration of one or more drops or applications, once, twice, or multiple times a day (or alternatively on alternating days), of the ocular formulation described herein. As nonlimiting illustrative embodiments, ocular formulations in Examples 5 and 6 are able to reduce the intraocular pressure significantly during in vivo efficacy studies performed in a mammal (mice), and the ocular formulas in Examples 8 and 9 are safely administered and tolerated by human subjects, wherein lowering of intraocular pressure is observed.

In certain embodiments, topical administration drops are administered through a single use (unit dose) pharmaceutical packaging. In certain embodiments, the unit dose packaging contains at least about 100 μL to about 500 μL, and more typically about 300 μL of the ocular formulation. In certain embodiments, the delivery volume per drop of the formulation delivered through the unit dose packaging is at least about 10 μL to about 50 μL, 20 μL to about 40 μL, and more typically about 30 μL per eye. In certain specific embodiments, the concentration of the (lev)cromakalim in the unit dose packaging is at least about 0.05 mM, 0.5 mM, 1 mM, 1.5 mM, or 2.5 mM, and typically not more than 5 mM. In certain specific embodiments, five of the unit dose dropper bottles are dispensed in a single foil packaging. In certain embodiments the concentration of (lev)cromakalim is between 0.5 and 2.5 mM. In certain embodiments the concentration of (lev)cromakalim is between 0.05 and 0.5 mM, between 0.5 and 1.5 mM, or between 1 and 2.5 mM.

In certain embodiments, an ocular formulation of the present invention lowers the intraocular pressure by lowering the episcleral venous pressure (EVP). For example, as described in Example 7, the lowering of IOP in C57BL/6J mice is the result of lowering of the EVP and a significant change in IOP is observed, and no significant change is found in outflow facility, uveoscleral outflow or aqueous humor flow rate.

In certain embodiments, an ocular formulation of (lev)cromakalim or a pharmaceutically acceptable salt thereof is administered to the eye, for example, as a topical drop, and delivers (lev)cromakalim in the eye, for example to the sclera, conjunctiva, optic nerve, cornea, iris, ciliary body, trabecular meshwork, and/or the retina.

In certain embodiments, the pH of the ocular formulation of (lev)cromakalim is adjusted using a pharmaceutically acceptable base to the desired pH level for pharmaceutical administration, often between about 6-8, and more typically between 6.5 and 7.5.

In certain embodiments, the ocular formulation of (lev) cromakalim is not an emulsion, a suspension, or a gel. In certain embodiments the ocular formulation of (lev)cromakalim is an aqueous clear solution which is not an emulsion. For example, in certain embodiments the ocular formulation of (lev)cromakalim is a clear solution, a clear micellar solution, or a clear nanomicellar solution. In certain embodiments, the formulation does not include an oil as defined below. The invention thus includes at least the following illustrative aspects:

(i) An ocular topical formulation that has a concentration of (lev)cromakalim or a pharmaceutically acceptable salt of at least 0.01, 0.05, 0.4, 0.5, 0.8, 0.9, 1, 1.5, 2, or 2.5, and typically not more than about 5 mM and is stable at ambient conditions for at least 5 months and comprises three or more components selected from the group of a triol or polyol (typically aliphatic, and more typically alkyl) (for example glycerin); a polyethoxylated furanose fatty acid ester (for example a polysorbate); a nonionic tri-block copolymer of a central hydrophobic chain of polyoxypropylene (poly(propylene oxide)) flanked by two hydrophilic chains of polyoxyethylene (poly(ethylene oxide)) (for example a poloxamer or Pluronic); an alkyl aryl polyol (for example tyloxapol); an ethoxylated glycerol ester (for example Kolliphor® EL or ELP, Cremophor®, Kolliphor® RH 40 or Kolliphor® HS 15); polyoxyalkylene castor oil; carboxymethyl cellulose/CMC; hypromellose; a polymeric lactam (for example PVP); an oil in water polymeric emulsifier of a block copolymer of polyacrylic acid and a hydrophobic $C_{10}$-$C_{30}$ alkyl acrylate (for example, Premulen™ TR-1 or Premulen™ TR-2); and an ethoxylated alkylphenol (for example octoxynol-40); in an aqueous formulation with a pH from about 6 to 8 or 6.5-7.5;

(ii) An ocular topical formulation of (lev)cromakalim or a pharmaceutically acceptable salt thereof that has a concentration of at least 0.01, 0.05, 0.4, 0.5, 0.8, 0.9, 1, 1.5, 2, or 2.5, and typically not more than about 5 mM and is stable at ambient conditions for at least 5 months and comprises three or more components selected from the group consisting of glycerin, polysorbate 80, poloxomer 407, Pluronic® F127, tyloxapol, Kolliphor® (for example Kolliphor® EL or ELP, Cremophor®, Kolliphor® RH 40 or Kolliphor® HS 15), polyoxyl-25 castor oil, carboxymethyl cellulose/CMC, hypromellose, PVP, Premulen™ (for example TR-1 or TR-2), and octoxynol-40 in an aqueous solution; in an aqueous formulation with a pH from about 6 to 8 or 6.5-7.5;

(iii) An aqueous ocular formulation that comprises, consists essentially of or consists of (lev)cromakalim or a pharmaceutically acceptable salt thereof, Kolliphor® (for example Kolliphor® (for example Kolliphor® EL or ELP, Cremophor®, Kolliphor® RH 40 or Kolliphor® HS 15), polysorbate (which may be for example, 20, 40, 60 or 80), polyvinylpyrrolidone (PVP), poloxamer (which may be, for example, 407), mannitol, water or phosphate buffer, and optionally benzalkonium chloride and optionally a pH adjusting agent; that has a concentration of (lev)cromakalim of at least 3.5 mM, and typically not more than about 5 mM, and is stable at ambient conditions for at least 5 months with a pH of 6-8 or 6.5-7.5;

(iv) An aqueous ocular formulation that comprises, consists essentially of or consists of (lev)cromakalim or a pharmaceutically acceptable salt thereof, glycerin, Kolliphor® (for example Kolliphor® EL or ELP, Cremophor®, Kolliphor® RH 40 or Kolliphor® HS 15), polysorbate (which may be, for example, 20, 40, 60 or 80), poloxamer (which may be, for example, 407), hypromellose, mannitol, and optionally benzalkonium chloride and optionally a pH adjusting agent; wherein the formulation has a concentration of (lev)cromakalim of at least 0.01, 0.05, 0.4, 0.5, 0.8, 0.9, 1, 1.5, 2, or 2.5, and typically not more than about 5 mM and is stable at ambient conditions for at least 5 months and has a pH of 6-8 or 6.5-7.5;

(v) An aqueous ocular formulation that comprises, consists essentially of or consists of (lev)cromakalim or a pharmaceutically acceptable salt thereof, glycerin, Kolliphor® (for example Kolliphor® EL or ELP, Cremophor®, Kolliphor® RH 40 or Kolliphor® HS 15), polysorbate (which may be for example, 20, 40, 60 or 80), poloxamer (which may be, for example, 407), PVP, mannitol, and optionally benzalkonium chloride and optionally a pH adjusting agent; wherein the formulation; i.e., has a concentration of (lev)cromakalim of at least 0.01, 0.05, 0.4, 0.5, 0.8, 0.9, 1, 1.5, 2, or 2.5, and typically not more than about 5 mM and is stable at ambient conditions for at least 5 months and has a pH of 6-8 or 6.5-7.5;

(vi) The treatment of a host in need thereof for any of the disorders described herein, including but not limited to the treatment of glaucoma generally and/or lowering intraocular pressure, comprising administering an effective amount of an aqueous topical formulation of (i)-(v) to treat an ocular disorder or any other disorder described herein in the host in need thereof, (vii) The aqueous ocular formulation of (i)-(v) for use to treat a host in need of treating any of the disorders described herein, including but not limited to the treatment of glaucoma generally and/or lowering intraocular pressure;

(viii) The use of an aqueous ocular formulation of (i)-(v) to treat a host in need of treatment for any of the disorders described herein, including but not limited to the treatment of glaucoma generally and/or lowering intraocular pressure;

(ix) A process for the manufacture of a medicament that includes an aqueous formulation of (i)-(v) for the treatment of a host for any of the disorders described herein;

(x) The formulation as described herein for use in the manufacture of a medicament in the treatment of the disorders described herein, including but not limited to the treatment of glaucoma generally and/or lowering intraocular pressure;

(xi) Aspects of (vi)-(x) to treat glaucoma associated with elevated intraocular pressure, including but not limited to primary open angle glaucoma (POAG) (also known as chronic open angle glaucoma, chronic simple glaucoma and glaucoma simplex), primary angle closure glaucoma, pediatric glaucoma, pseudo-exfoliative glaucoma, pigmentary glaucoma, traumatic glaucoma, neovascular glaucoma, irido corneal endothelial glaucoma (ICE), uveitic glaucoma, steroid induced glaucoma, glaucoma associated with diabetic retinopathy, acute glaucoma resulting from advanced cataracts and/or from intravitreal injections, and glaucoma that is not associated with elevated intraocular pressure, including but not limited to normal tension glaucoma (NTG) (also known as low tension glaucoma or normotensive glaucoma);

(xii) Aspects of (vi)-(x) to treat Sturge Weber Syndrome, including but not limited to Sturge Weber Syndrome-induced glaucoma in a host in need thereof, (xiii) Aspects of (vi)-(x) that do not result in significantly meaningful hyperemia (which can result in "red eye", vascular congestion, small bleeds, small punctate bleeds or microhemorrhages) in a host in need of treatment;

(xiv) Aspects of (vi)-(xiii) as primary or secondary or adjunctive treatment as part of the protocol for MIGS (Microinvasive Glaucoma Surgery), including but not limited to miniature versions of trabeculectomy (microtrabeculectomies), trabecular bypass surgeries, totally internal or suprachoroidal shunts, milder/gentler versions of laser cyclo photocoagulation, and in alternative embodiments, use in connection with Schlemm's canal stents that dilate Schlemm's canal, goniotomies, canaloplasties, and laser trabeculoplasties;

(xv) Aspects of (vi)-(xiii) to treat an ocular disorder in a host such as Graves' ophthalmopathy, thyroid-associated orbitopathy (TAO), Graves' orbitopathy (GO), retrobulbar tumors, cavernous sinus thrombosis, orbital vein thrombosis, episcleral/orbital vein vasculitis, superior vena cava obstruction, superior vena cava thrombosis, carotid cavernous sinus fistula, dural cavernous sinus shunts, orbital varices, central retinal vein occlusion (CRVO), branch retinal vein occlusion (BRVO), artery occlusive/embolic and or hypoperfusion diseases, optic nerve damage due to ischemia (posterior and anterior ischemic optic neuropathy (NAION); and (xvi) Aspects of (vi)-(xiii) to provide cellular protection and/or neuroprotection to a host in need thereof.

DETAILED DESCRIPTION OF FIGURES

FIG. 1 depicts the lowering of intraocular pressure (IOP) in normotensive mice by formulation 3f and formulation 3d with vehicle as a negative control and levcromakalim in DMSO/Cremophor EL as a positive control, as detailed in Example 5. Baseline depicts pre-administration IOP levels. Y-axis depicts the intraocular pressure in mmHg. IOP measurements were performed in triplicate at each of 2 daily time points (1 h and 23 h) that are averaged to compute a daily IOP. The graph shows the mean and standard deviation of Day 3 and day 4 daily IOPs.

Figure 2:
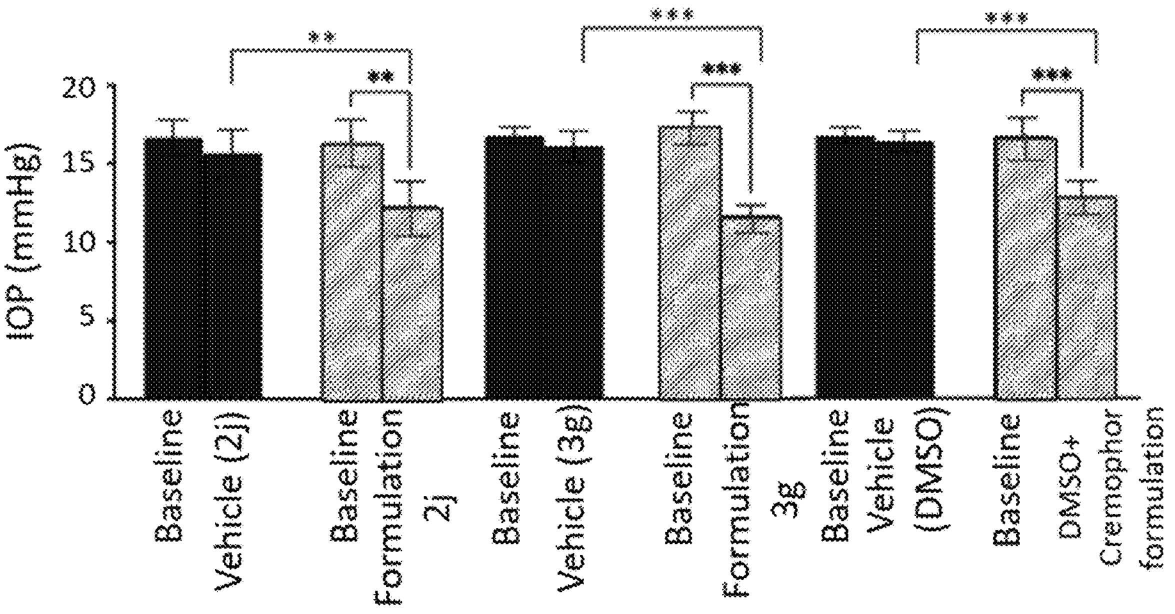

FIG. 2 depicts the lowering of intraocular pressure (IOP) in normotensive mice by specific formulation 2j, and formulation 3 g with vehicle as a negative control and levcromakalim in DMSO/Cremophor EL as a positive control, as detailed in Example 6. Baseline depicts pre-administration IOP levels. Y-axis depicts the intraocular pressure in mmHg. IOP measurements were performed in triplicate at each of 2 daily time points (1 h and 23 h) that are averaged to compute a daily IOP. The graph shows the mean and standard deviation of Day 3 and day 4 daily IOPs.

Figure 3:
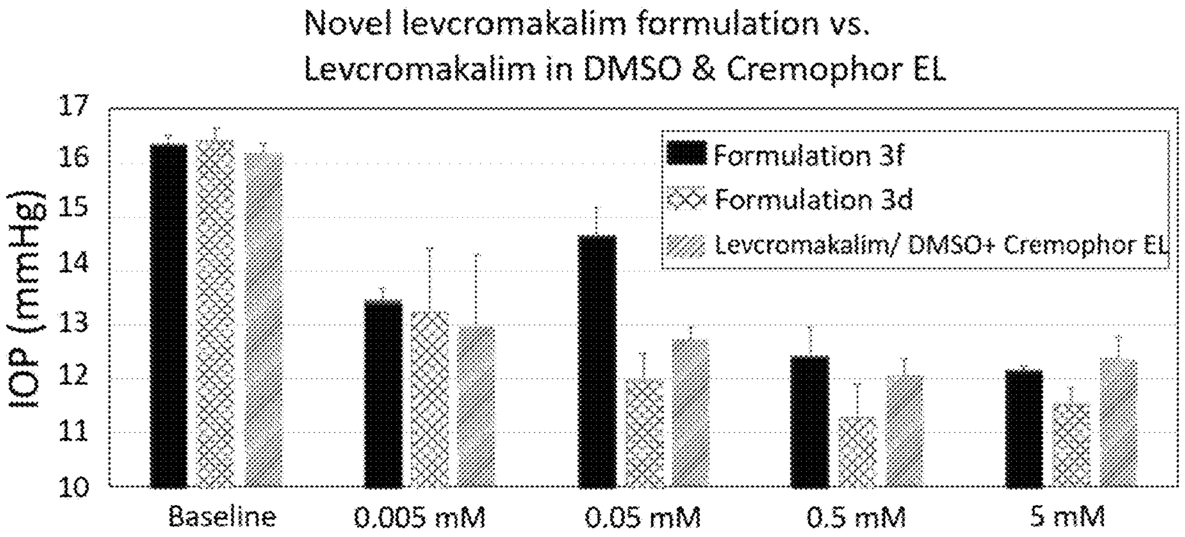
Figure 4:
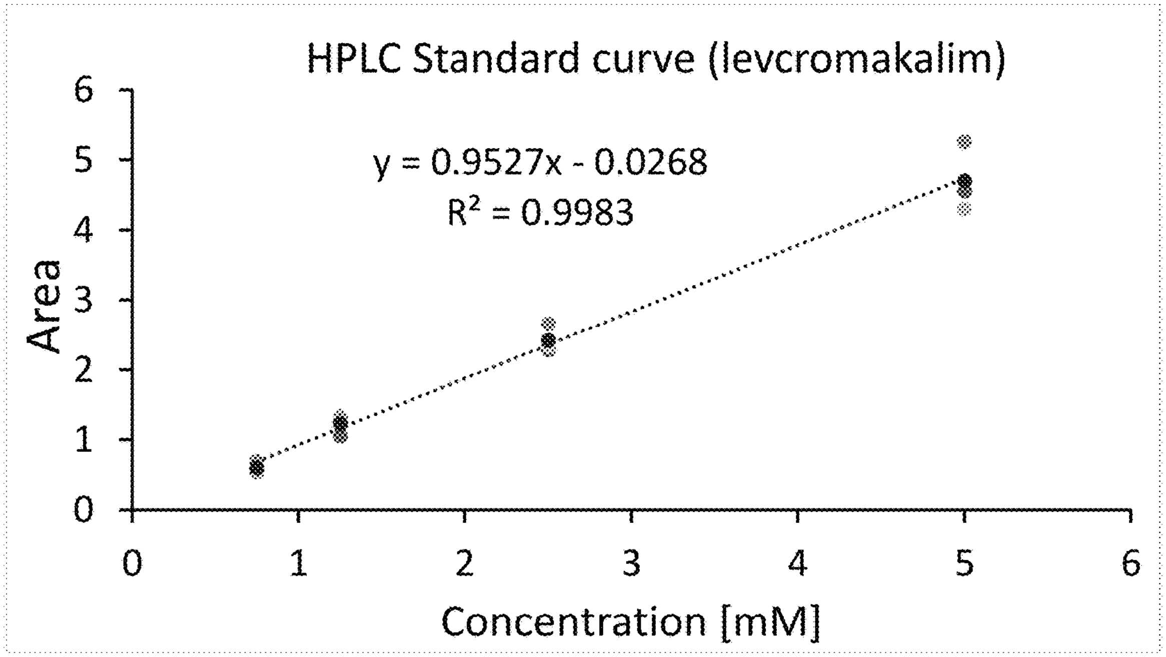

FIG. 3 depicts the lowering of intraocular pressure (IOP) in normotensive mice at different concentrations of levcromakalim formulated in specific formulation 3f, and formulation 3d, and DMSO-Cremophor EL, as detailed in Example 5. Baseline depicts pre-administration IOP levels. X-axis depicts concentration of levcromakalim, and Y-axis depicts intraocular pressure in mmHg. IOP measurements were performed in triplicate at each of 2 daily time points (1 h and 23 h) that are averaged to compute a daily IOP. The graph shows the mean and standard deviation of Day 3 and day 4 daily IOPs FIG. 4 depicts the High-Performance Liquid Chromatography (HPLC) standard curve of leveromakalim standards as described in Table 1 of the section VIII. The graph shows the mean, and the standard deviation of the measurements done in triplicates. X-axis depicts the concentration of levcromakalim standard, and Y-axis depicts the area of the peak indicating elution of levcromakalim. This standard curve is used in Examples 1-4.

Figure 5:
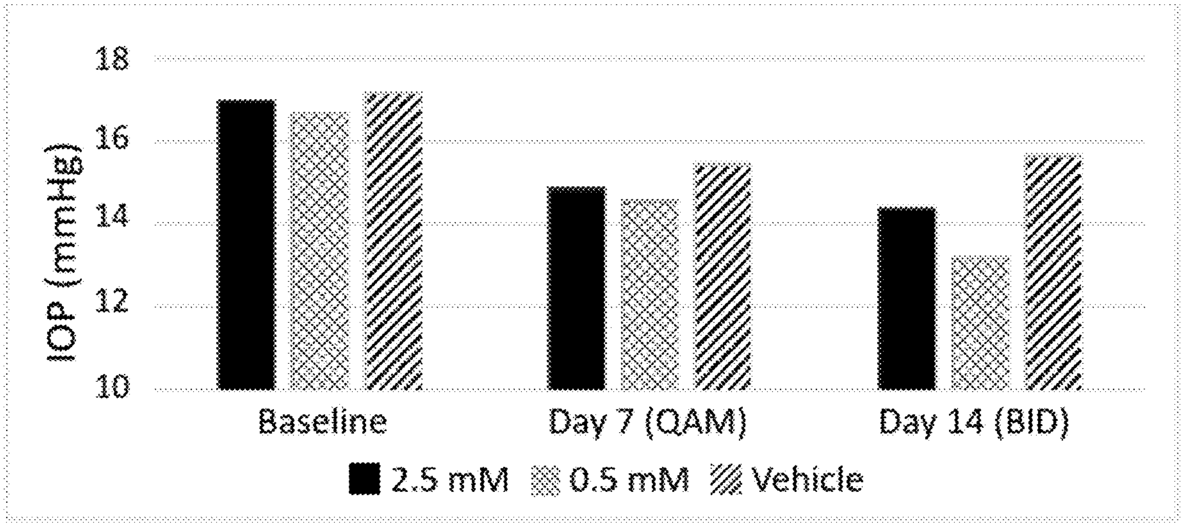

FIG. 5 depicts mean diurnal IOP in 21 patients upon administration of formulation 3d (2.5 and 0.5 mM) and vehicle control at baseline, Day 7, and Day 14 (GAT). Baseline depicts pre-administration IOP levels. Y-axis depicts the intraocular pressure in mmHg. Details are provided in Example 9.

Figure 6:
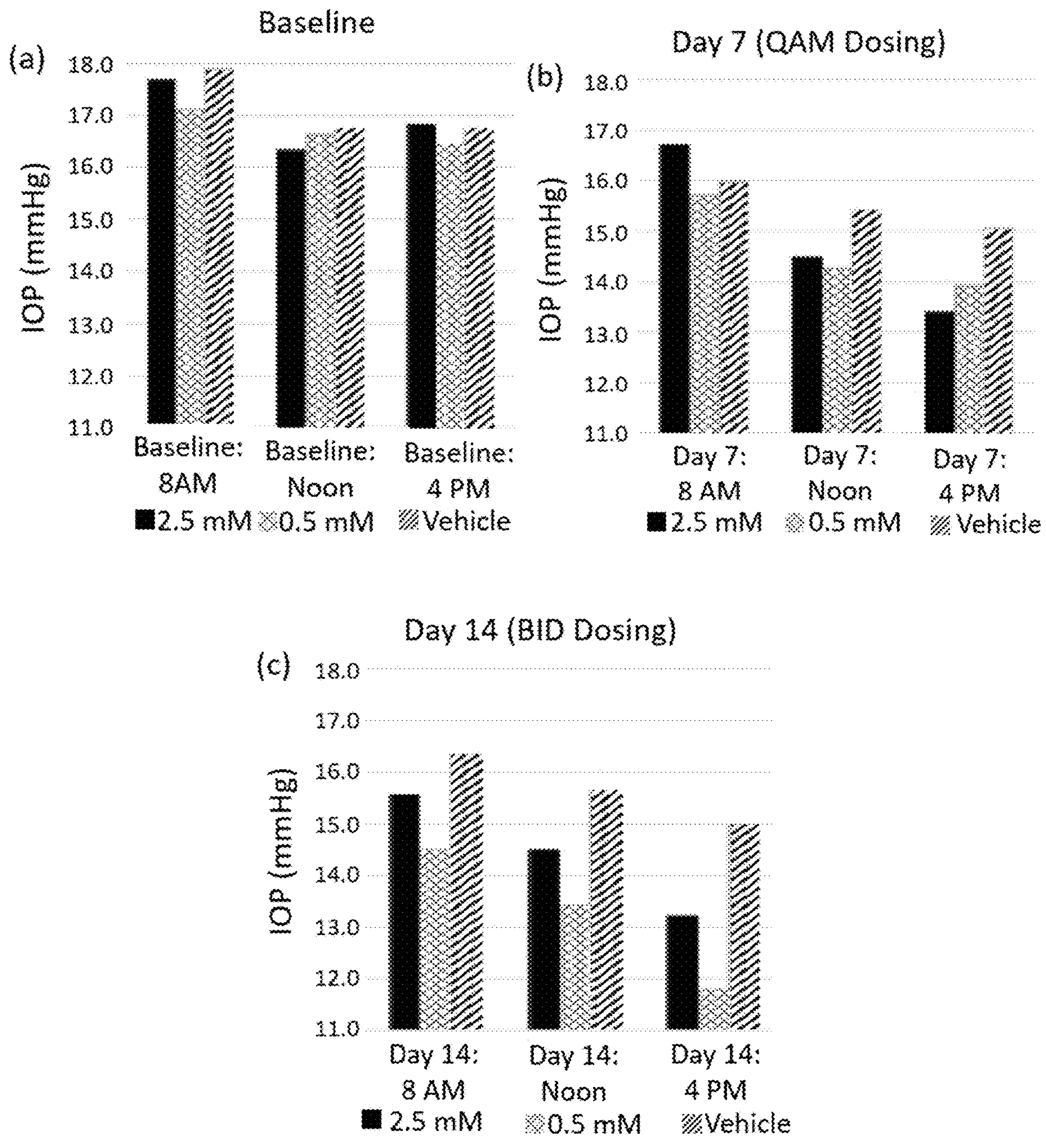

FIG. 6 depicts (a) Baseline IOP (GAT) pre-dosing OU with formulation 3d or vehicle (n=7 per treatment group [14 eyes]); (b) IOP measured on Day 7 following QAM dosing for 7 days with formulation 3d or vehicle (n=7 per treatment group [14 eyes]); (c) IOP measures on Day 14 following BID dosing for 7 days with formulation 3d or vehicle (n=7 per treatment group [14 eyes]). Details are provided in Example 9.

Figure 7:
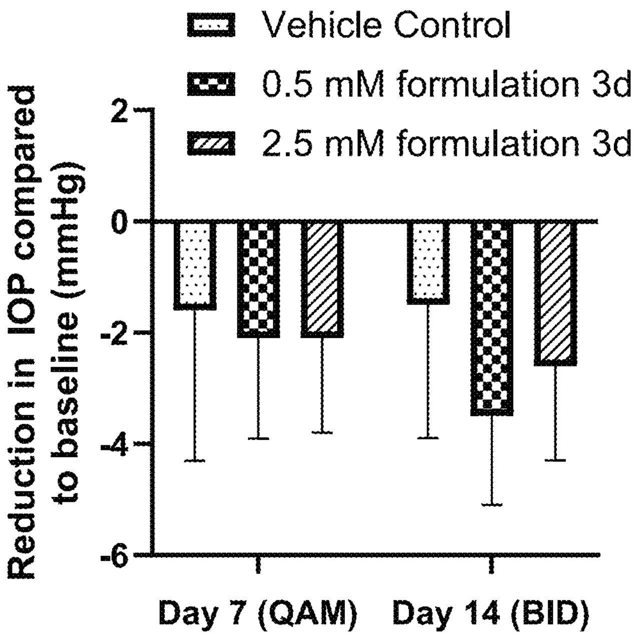

FIG. 7 depicts reduction in mean diurnal IOP compared to the baseline in 21 patients upon administration of formulation 3d (2.5 and 0.5 mM) and vehicle control at day 7 and Day 14 (GAT). Y-axis depicts the reduction in intraocular pressure in mmHg. Details are provided in Example 9.

Figure 8:
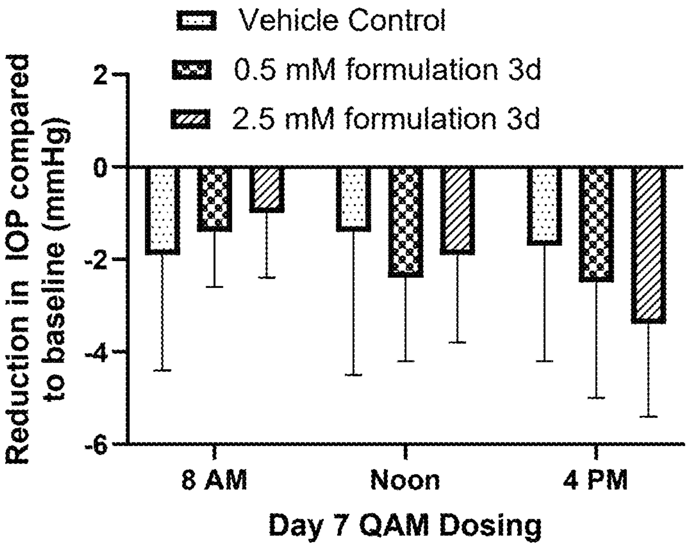
Figure 8:
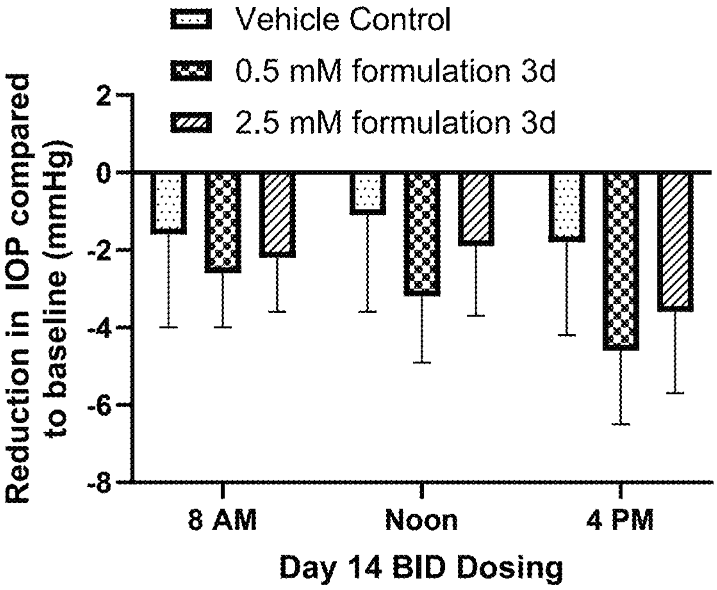

FIG. 8 depicts (a) reduction in IOP measured on Day 7 compared to the baseline following QAM dosing for 7 days with formulation 3d or vehicle (n=7 per treatment group [14 eyes]); (b) reduction in IOP measures as compared to the baseline on Day 14 following BID dosing for 7 days with formulation 3d or vehicle (n=7 per treatment group [14 eyes]). Details are provided in Example 9.

DETAILED DESCRIPTION OF THE INVENTION

It has been surprisingly discovered that the parent cromakalim drug, for example, levcromakalim (and wherein the compound without regard to stereochemistry or in either stereoconfiguration (for example (-) or without regard to stereochemistry), is referred to as (lev)cromakalim), or a pharmaceutically acceptable salt thereof, can be delivered topically and efficiently in drop form in an effective therapeutic amount to treat any of the indications affecting anterior and posterior segments described herein that are responsive to (lev)cromakalim, including but not limited to ocular disorders associated with elevated intraocular pressure, ocular disorders not associated with elevated intraocular pressure such as normal tension glaucoma or any glaucoma generally. The (lev)cromakalim formulation of the present invention can be used to treat the anterior portion of the human eye without the use of a covalent prodrug approach, a polymeric delivery system or a high level of toxic components, through the employment of excipient combinations described herein. It is a significant advance that a stable topical pharmaceutical formulation that provides an effective amount of (lev)cromakalim for humans is finally provided, almost 40 years after the discovery of the drug.

The structure of the eye can be divided into two segments: the anterior and posterior. The anterior segment comprises the front third of the eye and includes the structures in front of the vitreous humor: the cornea, iris, ciliary body, and lens. The posterior segment includes the back two-thirds of the eye and includes the sclera, choroid, retinal pigment epithelium, neural retina, optic nerve, and vitreous humor. The formulation of the present invention can be used to treat an anterior or posterior ocular disorder that is responsive to (lev)cromakalim.

The topical formulations provided herein have the potential to provide a paradigm shift in the use of (lev)cromakalim for ocular delivery to treat ocular disorders that respond to (lev)cromakalim, including but not limited to lowering intraocular pressure which can damage the optic nerve, and thus can be used for the treatment of glaucoma and other diseases resulting from or exacerbated by increased intraocular pressure, and also for the treatment of normal tension glaucoma. This invention does not require micro- or nano-particle formulations or the manufacture of a covalent prodrug. The cromakalim formulations can be advantageously used as a topical drop for ocular mucosal delivery.

The (lev)cromakalim formulation of the present invention is not contingent on endogenous conversions by phosphates (as compared to the phosphate prodrug QLS-101). The (lev)cromakalim formulation of the present invention is well suited for topical ophthalmic dosing due to its water-soluble nature.

The aqueous ocular formulations of the present invention are capable of providing at least about 0.01, 0.05, 0.4, 0.5, 0.8, 0.9, 1, 1.5, 2, or 2.5, and typically not more than about 5 mM concentration of (lev)cromakalim through the mucosal barrier and into the intraocular chamber that can reach the anterior portion of the eye. The aqueous formulations provided herein have a stability of (lev)cromakalim of at least 5 months, and for example 5, 6 or 7 or more months under ambient conditions (i.e., without undue crystallization or separation from the formulation that reduces the concentration of (lev)cromakalim below about +/−5% or below about +/−10% from the original concentration). The components of the formulation are required to be stable with each other for the same time period under ambient conditions. The aqueous ocular formulation has a pH in the range of about 6-8, and more typically 6.5-7.5, and an osmolarity between about 200 and 400 or 250 and 350.

In certain embodiments the ocular formulation of (lev) cromakalim is not an emulsion, a suspension, or a gel. In certain embodiments the ocular formulation of (lev)cromakalim is an aqueous clear solution which is not an emulsion. For example, in certain embodiments the ocular formulation of (lev)cromakalim is a clear solution, a clear micellar solution, or a clear nanomicellar solution. In certain embodiments, the formulation does not include an oil as defined below.

Whenever, in this specification, the following, or the like, is referred to such as 0.05, 0.1, 0.3, 0.5, 1, 2, 2.5, 3, or 3.5 mM (e.g., about 1 mg/mL), and even 4 (e.g., about 1.1 mg/mL), 4.5 or 5 mM (e.g., about 1.4 mg/mL), it should be understood that each concentration is specifically and uniquely referred to as a species disclosure and the list of concentrations is not intended by the inventors, and should not be, considered a genus disclosure that stands or falls together. This list of concentrations include but are not limited to the following:

In certain embodiments, an ocular formulation as described herein has a concentration of (lev)cromakalim or a pharmaceutically acceptable salt of 0.05 mM, or at least 0.05 mM, and no more than 5 mM.

In certain other embodiments, an ocular formulation as described herein has a concentration of (lev)cromakalim or a pharmaceutically acceptable salt of 0.1 mM, or at least 0.1 mM, and no more than 5 mM.

In certain other embodiments, an ocular formulation as described herein has a concentration of (lev)cromakalim or a pharmaceutically acceptable salt of 0.5 mM, or at least 0.5 mM, and no more than 5 mM.

In certain other embodiments, an ocular formulation as described herein has a concentration of (lev)cromakalim or a pharmaceutically acceptable salt of 1 mM, or at least 1 mM, and no more than 5 mM.

In certain other embodiments, an ocular formulation as described herein has a concentration of (lev)cromakalim or a pharmaceutically acceptable salt of 1.5 mM, or at least 1.5 mM, and no more than 5 mM.

In certain other embodiments, an ocular formulation as described herein has a concentration of (lev)cromakalim or a pharmaceutically acceptable salt of 2 mM, or at least 2 mM, and no more than 5 mM.

In certain other embodiments, an ocular formulation as described herein has a concentration of (lev)cromakalim or a pharmaceutically acceptable salt of 2.5 mM, or at least 2.5 mM, and no more than 5 mM.

In certain other embodiments, an ocular formulation as described herein has a concentration of (lev)cromakalim or a pharmaceutically acceptable salt of 3 mM, or at least 3 mM, and no more than 5 mM.

In certain other embodiments, an ocular formulation as described herein has a concentration of (lev)cromakalim or a pharmaceutically acceptable salt of 3.5 mM, or at least 3.5 mM, and no more than 5 mM.

In certain other embodiments, an ocular formulation as described herein has a concentration of (lev)cromakalim or a pharmaceutically acceptable salt of 4 mM, or at least 4 mM, and no more than 5 mM.

In certain other embodiments, an ocular formulation as described herein has a concentration of (lev)cromakalim or a pharmaceutically acceptable salt of 4.5 mM, or at least 4.5 mM, and no more than 5 mM.

In certain other embodiments, an ocular formulation as described herein has a concentration of (lev)cromakalim or a pharmaceutically acceptable salt of 5 mM, or at least 5 mM, and no more than 5 mM.

The present invention provides, in one aspect, an ocular topical formulation of (lev)cromakalim that has a concentration of (lev)cromakalim or a pharmaceutically acceptable salt thereof of at least 0.01, 0.05, 0.4, 0.5, 0.8, 0.9, 1, 1.5, 2, or 2.5, and typically not more than about 5 mM and is stable at ambient conditions for at least 5 months and comprises three or more components selected from the group of a triol or polyol (typically aliphatic, and more typically alkyl) (for example glycerin); a polyethoxylated furanose fatty acid ester (for example a polysorbate); a nonionic tri-block copolymer of a central hydrophobic chain of polyoxypropylene (poly(propylene oxide)) flanked by two hydrophilic chains of polyoxyethylene (poly(ethylene oxide)) (for example a poloxamer or Pluronic); an alkyl aryl polyol (for example tyloxapol); an ethoxylated glycerol ester (for example Kolliphor® EL or ELP, Cremophor, Kolliphor® RH 40 or Kolliphor® HS 15); polyoxylalkylene castor oil; carboxymethyl cellulose/CMC; hypromellose; a polymeric lactam (for example PVP); an oil in water polymeric emulsifier of a block copolymer of polyacrylic acid and a hydrophobic $C_{10}$-$C_{30}$ alkyl acrylate (for example, Premulen™ (which may be for example TR-1 or TR-2); and an ethoxylated alkylphenol (for example octoxynol-40); in an aqueous formulation with a pH from about 6 to 8 or 6.5 to 7.5.

The invention in another aspect is an ocular topical formulation of (lev)cromakalim that has a concentration of (lev)cromakalim or a pharmaceutically acceptable salt there of at least 0.01, 0.05, 0.4, 0.5, 0.8, 0.9, 1, 1.5, 2, or 2.5, and typically not more than about 5 mM and is stable at ambient conditions for at least 5 months and comprises three or more components selected from the group consisting of glycerin, polysorbate, poloxomer 407, Pluronic® F127, tyloxapol; Kolliphor® (which may be, for example, EL, ELP, RH or HS), polyoxyl-25 castor oil, carboxymethyl cellulose/CMC, hypromellose, PVP, Premulen™ (for example, TR-1 or TR-2), and octoxynol-40 in an aqueous solution; in an aqueous formulation with a pH from about 6 to 8, or 6.5 to 7.5.

In yet another embodiment, the invention is an aqueous ocular formulation that comprises, consists essentially of or consists of (lev)cromakalim or a pharmaceutically acceptable salt thereof, Kolliphor® (which may be, for example, EL, ELP, RH or HS), polysorbate (which may be, for example, 20, 40, 60 or 80), PVP (polyvinylpyrrolidone), poloxamer (which may be, for example, 407 or another variation), mannitol, water or phosphate buffer, and optionally benzalkonium chloride and optionally a pH adjusting agent; that has a concentration of (lev)cromakalim of at least 0.01, 0.05, 0.4, 0.5, 0.8, 0.9, 1, 1.5, 2, or 2.5, and typically not more than about 5 mM and is stable at ambient conditions for at least 5 months with a pH of 6-8, or 6.5-7.5.

Another aspect of the invention is an aqueous ocular formulation that comprises, consists essentially of or consists of (lev)cromakalim or a pharmaceutically acceptable salt thereof, glycerin, Kolliphor® (which may be, for example, EL, ELP, RH or HS), polysorbate (which may be, for example, 20, 40, 60 or 80), poloxamer (which may be, for example, 407 or another variation), hypromellose, mannitol, optionally benzalkonium chloride and optionally a pH adjusting agent; wherein the formulation satisfies illustrative aspects (i) and (ii) described herein; i.e., has a concentration of (lev)cromakalim of at least 0.01, 0.05, 0.4, 0.5, 0.8, 0.9, 1, 1.5, 2, or 2.5, and typically not more than about 5 mM and is stable at ambient conditions for at least 5 months and a pH of 6-8, or 6.5-7.5.

Further, the invention provides an aqueous ocular formulation that comprises, consists essentially of or consists of (lev)cromakalim or a pharmaceutically acceptable salt thereof, glycerin, Kolliphor® (which may be, for example, EL, ELP, RH or HS), polysorbate (which may be, for example, 20, 40, 60 or 80), poloxamer (which may be, for example, 407), PVP, mannitol, and optionally benzalkonium chloride and optionally a pH adjusting agent; wherein the formulation satisfies illustrative aspects (i) and (ii) described herein; i.e., has a concentration of (lev)cromakalim of at least 0.01, 0.05, 0.4, 0.5, 0.8, 0.9, 1, 1.5, 2, or 2.5, and typically not more than about 5 mM and is stable at ambient conditions for at least 5 months and a pH of 6-8, or 6.5-7.5.

In certain embodiments, the (lev)cromakalim formulation comprises a mixture of polysorbate 80, Kolliphor® (which may be, for example, EL, ELP, RH or HS), and PVP, with a concentration of (lev)cromakalim of at least 0.01, 0.05, 0.4, 0.5, 0.8, 0.9, 1, 1.5, 2, or 2.5, and typically not more than about 5 mM and is stable at ambient conditions for at least 5 months and a pH of 6-8, or 6.5-7.5.

In certain embodiments, the (lev)cromakalim formulation comprises a component mixture of Kolliphor® (for example Kolliphor® EL or ELP, Cremophor, Kolliphor® RH 40 or Kolliphor® HS 15), polysorbate 80, phosphate buffer, and poloxamer 407, with a concentration of (lev)cromakalim of at least 0.01, 0.05, 0.4, 0.5, 0.8, 0.9, 1, 1.5, 2, or 2.5, and typically not more than about 5 mM and is stable at ambient conditions for at least 5 months and a pH of 6-8, or 6.5-7.5.

In certain embodiments, the (lev)cromakalim formulation comprises a component mixture of Kolliphor® (for example Kolliphor® EL or ELP, Cremophor, Kolliphor® RH 40 or Kolliphor® HS 15) (for example Kolliphor® EL or ELP, Cremophor, Kolliphor® RH 40 or Kolliphor® HS 15), poysorbate 80, PVP, and phosphate buffer, with a concentration of (lev)cromakalim of at least 0.01, 0.05, 0.4, 0.5, 0.8, 0.9, 1, 1.5, 2, or 2.5, and typically not more than about 5 mM and is stable at ambient conditions for at least 5 months and a pH of 6-8, or 6.5-7.5.

In certain embodiments, the (lev)cromakalim formulation comprises a component mixture of Kolliphor® ELP, polysorbate 80, PVP, poloxamer 407, and PBS, with a concentration of (lev)cromakalim of at least 3.5 mM, and typically not more than 5 mM, and is stable at ambient conditions for at least 5 months and a pH of 6-8 or 6.5-7.5.

In certain embodiments, the (lev)cromakalim formulation comprises a component mixture of Kolliphor® (for example Kolliphor® EL or ELP, Cremophor, Kolliphor® RH 40 or Kolliphor® HS 15), polysorbate (for example, 20, 40, 60 or 80), PVP, poloxamer 407, and mannitol, with a concentration of (lev)cromakalim of at least 3.5 mM, and typically not more than 5 mM, and is stable at ambient conditions for at least 5 months and a pH of 6-8, or 6.5-7.5.

In certain embodiments, the (lev)cromakalim formulation comprises a component mixture of glycerin, Kolliphor® (for example Kolliphor® EL or ELP, Cremophor, Kolliphor® RH 40 or Kolliphor® HS 15), polysorbate (for example, 20, 40, 60 or 80), poloxamer (for example 407), hypromellose, and PBS, and a concentration of (lev)cromakalim of at 0.01, 0.05, 0.4, 0.5, 0.8, 0.9, 1, 1.5, 2, or 2.5, and typically not more than about 5 mM and is stable at ambient conditions for at least 5 months and a pH of 6-8, or 6.5-7.5.

In certain embodiments, the (lev)cromakalim formulation comprises a component mixture of Kolliphor® (for example Kolliphor® EL or ELP, Cremophor, Kolliphor® RH 40 or Kolliphor® HS 15), polysorbate (for example, 20, 40, 60 or 80), PVP, poloxamer 407, phosphate buffer, mannitol, and BAK, a concentration of (lev)cromakalim of at least 0.01, 0.05, 0.4, 0.5, 0.8, 0.9, 1, 1.5, 2, or 2.5, and typically not more than about 5 mM and is stable at ambient conditions for at least 5 months and a pH of 6-8, or 6.5-7.5.

In certain embodiments, the (lev)cromakalim formulation comprises a component mixture of Kolliphor® (for example Kolliphor® EL or ELP, Cremophor, Kolliphor® RH 40 or Kolliphor® HS 15), polysorbate (for example, 20, 40, 60 or 80), PVP, poloxamer (for example 407), phosphate buffer, and mannitol, a concentration of (lev)cromakalim of at least 3.5 mM, and typically not more than 5 mM and is stable at ambient conditions for at least 5 months and a pH of 6-8, or 6.5-7.5.

In certain embodiments, the (lev)cromakalim formulation comprises a component mixture of glycerin, Kolliphor® (for example Kolliphor® EL or ELP, Cremophor, Kolliphor® RH 40 or Kolliphor® HS 15), polysorbate (for example, 20, 40, 60 and 80), poloxamer (for example 407), mannitol, hypromellose, and phosphate buffer, a concentration of (lev)cromakalim of at least 3.5, and typically not more than 5 mM and is stable at ambient conditions for at least 5 months and a pH of 6-8, or 6.5-7.5.

In certain embodiments, the (lev)cromakalim formulation comprises a component mixture of glycerin, Kolliphor® (for example Kolliphor® EL or ELP, Cremophor, Kolliphor® RH 40 or Kolliphor® HS 15), polysorbate (which may be 20, 40, 60 or 80), poloxamer 407, mannitol, hypromellose, BAK, and phosphate buffer, a concentration of (lev)cromakalim of at least 0.01, 0.05, 0.4, 0.5, 0.8, 0.9, 1, 1.5, 2, or 2.5, and typically not more than about 5 mM and is stable at ambient conditions for at least 5 months and a pH of 6-8, or 6.5-7.5.

In certain embodiments, the topical administration drops are administered through a single use (unit dose) pharmaceutical packaging. In certain embodiments, the unit dose packaging contains at least about 100 μL to about 500 μL, and more typically about 300 μL of the ocular formulation. In certain embodiments, the delivery volume per drop of the formulation delivered through the unit dose packaging is at least about 10 μL to about 50 μL, and more typically about 30 μL per eye. In certain specific embodiments, the concentration of the (lev)cromakalim in the unit dose packaging is at least about 0.05 mM, 0.5 mM, 1 mM, 1.5 mM, or 2.5 mM, and typically not more than 5 mM. In certain specific embodiments, five of the unit dose dropper bottles are dispensed in a single foil packaging. In certain embodiments the concentration of (lev)cromakalim is between 0.5 and 2.5 mM. In certain embodiments the concentration of (lev) cromakalim is between 0.05 and 0.5 mM, between 0.5 and 1.5 mM, or between 1 and 2.5 mM.

In certain non-limiting illustrative embodiments, the (lev) cromakalim formulation for topical administration is provided in strengths of 0.015%, 0.030%, and 0.075% containing 0.15 mg/mL, 0.30 mg/mL, and 0.75 mg/mL of (lev) cromakalim respectively. As described in Example 13, levcromakalim ophthalmic solution is provided in a low-density polyethylene blow fill seal (BFS) single use unit dose container. Examples include but are not limited to:

- 0.015% (0.15 mg/mL) BFS unit dose: A clear, colorless 300 L unit dose BFS of (lev)cromakalim formulation ophthalmic solution at a concentration of 0.015% (0.15 mg/mL) in an iso-osmotic phosphate buffered solution at pH 6.5.
- 0.030% (0.30 mg/mL) BFS unit dose: A clear, colorless 300 L unit dose BFS of (lev)cromakalim formulation ophthalmic solution at a concentration of 0.030% (0.30 mg/mL) in an iso-osmotic phosphate buffered solution at pH 6.5.
- 0.075% (0.75 mg/mL) BFS unit dose: A clear, colorless 300 L unit dose BFS of (lev)cromakalim formulation ophthalmic solution at a concentration of 0.075% (0.75 mg/mL) in an iso-osmotic phosphate buffered solution at pH 6.5.

In certain embodiments the (lev)cromakalim formulation is a clear aqueous micellar solution.

In certain embodiments the (lev)cromakalim formulation is a clear aqueous solution.

In certain embodiments, the (lev)cromakalim formulation does not include an oil as defined below.

In certain embodiments the (lev)cromakalim formulation is not an emulsion.

In certain embodiments the (lev)cromakalim formulation is not a gel.

In certain embodiments the (lev)cromakalim formulation is not a topical gel.

In certain embodiments the (lev)cromakalim formulation is a clear solution.

In certain embodiments the (lev)cromakalim formulation is a micellar solution.

In certain embodiments the (lev)cromakalim formulation is a nanomicellar solution.

In certain embodiments the (lev)cromakalim formulation has a percent transmittance of greater than 85% when tested with a UV-Vis spectrophotometer.

In certain embodiments the (lev)cromakalim formulation has a percent transmittance of greater than 90% when tested with a UV-Vis spectrophotometer.

In certain embodiments the (lev)cromakalim formulation has a percent transmittance of greater than 95% when tested with a UV-Vis spectrophotometer.

In certain embodiments the (lev)cromakalim formulation has a percent transmittance of greater than 98% when tested with a UV-Vis spectrophotometer.

In certain embodiments the (lev)cromakalim formulation does not contain a long-chain triglyceride.

In certain embodiments the (lev)cromakalim formulation does not contain a medium-chain triglyceride.

In certain embodiments the (lev)cromakalim formulation does not contain a short-chain triglyceride.

In certain embodiments, the (lev)cromakalim formulation does not include an oil as specifically defined below.

I. Definitions

A "patient" or "host" or "subject", as used herein, is typically a human and the method is for human therapy. In appropriate circumstances, the scope, alternatively may include a non-human animal in need of treatment or prevention of any of the disorders as specifically described herein, for example, a mammal, primate (other than human), cow, sheep, goat, horse, dog, cat, or the like.

Oil as an Optionally Excluded Component

In certain embodiments the (lev)cromakalim formulation does not contain an oil. The term "oil" when used as an excluded component to the topical formulation described herein refers to a liquid organic compound that is primarily a hydrocarbon and can be used to prepare a water in oil emulsion, such as a long-chain triglyceride (including but not limited to castor oil, soybean oil, corn oil, flaxseed oil, cottonseed oil, coconut oil canola oil, argan oil, palm oil, peanut oil, and other vegetable oils), and/or medium-chain triglycerides (including but not limited to caprylic/capric triglycerides (e.g. miglyol 812)), and/or mono- and diglycerides (including but not limited to caprylic/capric mono- and di-glycerides, e.g. imwitor 742). The term oil when used as an optionally excluded component does not include any of the optionally included components described below (in other words, the formulation components described below are excluded from the definition of oil herein).

Polysorbate

Polysorbates as used herein are a class of emulsifiers derived from esterification of ethoxylated sorbitan with fatty acids. Polysorbates as used herein are oily liquids used to solubilize oils in water-based products. Examples of polysorbates include polysorbate 20, polysorbate 40, polysorbate 60, and polysorbate 80. Common brand names of polysorbates are Tween, Scattics, Alkest, and Canarcel. The numeral after polysorbate refers to the major fatty acid of the molecule, e.g., monolaurate is indicated by 20, monopalmitate is indicated by 40, monostearate by 60, and monooleate by 80. An example of a polysorbate component, polysorbate 80 (polyoxyethylene (20) sorbitan monooleate) as described herein is a viscous, non-ionic hydrophilic surfactant derived from polyethoxylated sorbitan and oleic acid with an average molecular weight of 1310 Da, and HLB value of 15.

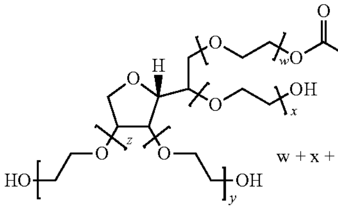

w + x + y + z = 20

It is an emulsifier as it contains polyoxyethylene hydrophilic component and polysorbate lipophilic component. Polysorbate 80 shows no carcinogenicity and genotoxicity as it shows no adverse effects at the dose of 2500 mg/kg/day. In certain nonlimiting embodiments, polysorbate 80 is used up to about 1% w/v concentration in ophthalmic solution.

Kolliphor® or Cremophor®

Kolliphor® or Cremophor® (BASF) as used herein is polyoxyl-ethylated castor oil (ethoxylated glycerol ester) made from castor oil and ethylene oxide where fatty acid esters of glycerol represent the hydrophobic portion, and the polyethylene glycol represent the hydrophilic portion. It is used as a surfactant, emulsifier and solubilizer (HLB value=12 to 14) in drug formulations because it can emulsify and solubilize oils and water-insoluble agents as it is fully soluble in aqueous formulations. An example of ethoxylated glycerol ester, Kolliphor® ELP (Cremophor® ELP or polyoxyl-35-castor oil) is a non-ionic polyethoxylated detergent made by reacting castor oil and ethylene oxide in a molar ratio of 1:35.

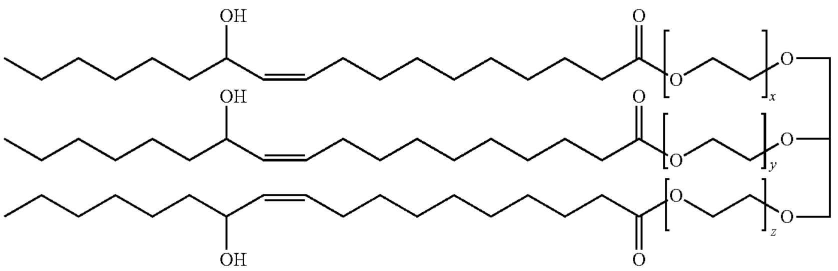

Kolliphor® ELP is more viscous than Kolliphor® EL (Cremophor® EL). It forms a clear aqueous solution in water, and dissolves in common organic solvents as it contains free polyethylene glycols and ethoxylated glycols as hydrophilic components, and glycerol polyethylene glycol ricinoleate and fatty esters of polyethylene glycol as lipophilic components. It is used as a purified solubilizer for paclitaxel formulations. In certain non-limiting illustrative embodiments, Kolliphor® ELP is used up to about 5% w/v concentration.

Polymeric Lactam

A lactam as used herein is a cyclic amide derived from amino alkanoic acid. The common five types of lactams are named based on rings size as α-lactam (3-atom rings), β-lactam (4-atom rings), γ-lactam (5-atom rings), δ-lactam (6-atom rings), and ε-lactam (7-atom rings). Polymeric lactam can be synthesized in a range of molecular weights and viscosities from a lactam-vinyl monomer. For example, PVP (polyvinylpyrrolidone, povidone or polyvidone) derived from N-vinylpyrrolidone is a bio-degradable, water-soluble polymer. It is one of the most widely used components in pharmaceutical compositions as it exhibits excellent solubility in solvents of different polarities; and stabilizes suspensions and emulsions.

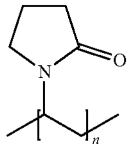

| Example PVP type | Molecular weight (kDa) |
|---|---|
| K12 | 3.1-5.7 |
| K17 | 7.9-10.8 |
| K25 | 23-32 |
| K30 | 35-51 |
| K90 | 900-1300 |

It contributes to solubility due to its hydrophilic components as it binds to polar molecules such as phenolic compounds via hydrogen bonding. It is used as a thickening agent because its viscosity is tunable due to its availability at a range of molecular weights ($2.5\times10^3$ to $2.5\times10^6$ Da) further described in the table above. It is used in ophthalmic solutions (eye drops or lens packaging solutions) as it acts as a lubricant or wetting agent. In certain non-limiting illustrative embodiments, PVP K-30 is used up to about 2% w/v.

Poloxamers

Poloxamers as used herein are nonionic triblock copolymers composed of a central hydrophobic chain of polyoxypropylene flanked by two hydrophilic chains of polyoxyethylene. Pluronic as described herein is a poloxamer that consists of hydrophilic poly(ethylene oxide) (PEO) and hydrophobic poly(propylene oxide) (PPO), arranged in an A-B-A triblock structure, thus giving PEO-PPO-PEO. An important characteristic of poloxamer solutions is their temperature dependent self-assembling and thermo-gelling behavior. Concentrated aqueous solutions of poloxamers are liquid at low temperature and form a gel at higher temperature in a reversible process. The transitions that occur in these systems depend on the molecular weight and hydrophilic/hydrophobic molar ratio. They can be used to increase the water solubility of hydrophobic, oily substances or otherwise increase the miscibility of two substances with different hydrophobicities.

An example of a poloxamer is poloxamer 407 that is a hydrophilic non-ionic surfactant which is a polyoxyethylene polymer. Poloxamer 407 can be used up to about 0.1% w/v concentration in ophthalmic solution (drops).

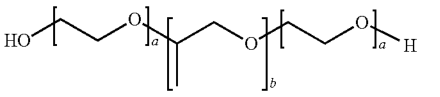

$a_{avg} = 101$
$b_{avg} = 56$

It is a triblock copolymer consisting of polypropylene glycol (PPG) as a central lipophilic block with an average length of 56 repeating units, which is flanked on two sides by hydrophilic polyethylene glycol (PEG) blocks with an average length of 101 repeating units. It is listed as a component in the inactive ingredient database (IID) and is approved by FDA. It is used as a hydrophilic non-ionic surfactant to dissolve oily substances in aqueous media and has an HLB value of >18. It has been used as an emulsifier and solubilizer in ophthalmic cleaning solutions at concentrations of up to 0.2%. Ophthalmic gel forming poloxamer 407 and hydroxypropyl methyl cellulose are used for ocular delivery of chloramphenicole.

Polyols

A polyol as used herein is an aliphatic, typically alkyl, organic compound containing multiple hydroxyl groups (—OH). Polyols containing two, three and four hydroxyl groups are diols, triols, and tetrols, and can be used in the formulation of the present invention.

A triol as described herein is an alkyl polyol containing three hydroxyl groups. Glycerol (e.g., glycerin) is a viscous, non-toxic triol solvent containing hydrophilic components. It is derived through hydrolysis, saponification with sodium hydroxide, or transesterification of triglycerides (esters of glycerol with long-chain carboxylic acid) extracted from plant and animals.

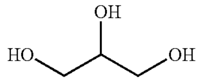

It is miscible in water or alcohol-based solvents and can solubilize emulsions and surfactants due to the polar interactions. Due to its high viscosity while possessing alcohol like solvent properties, it is used as a bulking agent, and osmotic diuretic ophthalmic agent.

A sugar alcohol as described herein is a polyol derived from the hydrogenation of a sugar and contains one hydroxyl group (—OH) attached to each carbon atom. Sugar alcohols have the general formula $HOCH_2(CHOH)_nCH_2OH$ and exist in differing chain lengths, most commonly five- or six-carbon chains as they are derived from pentoses (five-carbon sugars) and hexoses (six-carbon sugars), respectively. They typically can be differentiated by the relative orientation (stereochemistry) of these —OH groups. For example, mannitol and sorbitol only differ in the orientation of hydroxyl group on carbon 2. Mannitol, as described herein, is a type of sugar alcohol derived from reduction of mannose, which produces sorbitol, a 2'-OH isomer of mannitol as the other product. In certain non-limiting illustrative embodiments, mannitol can be used up to about 4.6% w/v concentration in ophthalmic solution.

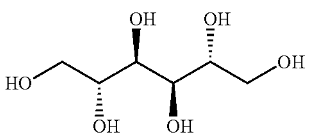 [SMILES: OC[C@@H](O)[C@@H](O)[C@H](O)[C@H](O)CO]

Sugar alcohols are inert and non-hygroscopic. They are used as an additive and a bulking agent (vehicle) for lyophilized formulations. Other sugar alcohols include but are not limited to erythritol, ethylene glycol, glycerol, threitol, arabitol, xylitol, ribitol, sorbitol, galactitol, fucitol, iditol, inositol, volemitol, maltitol and lactitol.

Polymeric Alkyl or Aryl Polyols

Polymeric alkyl or aryl polyols as used herein are liquid polymers of alkyl or aryl alcohol prepared by reaction of alkyl or aryl alcohol with aldehydes, e.g., formaldehyde.

Tyloxapol is a non-ionic liquid polymer of alkyl aryl polyether alcohol. It is formed by reaction of 4-(1,1,3,3-tetramethylbutyl) phenol with formaldehyde, followed by reaction to oxirane.

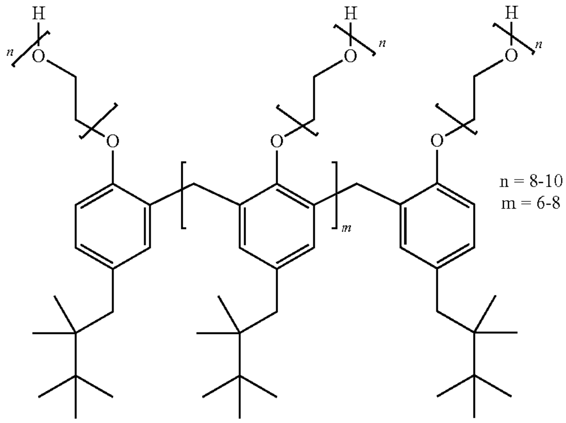

n = 8-10
m = 6-8

A polyether alcohol hydrophilic component consists of hydrogen bond donors and acceptors, and the lipophilic alkyl component can emulsify hydrophobic components in aqueous formulations. It is used as a surfactant in ophthalmic formulations to balance hydrophilic-lipophilic mixtures as it has an HLB of 13. WO1998025620A1 describes the use of tyloxapol in manufacturing ophthalmic suspensions.

Hydroxyalkyl Cellulose

Hydroxyalkyl cellulose as described herein is a hydroxyalkyl ether of cellulose prepared by treating cellulose with sodium hydroxide and reacting with alkylene oxide. It is used as a water-binder and a thickening agent in pharmaceutical compositions to facilitate hydrophilization. Non-limiting examples of hydroxyalkyl celluloses include hydroxymethylcellulose (HMC), hydroxyethyl cellulose (HEC), and hydroxypropyl methylcellulose (HPMC or hypromellose).

Hypromellose (hydroxypropyl methylcellulose) is a non-ionic, partly O-methylated and O-(2-hydroxypropylated) cellulose ether derived semisynthetic polymer containing β-linked D-glucose.

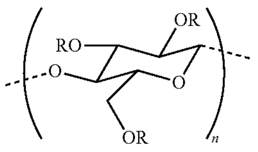

R = H or
$CH_3$ or
$CH_2CH(OH)CH_3$

It is manufactured by reacting alkali cellulose, methyl chloride, and propylene oxide. It is available in various substitution ratios and molecular weight grades, and its HLB value ranges from 10 to 11. It is used as an emulsifier, hydrophilic thickening agent, and stabilizer due to film-foaming ability, biocompatibility, and biodegradability. In ophthalmic solutions it also acts as a lubricant.

Benzalkonium Chloride (BAK)

Benzalkonium chloride as used herein is a cationic surfactant containing a quaternary ammonium as a cationic head group. It is composed of alkyldimethylbenzylammonium chlorides, with paraffinic chains of 8-18 carbons as lipophilic alkyl residues.

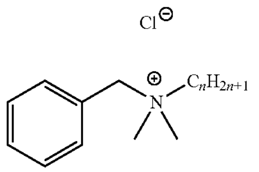

n = 8, 10, 12, 14, 16, 18

It can be used to dissolve lipophilic components in aqueous formulations at neutral to slightly alkaline pH, as the aqueous solution containing BAK have low surface tension exhibiting emulsifying properties.

Carbomer Copolymer A and B

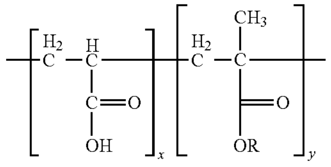

R = logn-chain alkyl

Carbomer Copolymer Type A, as used herein for example Premulen® TR-2 is a copolymer of a hydrophilic acrylic acid and hydrophobic alkyl acrylate co-monomer. Specifically, it is a high molecular weight copolymer of acrylic acid and hydrophobic $C_{10}$-$C_{30}$ alkyl acrylate crosslinked with pentaerythritol. It is a non-ethoxylated polymer for mild oil in water emulsions. Carbomer Copolymer A (Premulen® TR-2) can generate low-viscosity emulsions and can stabilize 60% oil by weight as it contains higher levels of hydrophobic groups. It forms polyethylene glycol free formulations and resulting formulations do not require HLB calculation. Carbomer Copolymer A used in Restasis. (For information on Restasis. See below).

Carbomer Copolymer B, as used herein, for example Premulen® TR-1 has a similar structure to Carbomer Copolymer A, however, it contains lower levels of hydrophobic groups compared to Carbomer Copolymer A. It can generate high viscosity emulsions and formulate up to 20% oil by weight in pH range of 3-11, and 30% oil by weight in pH range 4-5.5.

A solubilizer or solubilizing agent is a surfactant that increases the solubility of one agent in another.

An emulsifier/emulsifying agent is an agent that helps other agents mix and prevent separation. Water in oil (w/o) emulsifiers keep water drops packed in oil, while oil in water (o/w) emulsifiers keep oil drops packed in water.

A wetting agent is a surface-active molecule capable of reducing surface tension of water.

An antifoaming agent is a molecule which reduces or hinders foam (materials formed by trapping gas pockets in liquid) formation.

It should be realized that whenever the commercial name of a formulation component is used, it is exemplary only and not intended to limit the scope of the invention. Non-limiting examples of the chemical names or chemical classes that can be directly substituted for a commercial product name used are provided above and include but are not limited to: a triol or polyol (typically aliphatic, and more typically alkyl) (for example glycerin); a polyethoxylated furanose fatty acid ester (for example a polysorbate); a nonionic tri-block copolymer of a central hydrophobic chain of polyoxypropylene (poly(propylene oxide)) flanked by two hydrophilic chains of polyoxyethylene (poly(ethylene oxide)) (for example a poloxamer or Pluronic); an alkyl aryl polyol (for example tyloxapol); an ethoxylated glycerol ester (for example Kolliphor® EL or ELP, Cremophor®, Kolliphor® RH 40 or Kolliphor® HS 15); polyoxyalkylene castor oil; carboxymethyl cellulose/CMC; hypromellose; a polymeric lactam (for example PVP); an oil in water polymeric emulsifier of a block copolymer of polyacrylic acid and a hydrophobic $C_{10}$-$C_{30}$ alkyl acrylate (for example, Premulen™ such as TR-1 and TR-2); and an ethoxylated alkylphenol (for example octoxynol-40).

In certain aspects a "micellar solution" is a solution which comprises a dispersion of micelles.

In certain aspects a "micelle" is an aggregate of amphipathic lipid molecules dispersed in a liquid.

In certain aspects a "nanomicellar solution" is a micellar solution containing micelles of less than 100 nm in diameter.

II. Pharmaceutical Compositions and Dosage Forms for Ocular Delivery

The aqueous pharmaceutically acceptable ocular topical formulations with an effective amount of (lev)cromakalim or a pharmaceutically acceptable salt thereof can be administered to treat any ocular disorder that can be treated with (lev)cromakalim, including any of the disorders described herein, including but not limited to decreasing intraocular pressure in the eye of a host in need thereof, treating normal tension glaucoma, or for other indications that can be treated with (lev)cromakalim as described herein.

Ocular formulations of (lev)cromakalim as described herein, are stable at ambient conditions for at least 5, 6, or 7 months or more and can achieve effective concentrations without the use of a "universal organic solvent" such as DMSO or other excipients that are not pharmaceutically acceptable in the range needed for solubilization. In fact, formulations of (lev)cromakalim in Examples below show improved solubility to that of mixtures of DMSO and Cremophor® (i.e., Kolliphor®) formulations of (lev)cromakalim. Improved solubility of the ocular formulations described herein translate to improved bioavailability and efficacy as indicated in studies shown in FIG. 3, which demonstrates the intraocular pressure (IOP) at various concentrations of (lev)cromakalim formulated and compares it to the formulations at identical concentrations in DMSO and Cremophor®. This data shows improved ability of (lev) cromakalim formulations described herein (~33% IOP reduction) compared to DMSO and Cremophor @formulation (~23% IOP reduction).

Nonlimiting illustrative examples of aqueous formulations of (lev)cromakalim according to the present invention that exhibit a concentration of the (lev)cromakalim above 1 mg/mL include, but are not limited to the following:

Example 2a, wherein the ocular formulation comprises levcromakalim, glycerin, Kolliphor® ELP, polysorbate 80, poloxamer 407, hypromellose, mannitol, and BAK. For example, a formulation of Formula 2a with this component mixture exhibited the levcromakalim concentration of 1.4 mg/mL or 4.7 mM.

Example 2b, wherein the ocular formulation comprises levcromakalim, Kolliphor® RH 40, octoxynol-40, and Premulen™ TR-2. For example, a formulation of Formula 2b with this component mixture exhibited the levcromakalim concentration of 1.2 mg/mL or 4.3 mM.

Example 2c, wherein the ocular formulation comprises leveromakalim, Kolliphor® RH 40, Kolliphor® HS 15, and PVP. For example, a formulation of Formula 2c with this component mixture exhibited the leveromakalim concentration of 1.2 mg/mL or 4.1 mM.

Example 2d, wherein the ocular formulation comprises levcromakalim, glycerin, Kolliphor® ELP, polysorbate 80, and hypromellose. For example, a formulation of Formula 2d with this component mixture exhibited the levcromakalim concentration of 1.3 mg/mL or 4.6 mM.

Example 2e, wherein the ocular formulation comprises levcromakalim, Kolliphor® ELP, polysorbate 80, and PVP. For example, a formulation of Formula 2e with this component mixture exhibited the levcromakalim concentration of 1.1 mg/mL or 4 mM.

Example 2f, wherein the ocular formulation comprises levcromakalim, glycerin, Kolliphor® ELP, polysorbate 80, poloxamer 407, and hypromellose. For example, a formulation of Formula 2f with this component mixture exhibited the levcromakalim concentration of 1.3 mg/mL or 4.4 mM.

Example 2g, wherein the ocular formulation comprises levcromakalim, glycerin, Kolliphor® RH 40, Premulen™ TR-2, and PVP. For example, a formulation of Formula 2g with this component mixture exhibited the levcromakalim concentration of 1 mg/mL or 3.7 mM.

Example 2h, wherein the ocular formulation comprises levcromakalim, Kolliphor® HS 15, Premulen™ TR-2, polysorbate 80, octoxynol-40, and poloxamer 407. For example, a formulation of Formula 2 h with this component mixture exhibited the levcromakalim concentration of 1.3 mg/mL or 4.4 mM.

Example 2i, wherein the ocular formulation comprises levcromakalim, glycerin, Kolliphor® ELP, polysorbate 80, PVP, mannitol, octoxynol-40, and poloxamer 407. For example, a formulation of Formula 2i with this component mixture exhibited the levcromakalim concentration of 1.2 mg/mL or 4.3 mM.

Example 2j, wherein the ocular formulation comprises levcromakalim, glycerin, Kolliphor® ELP, polysorbate 80, poloxamer 407, hypromellose, mannitol, and BAK. For example, a formulation of Formula 2j with this component mixture exhibited the levcromakalim concentration of 1.3 mg/mL or 4.6 mM.

Example 3a, wherein the ocular formulation comprises leveromakalim, polysorbate 80, Kolliphor® ELP, and PVP. For example, a formulation of Formula 3a with this component mixture exhibited the levcromakalim concentration of 1.7 mg/mL or 5.8 mM.

Example 3b, wherein the ocular formulation comprises levcromakalim, Kolliphor® ELP, polysorbate 80, and poloxamer 407. For example, a formulation of Formula 3b with this component mixture exhibited the levcromakalim concentration of 2.1 mg/mL or 7.3 mM.

Example 3c, wherein the ocular formulation comprises levcromakalim, Kolliphor® ELP, polysorbate 80, PVP, and poloxamer 407. For example, a formulation of Formula 3c with this component mixture exhibited the levcromakalim concentration of 1.8 mg/mL or 6.4 mM.

Example 3d, wherein the ocular formulation comprises levcromakalim, Kolliphor® ELP, polysorbate 80, PVP, poloxamer 407, and mannitol. For example, a formulation of Formula 3d with this component mixture exhibited the levcromakalim concentration of 1.6 mg/mL or 5.5 mM.

Example 3e, wherein the ocular formulation comprises levcromakalim, glycerin, Kolliphor® ELP, polysorbate 80, poloxamer 407, and hypromellose. For example, a formulation of Formula 3e with this component mixture exhibited the levcromakalim concentration of 1.9 mg/mL or 6.5 mM.

Example 3f, wherein the ocular formulation comprises levcromakalim, Kolliphor® ELP, polysorbate 80, PVP, poloxamer 407, mannitol; and BAK. For example, a formulation of Formula 3f with this component mixture exhibited the levcromakalim concentration of 1.5 mg/mL or 5.4 mM.

Example 3g, wherein the ocular formulation comprises levcromakalim, Kolliphor® ELP, polysorbate 80, PVP, poloxamer 407, and mannitol. For example, a formulation of Formula 3g with this component mixture exhibited the levcromakalim concentration of 1.6 mg/mL or 5.7 mM.

Example 3h, wherein the ocular formulation comprises levcromakalim, glycerin, Kolliphor® ELP, polysorbate 80, poloxamer 407, mannitol, and hypromellose. For example, a formulation of Formula 3 h with this component mixture exhibited the levcromakalim concentration of 1.7 mg/mL or 5.9 mM.

In certain embodiments, the ocular formulation of (lev) cromakalim or a pharmaceutically acceptable salt is formed as a solution or an emulsion at a concentration of for example at least about 0.01, 0.05, 1, 1.1, 1.2, 1.3, or 1.4, and typically not more than about 1.5 mg/mL.

In certain embodiments, the ocular formulation of (lev) cromakalim or its pharmaceutically acceptable salt is formed as a solution or an emulsion at a concentration of for example at least about 0.05, 0.5, 1, 1.5, 2, 2.5, 3, 3.5, 4, or 4.5 mM, and typically not more than about 5 mM.

The average topical drop tends to range from 20 microliters to 50 microliters but can be larger or smaller depending on viscosity and the size of the dropper. An average drop may in certain embodiments be approximately in the range of 30 microliters+/−25%. In a normal dosage, the patient is asked to administer one drop per eye once, twice, three times or four times a day.

The ocular formulation of (lev)cromakalim described herein can be provided in any dosage strength that achieves the desired results. In certain illustrative non-limiting embodiments, the pharmaceutical composition is provided in one drop to the eye in a manner that administers a range of from about 0.0005 to about 0.001 mg, from about 0.001 mg to about 0.005 mg, from about 0.005 mg to about 0.01 mg; from about 0.01 mg to about 0.04 mg, or from about 0.04 mg to about 0.09 mg of a compound of the ocular formulation of (lev)cromakalim thereof. In certain embodiments, the dosage form has at least about 0.001 mg, 0.005 mg, 0.01 mg, 0.02 mg, 0.025 mg, or 0.05 mg of active compound or its salt.

A suitable pH active component such as a buffering agent or pH-adjusting agent used in the pharmaceutical composition according to the invention include but are not limited to acetate, borate, carbonate, citrate, and phosphate buffers, including disodium phosphate (sodium phosphate dibasic), monosodium phosphate (sodium phosphate monobasic), boric acid, sodium borate, sodium citrate, hydrochloric acid, sodium hydroxide.

In certain embodiments, the ocular formulation of (lev) cromakalim has a pH approximately between 6 and 8 or between 6.5 and 7.5. In certain embodiments, the formulation comprises a citrate buffer at a pH around 6.5 to 7. In alternate embodiments, the formulation comprises a phosphate buffer at a pH around 6.5 to 7. Suitable osmotic active components used in the pharmaceutical composition according to the invention include but are not limited to sodium chloride, mannitol, and glycerol.

Non-limiting examples of buffers, with or without additional components or other additives, that can be used as a pharmaceutically acceptable formulation for an appropriate indication as described herein include, for example (with illustrative, but not limiting concentrations and pH), acetate buffer (0.1 M, pH 5.0); acetate buffer (pH 3.6 to 5.6); BES-buffered saline (2×) (0.05 M, pH 6.95); bicine (1 M, pH 8.26); CAPS (1 M, pH 10.4); CHES (1 M, pH 9.5); citrate buffer (0.1 M, pH 6.0); citrate-phosphate buffer (0.15 M, pH 5.0); citrate buffer (pH 3.0 to 6.2); carbonate-bicarbonate buffer (pH 9.2 to 10.6); diethanolamine (1 M, pH 9.8); EBSS (magnesium, calcium, phenol red) (pH 7.0); glycine-HCl buffer (0.1 M, pH 3.0); glycine-sodium hydroxide buffer (0.08 M, pH 10); HBSS (Hank's Balanced Salt Solution); HEPPSO (1 M, pH 7.85); HHBS (Hank's Buffer with Hepes); hydrochloric acid-potassium chloride buffer (0.1 M, pH 2.0); imidazole-HCl buffer (0.05 M, pH 7.0); MES (0.5 M, pH 6); MOPS buffer (10×) (0.2 M, pH 7); PBS (phosphate buffered saline) (1×, pH 7.4)); sodium borate buffer (1 M, pH 8.5); TAE (1 M, pH 8.6); TAE buffer (50×) (0.04 M, pH 8.5); TBS (1 M, pH 7.4); TE buffer 10×; tricine (1 M, pH 8.05); tris buffer (1 M, pH 7.2); phosphate buffer (pH 5.8 to 8.0); potassium phosphate (pH 5.8 to 8.0); and, Trizma® buffer (pH 7.0 to 9.2).

In certain embodiments, levcromakalim can be administered in an ocular formulation as a salt. Pharmaceutically acceptable salts of levcromakalim include but are not limited to:

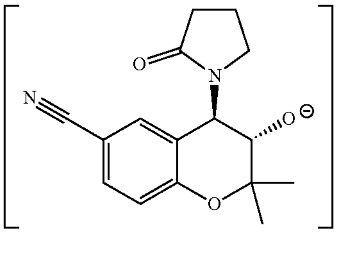

$X^{\oplus}$

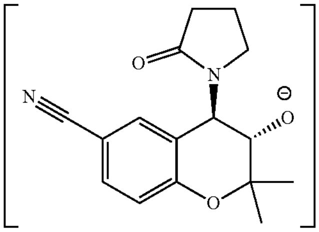

$Z^{\oplus}$

-continued

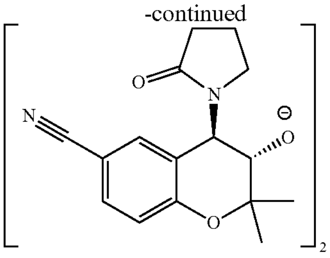

$M^{2+}$ wherein $X^+$ and $M^{2+}$ can be any pharmaceutically acceptable cation that achieves the desired results and $Z^+$ represents a mixed salt of $X^+$.

In certain embodiments, the cation is selected from sodium, potassium, aluminum, calcium, magnesium, lithium, iron, zinc, arginine, chloroprocaine, choline, diethanolamine, ethanolamine, lysine, histidine, meglumine, procaine, hydroxyethyl pyrrolidine, ammonium, tetrapropylammonium, tetrabutylphosphonium, methyldiethanamine, and triethylamine.

In certain embodiments, $X^+$ is $Na^+$ or $K^+$. In certain embodiments, $X^+$ is $Li^+$. In certain embodiments, $X^+$ is $Cs^+$. In certain embodiments, $X^+$ is an ammonium ion with a net positive charge of one. Non-limiting examples of ammonium ions with a net positive charge of one include:

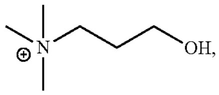, 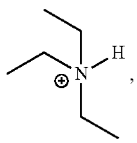, 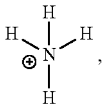, 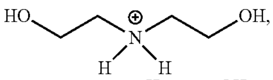, 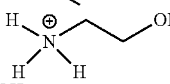, and 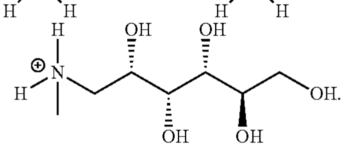.

In alternative embodiments, the ammonium ion with a net positive charge of one has the formula below:

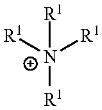

wherein $R^1$ is $C_1$-$C_6$alkyl, for example, but not limited to, methyl, ethyl, propyl, isopropyl, butyl, tbutyl, sec-butyl, isobutyl, $-CH_2C(CH_3)_3$, $-CH(CH_2CH_3)_2$, and $-CH_2CH(CH_2CH_3)_2$, cyclopropyl, $CH_2$-cyclopropyl, cyclobutyl, and $CH_2$-cyclobutyl, or aryl, for example, phenyl or napthyl wherein the $C_1$-$C_6$alkyl or aryl can be optionally substituted, for example with a hydroxyl group. In certain embodiments, the ammonium ion is

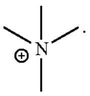.

$M^{2+}$, for example, may be, but is not limited to an alkaline earth metal cation (magnesium, calcium, or strontium), a metal cation with an oxidation state of +2 (for example, zinc or iron), or an ammonium ion with a net positive charge of two (for example, benzathine, hexamethyl diammonium, and ethylenediamine). In certain embodiments, $M^{2+}$ is $Mg^{2+}$. In certain embodiments, $M^{2+}$ is $Ca^{2+}$. In certain embodiments, $M^{2+}$ is $Sr^{2+}$. In certain embodiments, $M^{2+}$ is $Zn^{2+}$. In certain embodiments, $M^{2+}$ is $Fe^{2+}$. In certain embodiments, $M^{2+}$ is an ammonium ion with a net positive charge of two. Non-limiting examples of ammonium ions with a net positive charge of two include:

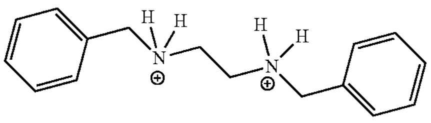

,

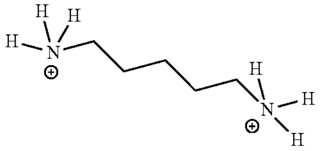

and

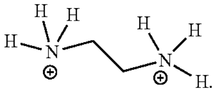

In alternative embodiments, the ammonium ion with a net positive charge of two has the formula below:

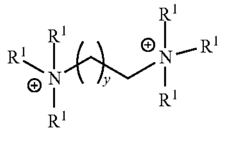

wherein $R^1$ is $C_1$-$C_6$alkyl, for example, but not limited to, methyl, ethyl, propyl, isopropyl, butyl, t-butyl, sec-butyl, isobutyl, $-CH_2C(CH_3)_3$, $-CH(CH_2CH_3)_2$, and $-CH_2CH(CH_2CH_3)_2$, cyclopropyl, $CH_2$-cyclopropyl, cyclobutyl, and $CH_2$-cyclobutyl, or aryl, for example, phenyl or napthyl wherein the $C_1$-$C_6$alkyl or aryl can be optionally substituted, for example with a hydroxyl group; and, y is an integer selected from 1, 2, 3, 4, 5, 6, 7, and 8.

III. Method of Administration

Ocular formulations of (lev)cromakalim or its pharmaceutically acceptable salt of the present invention described herein can be administered in an effective amount to a host, typically a human, in need thereof for any of the indications described herein. These immediate release formulations are administered as a pharmaceutical composition that includes an effective amount for a host, typically a human, in need of such treatment. Thus, disclosure provides pharmaceutical compositions comprising an effective amount of ocular formulation of (lev)cromakalim. The pharmaceutical composition may contain a compound or salt thereof as the only active agent, or, as described in detail herein, the compound or salt thereof and at least one additional active agent in a formulation.

The exact amount and dosage of the active compound in the ocular formulation described herein to be delivered to the host, typically a human, in need thereof will be determined by the health care provider to achieve the desired clinical benefit.

In certain embodiments, ocular formulation of levcromakalim thereof, including levcromakalim, is administered for at least about one day, two days, three days, four days, five days, six days, seven days, eight days, nine days, ten days, two weeks, three weeks, one month, at least two months, at least three months, at least four months, at least five months, at least six months or more, including indefinitely during therapy. In certain embodiments, the ocular formulation of levcromakalim thereof, including levcromakalim, is administered once, twice, three, or more times a day.

The ocular formulations of (lev)cromakalim as described herein are administered topically. For topical delivery, the topical dosage form can be administered, for example, once a day (QD), twice a day (BID), three times a day (TID), four times a day (QID), once every other day (Q2D), once every third day (Q3D), as needed, or any dosage schedule that provides treatment of a disorder described herein. Alternatively, the immediate release formulation can be prepared for long term delivery, such as every 1, 2, 3, 4, 5, 6, 7, 8, 9, 10, 11 or 12 weeks or more, or every 1, 2, 3, 4, 5 or 6 months or more or less, including indefinitely on a permanent basis.

Ocular formulation of (lev)cromakalim can also be used for ocular therapy using an alternative route: intravitreal, intrastromal, intracameral, sub-tenon, sub-retinal, retro-bulbar, peribulbar, suprachoroidal, subchoroidal, choroidal, conjunctival, subconjunctival, episcleral, periocular, transscleral, posterior juxtascleral, circumcorneal, or tear duct injections, or through a mucus, mucin, or a mucosal barrier, in the described immediate release fashion or via an ocular device, or injection. In certain embodiments, the ocular device is a contact lens that releases the immediate release formulation of (lev)cromakalim.

Patient compliance and adherence are serious issues, and the fewer times per day that dosing is required, the more likely compliance is achieved. Once daily ocular formulation dosing for glaucoma is advantageous to maintain the ocular pressure in the desired range to minimize optic nerve damage, while also optimizing compliance and adherence. The ocular formulation of (lev)cromakalim, in the selected effective dosage in certain embodiments can be administered once-daily (QD), twice-daily (BID) or three times a day (TID) in a topical drop or other convenient manner.

In certain embodiments, formulations described herein comprising cromakalim, such as levcromakalim, and mixtures of selected pharmaceutically acceptable components described herein are administered through daily dosing. Non-limiting examples of (lev)cromakalim formulations used for daily dosing include:

Example 2j, wherein the ocular formulation comprises levcromakalim, glycerin, Kolliphor® ELP, polysorbate 80, poloxamer 407, hypromellose, mannitol, and BAK.

Example 3a, wherein the ocular formulation comprises levcromakalim, polysorbate 80, Kolliphor® ELP, and PVP.

Example 3b, wherein the ocular formulation comprises levcromakalim, Kolliphor® ELP, polysorbate 80, and poloxamer 407.

Example 3c, wherein the ocular formulation comprises levcromakalim, Kolliphor® ELP, polysorbate 80, PVP, and poloxamer 407.

Example 3d, wherein the ocular formulation comprises levcromakalim, Kolliphor® ELP, polysorbate 80, PVP, poloxamer 407, and mannitol.

Example 3d, wherein the ocular formulation comprises levcromakalim, Kolliphor® ELP, polysorbate 80, PVP, poloxamer 407, and mannitol.

Example 3e, wherein the ocular formulation comprises levcromakalim, glycerin, Kolliphor® ELP, polysorbate 80, poloxamer 407, and hypromellose.

Example 3f, wherein the ocular formulation comprises levcromakalim, Kolliphor® ELP, polysorbate 80, PVP, poloxamer 407, mannitol; and BAK.

Example 3g, wherein the ocular formulation comprises levcromakalim, Kolliphor® ELP, polysorbate 80, PVP, poloxamer 407, and mannitol.

Example 3h, wherein the ocular formulation comprises levcromakalim, glycerin, Kolliphor® ELP, polysorbate 80, poloxamer 407, mannitol, and hypromellose.

IV. Use of Ocular Formulations of (lev)cromakalim

The present invention provides methods for the use of the (lev)cromakalim formulations of the present invention to deliver an effective amount of ocular formulation of (lev) cromakalim or its salt to treat any disorder that can be treated with (lev)cromakalim or a pharmaceutically acceptable salt thereof.

In certain embodiments, an ocular formulation is provided that is appropriate to treat elevated IOP glaucoma, including but not limited to primary open angle glaucoma (POAG), primary angle closure glaucoma, pediatric glaucoma, pseudo-exfoliative glaucoma, pigmentary glaucoma, traumatic glaucoma, neovascular glaucoma, iridocorneal endothelial glaucoma (primary open angle glaucoma is also known as chronic open angle glaucoma, chronic simple glaucoma, and glaucoma simplex) is provided. In alternative embodiments the formulation is used to treat acute high-pressure glaucoma resulting from advanced cataracts. In another embodiment, the formulation is used to treat acute high-pressure glaucoma resulting from steroid induced glaucoma, uveitic glaucoma, or post-intravitreal injections, or for glaucoma that is not associated with elevated intraocular pressure, including but not limited to normal tension glaucoma (NTG) (also known as low tension glaucoma or normotensive glaucoma). In a nonlimiting illustrative embodiment, it is administered with an ocular formulation of the compounds described herein, including for example, a formulation comprising Kolliphor®, polysorbate, polyvinylpyrrolidone or PVP, poloxamer, mannitol, and a benzalkonium chloride (BAK).

Intraocular Pressure (IOP)

IOP is dictated by the rate of aqueous humor (AH) production and outflow. One way to specifically quantify these factors is by the modified Goldmann Equation (Lee S S, Robinson M R, Weinreb R N. Episcleral venous pressure and the ocular hypotensive effects of topical and intracameral prostaglandin analogs. *J Glaucoma.* 2019; 28(9): 846-57), shown below, which states that IOP is equal to episcleral venous pressure (EVP) plus the rate of AH inflow (Q) minus the uveoscleral outflow rate (U), divided by the conventional trabecular outflow rate (C) and EVP:

$$IOP=EVP+[(Q-U)/C]$$

Currently approved pharmacological therapies for the management of IOP primarily impact 'Q', 'C', and 'U' by affecting the ciliary body, trabecular meshwork (TM), and uveoscleral tissues of the eye, respectively. For example, beta blockers such as timolol, betaxolol, levobunolol, and metipranolol, alpha agonists such as brimonidine, and apraclonidine, and carbonic anhydrase inhibitors such as brinzolamide, dorzolamide, acetazolamide, and methazolamide impact AH inflow rate (Q). Therapeutics targeting the uvescleral outflow rate (U) include prostaglandin analogs such as latanoprost, bimatoprost, travaprost, tafluprost, latanoprostene bunod, and alpha agonists such as brimonidine, and apraclonidine. Conventional trabecular outflow facility (C) is impacted by cholinergics or mitotics such as pilocarpine, and carbachol, and Rho kinase inhibitors such as netarsudil. In contrast, none of the available pharmacological therapies predominantly lower EVP or specifically target tissues and vessels that are distal to the TM such as the collector channels, the deep scleral and intrascleral venous plexus, or the episcleral veins. In some embodiments, the present invention is administered along with one or a combination of these standard or (all drugs).

Of the 4 components of IOP, EVP is typically the largest one, equaling approximately 50 to 60% of the total IOP (Lee S S, Robinson M R, Weinreb R N. Episcleral venous pressure and the ocular hypotensive effects of topical and intracameral prostaglandin analogs. *J Glaucoma.* 2019; 28(9): 846-57). Importantly, EVP dictates the lower limit of IOP (typically, 8 to 12 mmHg), setting the "floor" for maximal therapy. For example, a higher EVP places a limit on the therapeutic potential of pharmacological therapies, namely those for NTG and certain surgical modalities such as minimally invasive glaucoma surgery (MIGS) devices, for the treatment of POAG. Notably, EVP has been found to be higher in untreated NTG and POAG compared with age-matched controls (Selbach J M, Posielek K, Steuhl K P, Kremmer S. Episcleral venous pressure in untreated primary open-angle and normal-tension glaucoma. *Ophthalmologica.* 2005; 219(6):357-61). Therefore, both NTG and POAG patients could benefit from EVP-lowering agents.

In certain embodiments, the ocular formulations of the present invention lowers IOP by lowering EVP at certain specific concentrations. For example, as shown in Example 7, formulation 3d lowers IOP by reducing episcleral venous pressure (EVP) in normotensive C57/BL6J mice.

Glaucoma

Glaucoma is a complex, multifactorial optic neuropathy and a leading cause of irreversible blindness that affects over 80 million people worldwide (Quigley H A, Broman A T. The number of people with glaucoma worldwide in 2010 and 2020. *Br J Ophthalmol.* 2006; 90(3):262-7; Weinreb R N, Aung T, Medeiros F A. The pathophysiology and treatment of glaucoma: a review. *JAMA.* 2014; 311(18):1901-11; and Tham Y C, Li X, Wong T Y, et al. Global Prevalence of Glaucoma and Projections of Glaucoma Burden through 2040: A Systematic Review and Meta-Analysis. *Ophthalmology.* 2014; 121(11): 2081-90). Historically, elevated intraocular pressure (IOP) has been a leading and the only modifiable risk factor for glaucoma. Lowering IOP is essential to slow down disease progression and vision loss (Weinreb R N, Aung T, Medeiros F A. The pathophysiology and treatment of glaucoma: a review. *JAMA.* 2014; 311(18): 1901-11).

Traditionally, IOP less than 21 mmHg is considered "normal," whereas pressures above 21 mmHg are considered a clinical warning sign (Dielemans I, Vingerling J R, Algra D, et al. Primary open-angle glaucoma, intraocular pressure, and systemic blood pressure in the general elderly population. The Rotterdam Study. *Ophthalmology.* 1995; 102(1):54-60). Ocular hypertension (OHT) is a condition in which IOP is elevated without glaucomatous findings (e.g., structural changes in cup-to-disc ratio or visual field loss). An economic analysis revealed that subjects with OHT have an overall risk of 10% of developing glaucoma over 5 years (Mansberger S L, Medeiros F A, Gordon M. Diagnostic tools for calculation of glaucoma risk. *Surv Ophthalmol.* 2008; 53(SUPPL1):S11-6) and as such are often treated prophylactically as a means of prevention. Results from the pivotal Ocular Hypertension Treatment Study showed that the risk of developing POAG can be reduced through medical treatments that lower IOP. A patient is considered to have POAG only after glaucomatous clinical findings such as changes in cup-to-disc ratio or observation of visual field changes. (Kass M A, Heuer D K, Higginbotham E J, et al. The Ocular Hypertension Treatment Study: a randomized trial determines that topical ocular hypotensive medication delays or prevents the onset of primary open-angle glaucoma. *Arch Ophthalmol.* 2002; 120(6):701-13).

IOP is maintained by balanced production and outflow of aqueous humor (AH), a clear fluid that serves as a nutrient source for the avascular tissues in the anterior segment such as the lens and cornea (Goel M, Picciani R G, Lee R K, Bhattacharya S K. Aqueous humor dynamics: a review. *Open Ophthalmol J.* 2010; 4:52-9). AH is produced in humans at a rate of 2.4 μL/min and must drain at roughly the same rate in order for IOP to remain within a "normal" and steady homeostatic range. AH can exit the eye through one of two drainage pathways: the conventional outflow pathway, including the trabecular meshwork (TM) and Schlemm's Canal, or the uveoscleral pathway, in which AH percolates through spaces in the extracellular matrix and ciliary muscle. In middle-aged and older adults, up to 80% of AH exits the eye through the conventional pathway, while the remaining 20% or less leaves via the uveoscleral pathway. If this balance between AH production and conventional outflow is disrupted, IOP can become elevated.

Open-angle glaucoma is the most common type in the United States, where 9 in 10 people with glaucoma have the open-angle type. Over time, the pressure damages the optic nerve, which affects vision. This can eventually lead to blindness. In primary open angle glaucoma (POAG), the drainage angle formed by the cornea and iris remains open, but there is increased resistance to outflow through the conventional outflow pathway, causing IOP to be increased (Kwon Y H, Fingert J H, Kuehn M H, Alward W L. Primary open-angle glaucoma. *N Engl J Med.* 2009; 360(11):1113-24; and Weinreb R N, Khaw, PT. Primary open-angle glaucoma. *Lancet.* 2004; 363(9422):1711-20). For most patients, elevated IOP over time will closely correlate to the damage of the retinal nerve fiber layer and the optic nerve head, and subsequent gradual but intractable vision loss due to loss of retinal ganglion nerve fibers (Quigley H A, Broman A T. The number of people with glaucoma worldwide in 2010 and 2020. *Br J Ophthalmol.* 2006; 90(3):262-7; and Weinreb R N, Aung T, Medeiros F A. The pathophysiology and treatment of glaucoma: a review. *JAMA.* 2014; 311(18):1901-11), which congregate at the optic disc and form the optic nerve. Therefore, lowering IOP still remains a primary treatment goal for POAG, and it can also be "neuroprotective" given the ultimate preservation of the optic nerve fibers (Weinreb R N, Leung C K, Crowston J G, et al. Primary open-angle glaucoma. *Nat Rev Dis Primers.* 2016; 2:16067).

Normal-tension glaucoma (NTG) is a type of open-angle glaucoma that happens in people with normal eye pressure. In NTG, the IOP is within the normal range, yet the optic nerve still becomes damaged, and subjects exhibit progressive glaucomatous visual field loss despite "normal" IOP. Although IOP-independent risk factors are believed to play a role in the pathogenesis of NTG, lowering IOP is still a mainstay of treatment as demonstrated in the Collaborative Normal Tension Glaucoma Study (Anderson D R, Normal Tension Glaucoma Study. Collaborative normal tension glaucoma study. *Curr Opin Ophthalmol.* 2003; 14(2):86-90). NTG is common in the Asian population.

Angle-closure glaucoma, also called narrow-angle or acute glaucoma is a severe form of glaucoma that constitutes a medical emergency. In this type of glaucoma, the outer edge of the iris blocks fluid from draining out of the front of the eye. The fluid builds up quickly, causing a sudden increase in eye pressure. If it's not treated, angle-closure glaucoma can cause blindness in just a few days. Another type of angle-closure glaucoma, sometimes called slow or chronic angle-closure. In another type of glaucoma, congenital glaucoma, babies are born with a problem in their eye that keeps fluid from draining normally.

Glaucoma caused by another medical condition is called secondary glaucoma. Neovascular glaucoma is often caused by diabetes or high blood pressure happens, where the eye makes extra blood vessels that cover the part of eye where fluid would normally drain. Pigmentary glaucoma is a secondary glaucoma where the pigment (color) from your iris (the colored part of your eye) flakes off and blocks fluid from draining out of the eye. Exfoliation glaucoma (sometimes called pseudoexfoliation) is a type of open-angle glaucoma that happens in some people with exfoliation syndrome, a condition that causes extra material to deposit on parts of the eye and block fluid from draining. Uveitic glaucoma can happen in people who have uveitis, a condition that causes swelling and inflammation in the eye. Uveitis can cause inflammation and scar tissue in the middle of the eye. This may damage or block the part of the eye where fluid drains out, causing high eye pressure and leading to uveitic glaucoma and vision loss.

High intraocular pressure is a common symptom of the most common glaucoma and treatments to lower intraocular pressure slow down glaucoma onset and progression.

Glaucoma can be treated with formulations described herein comprising cromakalim, such as levcromakalim, and mixtures of selected pharmaceutically acceptable components described herein. In certain embodiments, the formulations of the present invention can be used to treat glaucoma, wherein reduction in IOP is due to lowering of the EVP. Non-limiting examples of (lev)cromakalim formulations used to treat glaucoma (increased pressure or normal tension) include:

Example 2j, wherein the ocular formulation comprises levcromakalim, glycerin, Kolliphor®, polysorbate, poloxamer, hypromellose, mannitol, and BAK.

Example 3a, wherein the ocular formulation comprises leveromakalim, polysorbate, Kolliphor®, and PVP.

Example 3b, wherein the ocular formulation comprises leveromakalim, Kolliphor®, polysorbate, and poloxamer 407.

Example 3c, wherein the ocular formulation comprises leveromakalim, Kolliphor®, polysorbate, PVP, and poloxamer.

Example 3d, wherein the ocular formulation comprises levcromakalim, Kolliphor®, polysorbate, PVP, poloxamer, and mannitol.

Example 3e, wherein the ocular formulation comprises levcromakalim, glycerin, Kolliphor® ELP, polysorbate 80, poloxamer 407, and hypromellose.

Example 3f, wherein the ocular formulation comprises levcromakalim, Kolliphor® ELP, polysorbate 80, PVP, poloxamer 407, mannitol; and BAK.

Example 3g, wherein the ocular formulation comprises levcromakalim, Kolliphor®, polysorbate, PVP, poloxamer, hypromellose and mannitol.

Example 3h, wherein the ocular formulation comprises levcromakalim, glycerin, Kolliphor®, polysorbate, poloxamer, mannitol, and hypromellose.

Hyperemia

In certain embodiments, ocular therapy using an effective amount of ocular formulation of (lev)cromakalim, that does not result in significantly meaningful hyperemia is provided. Hyperemia is an excess and or prominence of blood in vessels supplying an organ. Ocular hyperemia, also called "red eye", can include or result in vascular congestion, excessive vascular vasodilation, small bleeds, small punctate bleeds and/or micro hemorrhages. Ocular hyperemia can have a variety of causes, including but not limited to, exogenous irritants, contact lens, inflammation, vessel disruption, conjunctivitis (including infectious or allergic), trauma, endogenous ocular insults, subconjunctival hemorrhage, conjunctival hemorrhage, blepharitis, anterior uveitis, glaucoma, or irritating drugs and environmental irritants (i.e., sun and wind).

Certain ocular drugs either do not address hyperemia or cause hyperemia. According to the present invention, the use of ocular formulation of (lev)cromakalim does not cause significantly meaningful hyperemia in the patient when used during therapy. Significantly meaningful hyperemia in certain embodiments is that which causes enough discoloration or discomfort to the patient that the patient considers it an adverse effect of the treatment, which can, if significant enough and/or prolonged, lead to poor compliance and even discontinuation of therapy. The present invention can result in an advance in the art by assisting patient compliance and comfort. In certain embodiments, the administration of ocular formulation of (lev)cromakalim does not significantly induce the expression of at least one protein independently selected from CD31 and VE-Cadherin.

In certain embodiments, ocular formulation administered that does not result in significantly meaningful hyperemia comprises cromakalim, such as levcromakalim, and mixtures of selected pharmaceutically acceptable components described herein.

Sturge Weber Syndrome

Sturge Weber Syndrome is a congenital disorder that affects the skin, neurological system and sometimes the eyes. It is sometimes referred to as a neurocutaneous disorder. It is a condition that affects the development of certain blood vessels, causing abnormalities in the brain, skin, and eyes from birth. Sturge Weber Syndrome has three major features: a red or pink birthmark called a port-wine birthmark, a brain abnormality called a leptomeningeal angioma, and increased IOP in the eye (glaucoma). In individuals with Sturge Weber Syndrome, glaucoma typically develops either in infancy or early adulthood and can cause vision impairment. In some affected infants, the pressure can become so great that the eyeballs appear enlarged and bulging (buphthalmos). Individuals with Sturge Weber Syndrome can have tangles of abnormal blood vessels (hemangiomas) in various parts of the eye. When these abnormal blood vessels develop into a network of blood vessels at the back of the eye (choroid), it is called a diffuse choroidal hemangioma and occurs in about one-third of individuals with Sturge Weber Syndrome. A diffuse choroidal hemangioma can cause vision loss. When present, the eye abnormalities typically occur on the same side of the head as the port-wine birthmark.

Another aspect of the present invention is the use of ocular formulation for the treatment of glaucoma associated with Sturge Weber Syndrome. Sturge Weber Syndrome-induced glaucoma affects 30-70% of the patients. Managing Sturge Weber Syndrome-induced glaucoma can be complex, and a number of patients need surgery or a drainage device. According to the invention, Sturge Weber Syndrome-induced glaucoma can be treated by administering an effective amount of ocular formulation of (lev)cromakalim.

In certain embodiments glaucoma can be treated with formulations described herein comprising cromakalim, such as levcromakalim, and mixtures of selected pharmaceutically acceptable components described herein.

Diabetic Retinopathy

Diabetic retinopathy (DR) is a diabetes complication caused by damage to the blood vessels of the light-sensitive tissue at the back of the eye (retina). The two stages of DR are nonproliferative retinopathy, and proliferative retinopathy. In the nonproliferative stage, the blood vessels swell and leak, which can cause macular edema, and affect vision due to loss of blood supply. In the proliferative/advanced stage DR, abnormal new blood vessels grown on retinal surface, which can break and bleed into the vitreous, and cause vision loss. DR can develop in diabetes type 1 or type 2 due to high blood sugar.

Another aspect of the present invention is the use of ocular formulation for the treatment of elevated intraocular pressure, and glaucoma associated with diabetic retinopathy. According to the invention, elevated intraocular pressure and glaucoma associated with DR can be treated by administering an effective amount of ocular formulation of (lev) cromakalim.

In certain embodiments DR can be treated with formulations described herein comprising cromakalim, such as levcromakalim, and mixtures of selected pharmaceutically acceptable components described herein.

Optic Neuropathy Related Mitochondrial Disorders

Mitochondrial diseases are medical, genetic, and often inherited. The diseases are a clinically heterogeneous group of disorders that result from a dysfunction in the mitochondrial respiratory chain. The mitochondrial respiratory chain is the essential final common pathway for aerobic metabolism, and tissues and organs that are highly dependent on aerobic metabolism are preferentially involved in mitochondrial disorders. While some mitochondrial disorders only affect a single organ, many involve multiple organ systems and often present with prominent neurologic and myopathic features. Mitochondria contain a potassium specific channel (mitoKATP channel) sensitive to ATP. The mitochondrial KATP channel plays an important role in the mitochondrial volume control and in regulation of the components of protonmotive force.

Inside the mitochondrion is a group of proteins that carry electrons along four chain reactions (Complexes I-IV), resulting in energy production. This chain is known as the Electron Transport Chain. A fifth group (Complex V) churns out the ATP. Together, the electron transport chain and the ATP synthase form the respiratory chain and the process is known as oxidative phosphorylation or OXPHOS. Complex I, the first step in this chain, is the most common site for mitochondrial abnormalities, representing as much as one third of the respiratory chain deficiencies.

A number of specific mitochondrial disorders have been associated with Complex I deficiency including Leber's hereditary optic neuropathy, mitochondrial encephalomyopathy lactic acidosis and stroke-like episodes (MELAS), myoclonic epilepsy with ragged red fibers (MERRF), and Leigh Syndrome.

There are many other types of mitochondrial diseases. For example, dominant optic atrophy (DOA) is an inherited optic nerve disorder characterized by degeneration of the optic nerves that typically starts during the first decade of life. Affected people usually develop moderate visual loss and color vision defects. The severity varies and visual acuity can range from normal to legal blindness. Autosomal dominant optic atrophy plus syndrome (ADOA plus) is a rare syndrome that causes vision loss, hearing loss, and symptoms affecting the muscles. The syndrome is associated with optic atrophy. Other symptoms of ADOA plus include sensorineural hearing loss and symptoms affecting the muscles such as muscle pain and weakness. ADOA plus is caused by mutations in the OPA1 gene. Both DOA and ADOA are inherited in an autosomal dominant manner. In certain embodiments, an effective amount of ocular formulation of (lev)cromakalim, is administered for the treatment of dominant optic atrophy (DOA) or autosomal dominant optic atrophy plus syndrome (ADOA plus).

Chronic progressive external ophthalmoplegia (CPEO) is a condition characterized mainly by a loss of the muscle functions involved in eye and eyelid movement. Signs and symptoms tend to begin in early adulthood and most commonly include weakness or paralysis of the muscles that move the eye (ophthalmoplegia) and drooping of the eyelids (ptosis). Some affected individuals also have myopathy, which may be especially noticeable during exercise. CPEO can be caused by mutations in any of several genes, which may be located in mitochondrial DNA or nuclear DNA. CPEO can occur as part of other underlying conditions, such as ataxia neuropathy spectrum and Kearns-Sayre syndrome (KSS). KSS is a slowly progressive multi-system mitochondrial disease that often begins with ptosis. Other eye muscles eventually become involved, resulting in paralysis of eye movement. Degeneration of the retina usually causes difficulty seeing in dimly lit environments. In certain embodiments, an effective amount of ocular formulation of (lev)cromakalim is administered for the treatment of chronic progressive external ophthalmoplegia or Kearns-Sayre syndrome.

Leber hereditary optic neuropathy (LHON) is a condition characterized by vision loss. Some affected individuals develop features similar to multiple sclerosis. LHON is caused by mutations in the MT-ND1, MT-ND4, MT-ND4L, and MT-ND6 genes. In certain embodiments, an effective amount of ocular formulation of (lev)cromakalim is administered for the treatment of Leber hereditary optic neuropathy.

Mitochondrial enoyl CoA reductase protein associated neurodegeneration (MEPAN) is caused by 2 mutations in the gene MECR (which encodes the protein mitochondrial trans-2-enoyl-coenzyme A-reductase). Characteristics of MEPAN include optic atrophy and childhood-onset dystonia. In certain embodiments, an effective amount of ocular formulation of (lev)cromakalim is administered for the treatment of mitochondrial enoyl CoA reductase protein associated neurodegeneration (MEPAN).

POLG-related disorders comprise a continuum of overlapping phenotypes with onset from infancy to late adulthood. Mutations in POLG can cause early childhood mitochondrial DNA (mtDNA) depletion syndromes or later-onset syndromes arising from mtDNA deletions. POLG mutations are the most common cause of inherited mitochondrial disorders, with as many as 2% of the population carrying these mutations. The six leading disorders caused by POLG mutations are Alpers-Huttenlocher syndrome, which is one of the most severe phenotypes; childhood myocerebrohepatopathy spectrum, which presents within the first three years of life; myoclonic epilepsy myopathy sensory ataxia; ataxia neuropathy spectrum (which includes the phenotypes previously referred to as mitochondrial recessive ataxia syndrome (MIRAS) and sensory ataxia neuropathy dysarthria and ophthalmoplegia (SANDO)); autosomal recessive progressive external ophthalmoplegia; and, autosomal dominant progressive external ophthalmoplegia. In certain embodiments, an effective amount of ocular formulation of (lev)cromakalim is administered for the treatment of a POLG-related disorder.

In certain embodiments Optical Neuropathy can be treated with formulations described herein comprising cromakalim, such as levcromakalim, and mixtures of selected pharmaceutically acceptable components described herein.

Ophthalmic Neuroprotection

Neuroprotection is a therapeutic strategy with the goal of maximizing the recovery of neural cells and minimizing neuronal cell death due to injury. The injury can be mechanical, ischemic, degenerative, or caused by radiation. Many neurodegenerative disorders are associated with aging, which can be detrimental for the elderly population. For example, glaucoma is often characterized by the loss of retinal ganglion cells and is a major cause of vision loss and blindness in the elderly.

In certain embodiments, an ocular formulation of (lev)cromakalim is administered to a host in need thereof for the treatment of an ocular-related neurodegenerative disorder. An ocular-related neurodegenerative disorder is any disorder that is associated with the dysfunction or degeneration of neurons or cells, including neural cells, such as retinal ganglion cells.

In certain embodiments of the present invention, an ocular formulation of (lev)cromakalim is administered as a method for reducing neuronal or cellular damage in the eye of host in need thereof. In certain embodiments, ocular formulation of (lev)cromakalim is administered as a method for reducing neuronal or cellular damage in the eye of host in need thereof wherein the eye is glaucomatous.

In certain embodiments, an ocular formulation of (lev)cromakalim promotes the survival, growth, regeneration, and/or neurite outgrowth of retinal ganglion cells. In certain embodiments, ocular formulation of (lev)cromakalim prevents the death of damaged neuronal cells.

Neuronal cell death can also be a result of retinal ischemia, and therefore in certain embodiments, ocular formulation of (lev)cromakalim is administered as a method of reducing neuronal or cellular damage in the eye following retinal ischemia in a host in need thereof.

Optic neuropathy, which is damage to the optic nerve often characterized by visual loss, results in the loss of retinal ganglion cells. There are many types of optic neuropathies, including ischemic optic neuropathy, optic neuritis, compressive optic neuropathy, infiltrative optic neuropathy, and traumatic optic neuropathy. Nutritional optic neuropathy can also result from under nutrition and/or a vitamin B12 deficiency. Toxic optic neuropathy can result from exposure to ethylene glycol, methanol, ethambutol, amiodarone, tobacco, or certain drugs, such as chloramphenicol or digitalis. Certain forms of optic neuropathy can be inherited, including Leber's hereditary optic neuropathy (LHON), dominant optic atrophy, Behr's syndrome, and Berk-Tabatznik syndrome. In certain embodiments, an effective amount of ocular formulation of (lev)cromakalim is administered as a method for reducing neuronal or cellular damage in the eye of a host in need thereof with optic neuropathy.

Additional non-limiting examples of ocular-related neurodegenerative diseases include lattice dystrophy, retinitis pigmentosa, age-related macular degeneration (wet or dry), photoreceptor degeneration associated with wet- or dry-age related macular degeneration, and optic nerve drusen.

Integrated or Adjunctive Therapy with Microinvasive Glaucoma Surgery (MIGS)

Minimally (or Micro) Invasive Glaucoma Surgery (MIGS) has become an innovative procedure in the evolution of glaucoma surgery. Since glaucoma is a disease in which the optic nerve gets damaged primarily due to elevated IOP, the goal of glaucoma surgery is to lower IOP to prevent or reduce damage to the optic nerve.

Standard glaucoma surgeries are still considered a major surgery and involve trabeculectomy, ExPRESS shunts, or external tube-shunts such as the Ahmed, Molteno, and Baerveldt style valve implants. While such procedures have often been effective at lowering eye pressure and preventing progression of glaucoma, they have numerous potential complications such as double vision, devastating eye infections, exposure of a drainage implant, swelling of the cornea, and excessively low IOP.

According to Saheb and Ahmed, minimally (or micro) invasive glaucoma surgery refers to a group of procedures which share five preferable qualities:

1. an ab interno and/or ab externo approach through a clear corneal incision which may spare the conjunctiva of incision;
2. a minimally traumatic procedure to the target tissue;
3. an IOP lowering efficacy that justifies the approach;
4. a high safety profile avoiding serious complications compared to other glaucoma surgeries, and given lower likelihood of hypotony; and
5. an effective recovery with minimal impact on the patient's quality of life.

The MIGS group of operations have been developed in recent years to reduce some of the complications of most standard glaucoma surgeries and therefore, in certain embodiments, ocular formulation of (lev)cromakalim is used as an additive in combination with a microinvasive glaucoma surgery (MIGS).

MIGS is intended to achieve lower IOP in patients with glaucoma with a less invasive surgical procedure, and ideally to achieve a medication sparing effect. MIGS procedures work by using microscopic-sized equipment and tiny incisions, enable controlled outflow and are often conducted at the time of cataract surgery. While they reduce the incidence of complications, some degree of effectiveness is traded for increased safety. (Pillunat, L. E., et al., *Clin Ophthalmol.* 2017; 11: 1583-1600)

The MIGS group of operations are divided into several categories:

1. Trabecular bypass operations (i.e., angle-based devices and or subconjunctival shunting devices);
2. Microtrabeculectomies (miniaturized versions of trabeculectomy);
3. Totally internal or suprachoroidal shunts; and,
4. Milder, gentler versions of laser photocoagulation.

Trabecular Surgery (Trabeculotomy) involves the use of a special contact lens on the eye and cutting through the trabecular meshwork with a tiny device under high power microscopic control. This is done without damaging any other tissues in the ocular drainage pathway. The trabecular meshwork can either be destroyed (Trabectome, Trab360, or OMNI Surgical System) or bypassed using a tiny snorkel-like device (the iStent) or using a plug-shaped stent device (iStent Inject). Both procedures are FDA-approved but generally do not reduce eye pressure low enough and are thus useful in early to moderate stages of glaucoma. With these devices, the resistance of the trabecular meshwork is obviated, thus primarily leaving distal outflow facility and episcleral venous pressure as limits to further aqueous humor drainage. In certain embodiments, ocular formulation of (lev)cromakalim is used as an additive in combination with Trabectome or Trab360 and/or the iStent/iStent Inject for the treatment of glaucoma by additively lowering IOP via increased distal outflow or reduced episcleral venous pressure prior to or after the procedure in an acute or chronic use setting.

Microtrabeculectomies work by inserting tiny, microscopic-sized tubes into the eye and draining the fluid from inside the eye to underneath the outer membrane of the eye (conjunctiva). The Xen Gel Stent and PRESERFLO are two new devices that can make the trabeculectomy operation safer. Results have shown excellent pressure lowering with improved safety over trabeculectomy in studies done outside the United States. In certain embodiments, the compounds of the present invention are used as part of the protocols with Xen Gel Stent and/or Preserflo for the treatment of glaucoma by additively lowering IOP via increased distal outflow or reduced episcleral venous pressure prior to or after the procedure in an acute or chronic use setting.

Suprachoroidal Shunts, including the Gold Micro-shunt, iStent Supra, Aquashunt, and STARflo, work by using tiny tubes with very small internal openings, the front of the eye is connected to the suprachoroidal space between the retina and the wall of the eye to augment the drainage of fluid from the eye. This operation has relatively few serious complications and lowers pressures enough to be useful even in moderately severe glaucoma. In certain embodiments, ocular formulation of (lev)cromakalim is used in combination with Suprachoroidal Shunts procedure for the treatment of glaucoma by additively lowering IOP via increased distal outflow or reduced episcleral venous pressure prior to or after the procedure in an acute or chronic use setting.

Trabecular bypass stents and shunts are investigational devices that work to dilate Schlemm's canal. These procedures facilitate the flow of aqueous into Schlemm's canal by shunting (Eyepass Glaucoma Implant; GMP Companies, Inc., Fort Lauderdale, FL), by stenting the canal itself (iStent; Glaukos Corp., Laguna Hills, CA), or by dilating the canal using viscoelastic (OMNI Surgical System; Sight Sciences, Menlo Park, CA). Other devices such as the Solx Gold Micro-Shunt (OccuLogix, Inc., Mississauga, Ontario, Canada) divert aqueous into the suprachoroidal space. In certain embodiments, ocular formulation of (lev)cromakalim is used in combination with trabecular bypass stents or shunts procedure for the treatment of glaucoma by additively lowering IOP via increased distal outflow or reduced episcleral venous pressure prior to or after the procedure in an acute or chronic use setting.

Selective laser trabeculoplasty (SLT) is used during the management of glaucoma to help lower IOP. Since the conduct of the LiGHT study, it is being used more often as first line-treatment to help lower IOP, effectively working at the level of the trabecular meshwork to improve outflow. In certain embodiments, ocular formulation of (lev)cromakalim is used alongside and/or in addition to SLT for the treatment of glaucoma by additively lowering IOP via increased distal outflow and/or reduced episcleral venous pressure prior to or after the procedure in an acute or chronic use setting.

Laser photocoagulation was previously reserved for advanced glaucoma that could not be controlled despite trabeculectomy or tube shunts. Endocyclophotocoagulation and micropulse Diode cyclophotocoagulation are two recent advances to the use of laser photocoagulation and have proven useful in cases where glaucoma has yet to become advanced. In certain embodiments, ocular formulation of (lev)cromakalim is used in the endocyclophotocoagulation and micropulse cyclophotocoagulation protocol for the treatment of glaucoma by additively lowering IOP via increased distal outflow and/or reduced episcleral venous pressure prior to or after the procedure in an acute or chronic use setting.

Endocyclophotocoagulation in recent years has become a widely accepted and popular treatment of refractory glaucoma, pediatric glaucoma, and as an adjunct to cataract surgery in both medically controlled and uncontrolled glaucoma in conjunction with phacoemulsification with intraocular lens placement. Endocyclophotocoagulation is performed following lens removal and intraocular lens implantation by inserting an endolaser unit through the cataract incision, across the anterior segment, and into the posterior chamber on the nasal side of the eye. Laser energy is applied to the ciliary processes to destroy ciliary epithelial cells that produce aqueous humor. In certain embodiments, ocular formulation of (lev)cromakalim is used in the endocyclophotocoagulation protocol for the treatment of glaucoma by additively lowering IOP via increased distal outflow and/or reduced episcleral venous pressure prior to or after the procedure in an acute or chronic use setting.

Micropulse cyclophotocoagulation delivers the laser in short bursts to allow the surgeon to target specific areas of the ciliary body while giving the tissue time to cool down between bursts, minimizing damage. MicroPulse P3 probe and the new Cyclo G6 glaucoma laser system (Iridex) has both been used successfully in retinal diseases, showing excellent safety and efficacy rates. In certain embodiments, ocular formulation of (lev)cromakalim is used in the Micropulse cyclophotocoagulation surgical protocol for the treatment of glaucoma by additively lowering IOP via increased distal outflow and/or reduced episcleral venous pressure prior to or after the procedure in an acute or chronic use setting.

Other devices include Gonioscopy-assisted transluminal trabeculotomy (GATT), Kahook Dual Blade, Ab interno canaloplasty and Hydrus Microstent, iStent Supra, Xen Glaucoma Treatment System and InnFocus MicroShunt. In certain embodiments, ocular formulation of (lev)cromakalim is used in the surgical protocol of these devices for the treatment of glaucoma as described above.

Laser Trabeculoplasty, including Selective Laser Trabeculoplasty (SLT), Argon Laser Trabeculoplasty (ALT), Excimer Laser Trabeculostomy and Micropulse Laser Trabeculoplasty (MLT) are surgical laser procedures that help to reduce resistance at the trabecular meshwork by ablating cells of the trabecular meshwork and improving outflow in a manner similar to other forms of trabeculoplasty and certain MIGS devices. In certain embodiments, Excimer Laser Trabeculostomy used as an additive in combination with Laser Trabeculoplasty for the treatment of glaucoma by additively lowering IOP via increased distal outflow or reduced episcleral venous pressure prior to or after the procedure in an acute or chronic use setting.

In certain embodiments, an ocular formulation of (lev) cromakalim is used as a secondary therapy to a prostaglandin analog, such as latanoprost (Xalatan), bimatoprost (Lumigan), travoprost (Travatan or Travatan Z), latanoprostene bunod (Vyzulta), or Tafluprost (Zioptan) and as an additive to a minimally (or micro) invasive glaucoma surgery (MIGS) as described herein. In a further embodiment, the MIGS is a trabeculotomy. In a further embodiment, the MIGS is a microtrabeculectomy. In a further embodiment, the MIGS is a suprachoroidal shunt. In a further embodiment, the MIGS is a trabecular bypass stent or shunt. In a further embodiment, the MIGS is a selective laser trabeculoplasty (SLT). In a further embodiment, the MIGS is a laser photocoagulation. In a further embodiment, the MIGS is endocyclophotocoagulation. In a further embodiment, the MIGS is laser trabeculoplasty.

In certain embodiments, an ocular formulation of (lev) cromakalim is used as a secondary therapy to latanoprost (Xalatan) and as an additive to a minimally (or micro) invasive glaucoma surgery as described herein. In a further embodiment, the MIGS is a trabeculotomy. In a further embodiment, the MIGS is a microtrabeculectomy. In a further embodiment, the MIGS is a suprachoroidal shunt. In a further embodiment, the MIGS is a trabecular bypass stent or shunt. In a further embodiment, the MIGS is a selective laser trabeculoplasty (SLT). In a further embodiment, the MIGS is a laser photocoagulation. In a further embodiment, the MIGS is endocyclophotocoagulation. In a further embodiment, the MIGS is laser trabeculoplasty.

In certain embodiments, an ocular formulation of (lev) cromakalim is used as a secondary therapy to an α-2 adrenergic agonist, such as brimonidine (Alphagan®), epinephrine, dipivefrin (Propine®) or apraclonidine (Lopidine®) and as an additive to a minimally (or micro) invasive glaucoma surgery (MIGS) as described herein. In a further embodiment, the MIGS is a trabeculotomy. In a further embodiment, the MIGS is a microtrabeculectomy. In a further embodiment, the MIGS is a suprachoroidal shunt. In a further embodiment, the MIGS is a trabecular bypass stent or shunt. In a further embodiment, the MIGS is a selective laser trabeculoplasty (SLT). In a further embodiment, the MIGS is a laser photocoagulation. In a further embodiment, the MIGS is endocyclophotocoagulation. In a further embodiment, the MIGS is laser trabeculoplasty.

In certain embodiments, an ocular formulation of (lev) cromakalim is used as a secondary therapy to a beta-blocker, such as timolol, betaxolol, levobunolol, metipranolol, or carteolol and as an additive to a minimally (or micro) invasive glaucoma surgery (MIGS) as described herein.

In a further embodiment, the MIGS is a trabeculotomy. In a further embodiment, the MIGS is a microtrabeculectomy. In a further embodiment, the MIGS is a suprachoroidal shunt. In a further embodiment, the MIGS is a trabecular bypass stent or shunt. In a further embodiment, the MIGS is a selective laser trabeculoplasty (SLT). In a further embodiment, the MIGS is a laser photocoagulation. In a further embodiment, the MIGS is endocyclophotocoagulation. In a further embodiment, the MIGS is laser trabeculoplasty. In a further embodiment, the MIGS is a trabeculotomy. In a further embodiment, the MIGS is a microtrabeculectomy. In a further embodiment, the MIGS is a suprachoroidal shunt. In a further embodiment, the MIGS is a trabecular bypass stent or shunt. In a further embodiment, the MIGS is a selective laser trabeculoplasty (SLT). In a further embodiment, the MIGS is a laser photocoagulation. In a further embodiment, the MIGS is endocyclophotocoagulation. In a further embodiment, the MIGS is laser trabeculoplasty.

In certain embodiments, an ocular formulation of (lev) cromakalim is used as a secondary therapy to a ROCK inhibitor, such as ripasudil, netarsudil (Rhopressa), fasudil, RKI-1447, GSK429286A, or Y-30141 and as an additive to a minimally (or micro) invasive glaucoma surgery (MIGS) as described herein. In a further embodiment, the MIGS is a trabeculotomy. In a further embodiment, the MIGS is a microtrabeculectomy. In a further embodiment, the MIGS is a suprachoroidal shunt. In a further embodiment, the MIGS is a trabecular bypass stent or shunt. In a further embodiment, the MIGS is a selective laser trabeculoplasty (SLT). In a further embodiment, the MIGS is a laser photocoagulation. In a further embodiment, the MIGS is endocyclophotocoagulation. In a further embodiment, the MIGS is laser trabeculoplasty.

In certain embodiments, an ocular formulation of (lev) cromakalim is used as a secondary therapy to a second ATP-sensitive potassium channel opener, such as minoxidil, diazoxide, nicorandil, or pinacidil and as an additive to a minimally (or micro) invasive glaucoma surgery (MIGS) as described herein. In a further embodiment, the MIGS is a trabeculotomy. In a further embodiment, the MIGS is a microtrabeculectomy. In a further embodiment, the MIGS is a suprachoroidal shunt. In a further embodiment, the MIGS is a trabecular bypass stent or shunt. In a further embodiment, the MIGS is a selective laser trabeculoplasty (SLT). In a further embodiment, the MIGS is a laser photocoagulation. In a further embodiment, the MIGS is endocyclophotocoagulation. In a further embodiment, the MIGS is laser trabeculoplasty.

In certain embodiments, an ocular formulation of (lev) cromakalim is used as a secondary therapy to a carbonic anhydrase inhibitor, such as dorzolamide (Trusopt®), brinzolamide (Azopt®), acetazolamide (Diamox®) or methazolamide (Neptazane®) and as an additive to a minimally (or micro) invasive glaucoma surgery (MIGS) as described herein. In a further embodiment, the MIGS is a trabeculotomy. In a further embodiment, the MIGS is a microtrabeculectomy. In a further embodiment, the MIGS is a suprachoroidal shunt. In a further embodiment, the MIGS is a trabecular bypass stent or shunt. In a further embodiment, the MIGS is a selective laser trabeculoplasty (SLT). In a further embodiment, the MIGS is a laser photocoagulation. In a further embodiment, the MIGS is endocyclophotocoagulation. In a further embodiment, the MIGS is laser trabeculoplasty.

Other Exemplary Ocular Disorders

Orbital tumors are benign or malignant space-occupying lesions of the orbit, often leading to dystopia of the eyeball, motility disturbances, diplopia, visual field defects, and sometimes a complete loss of vision. Often orbital tumors are removed via surgery and therefore a medication would be an advantageous therapeutic option. In certain embodiments, an effective amount of ocular formulation of (lev) cromakalim is administered for the treatment or reduction of orbital tumors. In certain embodiments, (lev)cromakalim is administered topically one time, two times, three times, or more a day. In certain embodiments, (lev)cromakalim is administered prior to or after surgery for the removal or reduction of orbital tumors.

Episcleral/orbital vein vasculitis is inflammation of the blood vessel wall. The clinical features of the eye vasculitis can vary from conjunctivitis, episcleritis, scleritis, peripheral ulcerative keratitis, proptosis, retinal vasculitis, orbititis to uveitis, depending on the site and distribution of the vessels involved. In certain embodiments, an effective amount of ocular formulation of (lev)cromakalim is administered for the treatment of episcleral/orbital vein vasculitis. In certain embodiments, a (lev)cromakalim formulation is administered as a topical drop.

Carotid-cavernous sinus fistula is an abnormal connection between an artery in the neck and the network of veins at the back of the eye. A fistula can raise the pressure in your cavernous sinuses, which may compress the cranial nerves located around the cavernous sinuses. This compression may damage the nerve function, which is to control your eye movements. Carotid-cavernous sinus fistula can be direct or indirect. Direct carotid-cavernous sinus fistulas are often caused by accidents or injuries that tear the carotid artery wall, while indirect carotid-cavernous sinus fistulas often arise without warning and are associated with high blood pressure, hardened arteries, pregnancy, and connective tissue disorders. In certain embodiments, an effective amount of ocular formulation of (lev)cromakalim is administered for the treatment of carotid-cavernous sinus fistula.

Dural cavernous sinus shunts are vascular communications in which blood flows through small meningeal branches of the carotid arteries to enter the venous circulation near the cavernous sinus. Often this disorder is congenital, and the onset of clinical abnormalities may be associated with the occurrence of intracranial venous thrombosis. In certain embodiments, an effective amount of ocular formulation of (lev)cromakalim is administered for the treatment of dural cavernous sinus shunts.

Orbital varices are a vascular hamartoma typified by a plexus of low pressure, low flow, thin walled and distensible vessels that intermingle with the normal orbital vessels. Most patients will experience positional proptosis with a head-down position, and intermittent proptosis that is exacerbated by coughing, straining, the Valsalva maneuver, or compression of the jugular veins. In certain embodiments, ocular formulation of (lev)cromakalim is administered for the treatment of orbital varices.

Branch retinal vein occlusion (BRVO) is the blockage of branches of the retinal vein causing blood and fluid to spill into the retina. Risk factors for BRVO include diabetes, elevated IOP, and high blood pressure. The macula can swell from this fluid, affecting central vision. Eventually, without blood circulation, nerve cells in the eye can die and vision loss can occur. In certain embodiments, an effective amount of ocular formulation of (lev)cromakalim is administered for the treatment of branch retinal vein occlusion (BRVO). In certain embodiments, the formulation of (lev)cromakalim is administered as a topical drop that is given once, twice, three, or more times a day.

Non-arteritic anterior ischemic optic neuropathy (NAION) refers to loss of blood flow to the optic nerve and is due to impaired circulation of blood at the optic nerve head. Non-arteritic anterior ischemic optic neuropathy is associated with diabetes, high blood pressure, atherosclerosis, a small optic nerve, elevated IOP, and sleep apnea. In certain embodiments, an effective amount of ocular formulation of (lev)cromakalim is administered for the treatment of non-arteritic anterior ischemic optic neuropathy. In certain embodiments, the formulation of (lev)cromakalim is administered as a topical drop that is given once, twice, three, or more times a day.

In additional aspects of the invention, an ocular formulation of (lev)cromakalim is used for the treatment of a selected ocular disorder, as described below.

Graves' ophthalmopathy or Graves' orbitopathy (or thyroid eye disease or thyroid-associated orbitopathy) are autoimmune inflammatory disorders of the orbit and periorbital tissues and typical signs of the diseases include upper eyelid retraction, lid lag, swelling, and bulging eyes. These disorders are orbital autoimmune disorders caused by an overactive thyroid. An effective amount of ocular formulation of (lev)cromakalim can be administered for the treatment of Graves' ophthalmopathy, Graves' orbitopathy, or thyroid-associated orbitopathy. The compound can be administered in any manner that achieves the desired effect, including as a topical drop taken as needed to reduce swelling and redness. In certain embodiments, ocular formulation of (lev)cromakalim is taken in combination with a corticosteroid drug or an immune suppression medication (rituximab or mycophenolate).

Cavernous sinus thrombosis is the formation of a blood clot within the cavernous sinus, a cavity at the base of the brain which drains deoxygenated blood from the brain back to the heart. This is a rare disorder and can be of two types: septic cavernous thrombosis and aseptic cavernous thrombosis. The cause is often secondary to an infection in the nose, sinuses, ears, or teeth. A common disorder secondary to cavernous sinus pathology is superior ophthalmic vein thrombosis, an uncommon orbital pathology that can present with sudden onset proptosis, conjunctival injection, and visual disturbance. In certain embodiments, an effective amount of ocular formulation of (lev)cromakalim is administered for the treatment of cavernous sinus thrombosis or superior ophthalmic vein thrombosis. In certain embodiments, an effective amount is administered in combination or alternation with an antibiotic, heparin, or a steroid. In one aspect, the compound is administered orally and is given at least once, twice, three, or more times a day as needed.

Central retinal vein occlusion, also known as CRVO, is a condition in which the main vein that drains blood from the retina becomes blocked partially or completely. This can cause blurred vision and other problems with the eye. Risk factors for CRVO include diabetes, elevated IOP, and high blood pressure. The macula can swell from this fluid, affecting central vision. Eventually, without blood circulation, nerve cells in the eye can die and vision loss can occur. In certain embodiments, an effective amount of ocular formulation (lev)cromakalim is administered for the treatment of central retinal vein occlusion. In certain embodiments, the compound is administered as a topical drop that is given once, twice, or three times a day.

V. Combination Therapy

In certain embodiments, an effective amount of an ocular formulation of (lev)cromakalim as described herein is administered to a host in need thereof in combination with an effective amount of a second active agent to treat the patient's ocular disorder.

Non-limiting examples of illustrative additional active agents that may be used according to the present invention include but are not limited to an effective amount of:

1) Latanoprost or Latanoprostene bunod;
2) Cyclosporine;
3) a nitric oxide donor, including, but not limited to, NO-donating prostaglandin analog eyedrop (NCX-470), NO-donating PDE5 inhibitor (NCX-1728), fluticanose propionate nanocrystal suspension (NCX-4251, or sodium nitroprusside (SNP);
4) a prostaglandin analog, such as latanoprost (Xalatan), bimatoprost (Lumigan), travoprost (Travatan or Travatan Z), or Tafluprost (Zioptan);
5) an α-2 adrenergic agonist, such as brimonidine (Alphagan®), epinephrine, dipivefrin (Propine®) or apraclonidine (Lopidine®));
6) a beta-blocker, such as timolol, levobunolol, metipranolol, or carteolol;
7) a ROCK inhibitor, such as ripasudil, netarsudil (Rhopressa®), fasudil, RKI-1447, GSK429286A, or Y-30141;
8) a combination product of a prostaglandin and ROCK inhibitor, such as Rocklatan® (latanprost and netarsudil);
9) a second ATP-sensitive potassium channel opener, such as minoxidil, diazoxide, nicorandil, or pinacidil;
10) a carbonic anhydrase inhibitor, such as dorzolamide (Trusopt®), brinzolamide (Azopt®), acetazolamide (Diamox®) or methazolamide (Neptazane®);
11) a combination product of a carbonic anhydrase inhibitor and a beta blocker, such as Cosopt® (dorzolamide and timolol); or
12) an anti-VEGF inhibitor such as bevacizumab (Avastin®), ranibizumab (Lucentis®), aflibercept (Eylea®), and brolucizumab (Beovu®).

EMBODIMENTS OF THE PRESENT INVENTION

1. An ocular topical formulation of (lev)cromakalim or a pharmaceutically acceptable salt thereof that has a concentration of between about 0.01 mM to about 5 mM, wherein the ocular topical formulation is stable at ambient conditions for at least 4 months and comprises three or more components selected from the group consisting of
   a. a polyol;
   b. a polyethoxylated furanose fatty acid ester;
   c. a nonionic tri-block copolymer of a central hydrophobic chain of polyoxypropylene flanked by two hydrophilic chains of polyoxyethylene (poloxamer);
   d. a polymeric alkyl or aryl polyol;
   e. an ethoxylated glycerol ester;
   f. a polymeric lactam;
   g. hydroxyalkyl cellulose;
   h. an oil in water polymeric emulsifier of a block copolymer of polyacrylic acid and a hydrophobic $C_{10}$-$C_{30}$ alkyl acrylate; and
   i. an ethoxylated alkylphenol;

in an aqueous formulation with a pH from about 6 to about 8.
2. The ocular topical formulation of embodiment 1, wherein the ocular topical formulation comprises four or more components.
3. The ocular topical formulation of embodiment 1, wherein the ocular topical formulation comprises five or more components.
4. The ocular topical formulation of embodiment 1, wherein the ocular topical formulation comprises six or more components.
5. The ocular topical formulation of any one of embodiments 1-4, wherein the composition comprises a polyol.
6. The ocular topical formulation of embodiment 5, wherein the polyol is an alkyl polyol.
7. The ocular topical formulation of embodiment 6, wherein the alkyl polyol is a triol.
8. The ocular topical formulation of embodiment 6, wherein the alkyl polyol is a sugar alcohol.
9. The ocular topical formulation of embodiment 7, wherein the triol is glycerin.
10. The ocular topical formulation of embodiment 6, wherein the alkyl polyol is mannitol.

11. The ocular topical formulation of any one of embodiments 1-10, wherein the composition comprises a polyethoxylated furanose fatty acid ester.
12. The ocular topical formulation of embodiment 11, wherein the polyethoxylated furanose fatty acid ester is polysorbate 80.
13. The ocular topical formulation of any of embodiments 1-12, wherein the composition comprises a poloxamer.
14. The ocular topical formulation of embodiment 13, wherein the poloxamer is poloxamer 407 or Pluronic 127.
15. The ocular topical formulation of any of the embodiments 1-14, wherein the composition comprises a polymeric alkyl or aryl polyol.
16. The ocular topical formulation of any of the embodiments 15, wherein the polymeric alkyl or aryl polyol is tyloxapol.
17. The ocular topical formulation of any of the embodiments 1-16, wherein the composition comprises an ethoxylated glycerol ester.
18. The ocular topical formulation of embodiment 17, wherein the ethoxylated glycerol ester is a Kolliphor® or Cremophor®.
19. The ocular topical formulation of embodiment 18, wherein the Kolliphor® or Cremophor® is selected from the group consisting of Kolliphor® ELP, Kolliphor® RH 40, Kolliphor® HS 15.
20. The ocular topical formulation of embodiment 19, wherein the Kolliphor® or Cremophor® is Kolliphor® ELP.
21. The ocular topical formulation of embodiment 19, wherein the Kolliphor® or Cremophor® is Kolliphor® RH 40.
22. The ocular topical formulation of embodiment 19, wherein the Kolliphor® or Cremophor® is Kolliphor® HS 15.
23. The ocular topical formulation of any of the embodiments 1-22, wherein the composition comprises a polymeric lactam.
24. The ocular topical formulation of embodiment 23, wherein the polymeric lactam is PVP.
25. The ocular topical formulation of embodiment 24, wherein the PVP is selected from the group PVP K-30 and PVP K-90.
26. The ocular topical formulation of embodiment 25, wherein the PVP is PVP K-30.
27. The ocular topical formulation of embodiment 25, wherein the PVP is PVP K-90.
28. The ocular topical formulation of any of the embodiments 1-27, wherein the composition comprises hydroxyalkyl cellulose.
29. The ocular topical formulation of embodiment 28, wherein the hydroxyalkyl cellulose is hypromellose.
30. The ocular topical formulation of any of the embodiments 1-29, wherein the composition comprises an oil in water polymeric emulsifier of a block copolymer of polyacrylic acid and a hydrophobic $C_{10}$-$C_{30}$ alkyl acrylate.
31. The ocular topical formulation of embodiment 30, wherein the oil in water polymeric emulsifier of a block copolymer of polyacrylic acid and a hydrophobic $C_{10}$-$C_{30}$ alkyl acrylate is Premulen.
32. The ocular topical formulation of embodiment 31, wherein the Premulen is Premulen™ TR-1 or Premulen™ TR-2.
33. The ocular topical formulation of any of the embodiments 1-32, wherein the composition comprises an ethoxylated alkylphenol.
34. The ocular formulation of embodiment 33, wherein the ethoxylated alkylphenol is octoxynol.
35. The ocular topical formulation of embodiment 34, wherein the octoxynol is octoxynol-40.
36. The ocular topical formulation of any of the embodiments of 1-35, wherein the formulation is stable at ambient conditions for at least 5 months.
37. The ocular topical formulation of embodiment of 36, wherein the formulation is stable at ambient conditions for at least 6 months.
38. The ocular topical formulation of embodiment 37, wherein the formulation is stable at ambient conditions for at least 7 months.
39. The ocular topical formulation of any of the embodiments 1-38, wherein the formulation is an aqueous formulation of pH of about 6.5 to about 7.5.
40. The ocular topical formulation of any of the embodiments 1-39, wherein the concentration of (lev)cromakalim is between about 0.05 mM to about 5 mM.
41. The ocular topical formulation of any of the embodiments 1-40, wherein the concentration of (lev)cromakalim is between about 0.5 mM to about 5 mM.
42. The ocular topical formulation of any of the embodiments 1-41, wherein the concentration of (lev)cromakalim is between t about 1 mM to about 5 mM.
43. The ocular topical formulation of any of the embodiments 1-42, wherein the concentration of (lev)cromakalim is between about 1.5 mM to about 5 mM.
44. The ocular topical formulation of any of the embodiments 1-43, wherein the concentration of (lev)cromakalim is between about 2 mM to about 5 mM.
45. The ocular topical formulation of any of the embodiments 1-44, wherein the concentration of (lev)cromakalim is between about 2.5 mM to about 5 mM.
46. The ocular topical formulation of any of the embodiments 1-45, wherein the concentration of (lev)cromakalim is between about 3 mM to about 5 mM.
47. The ocular topical formulation of any of the embodiments 1-46, wherein the concentration of (lev)cromakalim is between about 3.5 mM to about 5 mM.
48. The ocular topical formulation of any of the embodiments 1-47, wherein the concentration of (lev)cromakalim is between about 4 mM to about 5 mM.
49. An ocular topical formulation of (lev)cromakalim or a pharmaceutically acceptable salt thereof that has a concentration of between about 0.01 mM to about 5 mM and is stable at ambient conditions for at least 5 months and comprises three or more components selected from the group consisting of glycerin, polysorbate 80, poloxomer 407 or Pluronic® F127, tyloxapol, Kolliphor® ELP, Kolliphor® RH 40, Kolliphor® HS 15, hypromellose, PVP, Premulen™ TR-1 or Premulen™ TR-2, and octoxynol-40 in an aqueous formulation with a pH from about 6 to about 8.
50. The ocular topical formulation of embodiment 49 wherein the ocular formulation consists essentially of three or more components selected from the group consisting of glycerin, polysorbate 80, poloxomer 407 or Pluronic® F127, tyloxapol, Kolliphor® ELP, Kolliphor® RH 40, Kolliphor® HS 15, hypromellose, PVP, Premulen™ TR-1 or Premulen™ TR-2, and octoxynol-40 in an aqueous formulation with a pH from about 6 to about 8.

51. The ocular topical formulation of embodiment 49 wherein the ocular formulation consists essentially of Kolliphor® RH 40, octoxynol-40, and Premulen™ TR-2 in an aqueous formulation with a pH from about 6 to about 8.
52. The ocular topical formulation of embodiment 49 wherein the ocular formulation consists essentially of Kolliphor® RH 40, Kolliphor® HS 15, and PVP in an aqueous formulation with a pH from about 6 to about 8.
53. The ocular formulation of embodiment 49 wherein the ocular formulation consists essentially of glycerin, Kolliphor® ELP, polysorbate 80, and hypromellose in an aqueous formulation with a pH from about 6 to about 8.
54. The ocular formulation of embodiment 49 wherein the ocular formulation consists essentially of Kolliphor® ELP, polysorbate 80, and PVP in an aqueous formulation with a pH from about 6 to about 8.
55. The ocular formulation of embodiment 49 wherein the ocular formulation consists essentially of glycerin, Kolliphor® ELP, polysorbate 80, poloxamer 407, and hypromellose in an aqueous formulation with a pH from about 6 to about 8.
56. The ocular formulation of embodiment 49 wherein the ocular formulation consists essentially of glycerin, Kolliphor® RH 40, Premulen™ TR-2, and PVP in an aqueous formulation with a pH from about 6 to about 8.
57. The ocular formulation of embodiment 49 wherein the ocular formulation consists essentially of Kolliphor® HS 15, Premulen™ TR-2, polysorbate 80, octoxynol-40, and poloxamer 407 in an aqueous formulation with a pH from about 6 to about 8.
58. The ocular formulation of embodiment 49 wherein the ocular formulation consists of polysorbate 80, Kolliphor® ELP, and PVP in an aqueous formulation with a pH from about
6 to about 8.
59. The ocular formulation of embodiment 49 wherein the ocular formulation consists essentially of Kolliphor® ELP, polysorbate 80, and poloxamer 407 in an aqueous formulation with a pH from about 6 to about 8.
60. The ocular formulation of embodiment 49 wherein the ocular formulation consists essentially of Kolliphor® ELP, polysorbate 80, PVP, and poloxamer 407 in an aqueous formulation with a pH from about 6 to about 8.
61. The ocular formulation of embodiment 49 wherein the ocular formulation consists essentially of glycerin, Kolliphor® ELP, polysorbate 80, poloxamer 407, and hypromellose in an aqueous formulation with a pH from about 6 to about 8.
62. An ocular topical formulation that comprises (lev) cromakalim or a pharmaceutically acceptable salt thereof, Kolliphor® ELP, polysorbate 80, polyvinylpyrrolidone (PVP), poloxamer 407, mannitol, water, and phosphate buffer, and has a concentration of (lev) cromakalim or a pharmaceutically acceptable salt thereof of between about 0.01 mM to about 5 mM and is stable at ambient conditions for at least 5 months with a pH from about 6 to about 8.
63. The ocular topical formulation of embodiment 62 that has a concentration of (lev)cromakalim or a pharmaceutically acceptable salt thereof of between about 0.05 mM to about 5 mM.
64. The ocular topical formulation of any one of embodiments 62-63 that has a concentration of (lev)cromakalim or a pharmaceutically acceptable salt thereof of between about 0.5 mM to about 5 mM.
65. The ocular topical formulation of any one of embodiments 62-64 that has a concentration of (lev)cromakalim or a pharmaceutically acceptable salt thereof of between about 1 mM to about 5 mM.
66. The ocular topical formulation of any one of embodiments 62-65 that has a concentration of (lev)cromakalim or a pharmaceutically acceptable salt thereof of between about 1.5 mM to about 5 mM.
67. The ocular formulation of any one of embodiments 62-66 that has a concentration of (lev)cromakalim or a pharmaceutically acceptable salt thereof of between about 2 mM to about 5 mM.
68. The ocular formulation of any one of embodiments 62-67 that has a concentration of (lev)cromakalim or a pharmaceutically acceptable salt thereof of between about 2.5 mM to about 5 mM.
69. The ocular formulation of any one of embodiments 62-68 that has a concentration of (lev)cromakalim or a pharmaceutically acceptable salt thereof of between about 3 mM to about 5 mM.
70. The ocular formulation of any one of embodiments 62-69 that has a concentration of (lev)cromakalim or a pharmaceutically acceptable salt thereof of between about 3.5 mM to about 5 mM.
71. The ocular formulation of any one of embodiments 62-70 that has a concentration of (lev)cromakalim or a pharmaceutically acceptable salt thereof of between about 4 mM to about 5 mM.
72. The ocular formulation of any one of embodiments 62-71 wherein the ocular formulation consists essentially of Kolliphor® ELP, polysorbate 80, PVP, poloxamer 407, and mannitol in an aqueous formulation with a pH from about 6 to about 8.
73. The ocular formulation of any one of embodiments 62-72 wherein the ocular formulation consists of Kolliphor® ELP, polysorbate 80, PVP, poloxamer 407, and mannitol in an aqueous formulation with a pH from about 6 to about 8.
74. The ocular formulation of any one of embodiments 1-73 wherein the ocular formulation optionally comprises benzalkonium chloride (BAK) and optionally a pH adjusting agent.
75. The ocular formulation of any one of embodiments 62-71 wherein the ocular formulation consists essentially of Kolliphor® ELP, polysorbate 80, PVP, poloxamer 407, mannitol; and BAK in an aqueous formulation with a pH from about 6 to about 8.
76. The ocular formulation of any one of embodiments 62-71 wherein the ocular formulation consists of Kolliphor® ELP, polysorbate 80, PVP, poloxamer 407, mannitol; and BAK in an aqueous formulation with a pH from about 6 to about 8.
77. An ocular topical formulation that comprises (lev) cromakalim or a pharmaceutically acceptable salt thereof, Kolliphor® ELP, polysorbate 80, polyvinylpyrrolidone (PVP) K-30, poloxamer 407, mannitol, water, and phosphate buffer, and has a concentration of (lev)cromakalim or a pharmaceutically acceptable salt thereof of up to about 5 mM and is stable at ambient conditions for at least 5 months with a pH of about 6.5.
78. An ocular topical formulation of (lev)cromakalim or a pharmaceutically acceptable salt thereof that has a concentration of between about 0.01 mM to up to about 5 mM, comprises Kolliphor® ELP, polysorbate 80, polyvinylpyrrolidone (PVP) K-30, poloxamer 407, mannitol, water, and phosphate buffer, and is stable at ambient conditions for at least 5 months with a pH of about 6.5

79. An aqueous ocular topical formulation that has a concentration of (lev)cromakalim or a pharmaceutically acceptable salt thereof of between about 0.05 mM up to about 5 mM, pH from about 6 to about 8, and is stable at ambient conditions for at least 5 months and comprises glycerin, Kolliphor® ELP, polysorbate 80, poloxamer 407, hypromellose, and mannitol.

80. The ocular formulation of any one of embodiments 78 or 79, wherein the ocular formulation optionally comprises BAK and a pH adjusting agent.

81. The ocular formulation of embodiment 80 wherein the ocular formulation consists essentially of glycerin, Kolliphor® ELP, polysorbate 80, poloxamer 407, hypromellose, mannitol, and optionally benzalkonium chloride and optionally a pH adjusting agent in an aqueous formulation with a pH from about 6 to about 8.

82. The ocular topical formulation of embodiment 80 wherein the ocular formulation consists of glycerin, Kolliphor® ELP, polysorbate 80, poloxamer 407, hypromellose, mannitol, and BAK in an aqueous formulation with a pH from about 6 to about 8.

83. An ocular topical formulation of (lev)cromakalim or a pharmaceutically acceptable salt thereof that has a concentration of between about 0.05 mM to about 5 mM, pH from about 6 to about 8 and is stable at ambient conditions for at least 4 months and comprises Kolliphor® ELP, polysorbate 80, poloxamer 407, PVP K-30, mannitol, and optionally a pH adjusting agent.

84. The ocular topical formulation of embodiment 83 wherein the ocular formulation essentially consists of Kolliphor® ELP, polysorbate 80, poloxamer 407, PVP K-30, mannitol, and in an aqueous formulation with a pH from about 6 to about 8.

85. The ocular topical formulation of embodiment 83 wherein the ocular formulation consists of Kolliphor® ELP, polysorbate 80, poloxamer 407, PVP K-30, mannitol, and in an aqueous formulation with a pH from about 6 to about 8.

86. The ocular topical formulation of any one of embodiments 1-85, wherein the phosphate buffer is selected from sodium phosphate dibasic and sodium phosphate monobasic.

87. A pharmaceutical composition comprising (lev)cromakalim or a pharmaceutically acceptable salt thereof that has a concentration of (lev)cromakalim or a pharmaceutically acceptable salt thereof of between about 0.05 mM to about 5 mM, and is stable at ambient conditions for at least 4 months and comprises three or more components selected from the group consisting of a. a polyol, b. a polyethoxylated furanose fatty acid ester;

c. a nonionic tri-block copolymer of a central hydrophobic chain of polyoxypropylene flanked by two hydrophilic chains of polyoxyethylene;

d. a polymeric alkyl or aryl polyol;

e. an ethoxylated glycerol ester;

f. a polymeric lactam;

g. hydroxyalkyl cellulose;

h. an oil in water polymeric emulsifier of a block copolymer of polyacrylic acid and a hydrophobic $C_{10}$-$C_{30}$ alkyl acrylate; and i. an ethoxylated alkylphenol;

in an aqueous formulation with a pH from about 6 to about 8.

88. A topical formulation for an eye drop comprising (lev)cromakalim or a pharmaceutically acceptable salt thereof, Kolliphor® ELP, polysorbate 80, polyvinylpyrrolidone (PVP) K-30, poloxamer 407, mannitol, water, and phosphate buffer, and has a concentration of (lev)cromakalim or a pharmaceutically acceptable salt thereof of between about 0.01 mM to about 5 mM and is stable at ambient conditions for at least 5 months with a pH from about 6 to about 8.

89. The topical formulation of embodiment 88, wherein the concentration of (lev)cromakalim or a pharmaceutically acceptable salt thereof is about 0.05 mM to 5 mM.

90. The topical formulation of embodiment 88, wherein the concentration of (lev)cromakalim or a pharmaceutically acceptablediment salt thereof is about 0.1 mM to 5 mM.

91. The topical formulation of embodiment 88, wherein the concentration of (lev)cromakalim or a pharmaceutically acceptable salt thereof is about 0.5 mM to 5 mM.

92. The topical formulation of embodiment 88, wherein the concentration of (lev)cromakalim or a pharmaceutically acceptable salt thereof is about 1 mM to 5 mM 93. The topical formulation of embodiment 88, wherein the concentration of (lev)cromakalim or a pharmaceutically acceptable salt thereof is about 1.5 mM to 5 mM 94. The topical formulation of embodiment 88, wherein the concentration of (lev)cromakalim or a pharmaceutically acceptable salt thereof is about 2 mM to 5 mM 95. The topical formulation of embodiment 88, wherein the concentration of (lev)cromakalim or a pharmaceutically acceptable salt thereof is about 2.5 mM to 5 mM.

96. The topical formulation of embodiment 88, wherein the concentration of (lev)cromakalim or a pharmaceutically acceptable salt thereof is about 3 mM to 5 mM.

97. The topical formulation of embodiment 88, wherein the concentration of (lev)cromakalim or a pharmaceutically acceptable salt thereof is about 3.5 mM to 5 mM.

98. The topical formulation of embodiment 88, wherein the concentration of (lev)cromakalim or a pharmaceutically acceptable salt thereof is about 4 mM to 5 mM.

99. The topical formulation of embodiment 88, wherein the concentration of (lev)cromakalim or a pharmaceutically acceptable salt thereof is about 5 mM.

100. A topical formulation for use an eye drop comprising (lev)cromakalim or a pharmaceutically acceptable salt thereof, Kolliphor® ELP, polysorbate 80, polyvinylpyrrolidone (PVP) K-30, poloxamer 407, mannitol, water, and phosphate buffer, and has a concentration of (lev)cromakalim or a pharmaceutically acceptable salt thereof of about 0.4 mM and is stable at ambient conditions for at least 5 months with a pH of about 6.5.

101. A topical formulation that can be used as an eye drop comprising (lev)cromakalim or a pharmaceutically acceptable salt thereof, Kolliphor® ELP, polysorbate 80, polyvinylpyrrolidone (PVP) K-30, poloxamer 407, mannitol, water, and phosphate buffer, and has a concentration of (lev)cromakalim or a pharmaceutically acceptable salt thereof of about 0.8 mM and is stable at ambient conditions for at least 5 months with a pH of about 6.5.

102. A topical formulation that can be used as an eye drop comprising (lev)cromakalim or a pharmaceutically acceptable salt thereof, Kolliphor® ELP, polysorbate 80, polyvinylpyrrolidone (PVP) K-30, poloxamer 407, mannitol, water, and phosphate buffer, and has a concentration of (lev)cromakalim or a pharmaceutically acceptable salt thereof of about 2 mM and is stable at ambient conditions for at least 5 months with a pH of about 6.5.
103. The ocular topical formulation of any one of embodiments 87-102 that comprises Kolliphor® ELP at a concentration of about 5% w/v.
104. The ocular topical formulation of embodiment 103 that comprises Kolliphor® ELP at a concentration of about 4% w/v.
105. The ocular topical formulation of any one of embodiments 87-104 that comprises polysorbate 80 at a concentration of about 1% w/v.
106. The ocular topical formulation of any one of embodiments 87-105 that comprises PVP K-30 at a concentration of about 2% w/v.
107. The ocular topical formulation of any one of embodiments 87-106 that comprises poloxamer 407 at a concentration of about 0.1% w/v.
108. The ocular topical formulation of any one of embodiments 87-107 that comprises mannitol at a concentration of about 4.6% w/v.
109. The ocular topical formulation of embodiment 103 that comprises mannitol at a concentration of about 3.3%
110. A ocular topical formulation that can be used as an eye drop comprising between about 0.05 mM to about 5 mM of (lev)cromakalim, or a pharmaceutically acceptable salt thereof, in an aqueous liquid that is stable under ambient conditions for at least five months without significant crystallization or undue separation of cromakalim from the liquid and does not include DMSO, DMF or NMP or other unacceptable topical carrier for human use and has at least two excipients in addition to optional buffer.
111. A ocular topical formulation that can be used as an eye drop comprising between about 0.1 mM to about 5 mM of (lev)cromakalim, or a pharmaceutically acceptable salt thereof, in an aqueous liquid that is stable under ambient conditions for at least five months without significant crystallization or undue separation of cromakalim from the liquid and does not include DMSO, DMF or NMP or other unacceptable topical carrier for human use and has at least two excipients in addition to optional buffer.
112. A ocular topical formulation that can be used as an eye drop comprising between about 0.5 mM to about 5 mM of (lev)cromakalim, or a pharmaceutically acceptable salt thereof, in an aqueous liquid that is stable under ambient conditions for at least five months without significant crystallization or undue separation of cromakalim from the liquid and does not include DMSO, DMF or NMP or other unacceptable topical carrier for human use and has at least two excipients in addition to optional buffer.
113. The ocular topical formulation of any one of embodiments 1-112, wherein the formulation is not an emulsion.
114. The ocular topical formulation of any one of embodiments 1-112, wherein the formulation is not a gel.
115. The ocular topical formulation of any one of embodiments 1-112, wherein the formulation is not a topical gel.
116. The ocular topical formulation of any one of embodiments 1-112, wherein the formulation is a clear solution.
117. The ocular topical formulation of any one of embodiments 1-112, wherein the formulation is a micellar or nanomicellar solution.
118. The ocular topical formulation of any one of embodiments 1-112, wherein the formulation does not include an oil as specifically defined above.
119. The ocular topical formulation of any one of embodiments 1-118, wherein the formulation has a percent transmittance of greater than 85% when tested with a UV-Vis spectrophotometer.
120. The ocular topical formulation of any one of embodiments 1-118, wherein the formulation has a percent transmittance of greater than 90% when tested with a UV-Vis spectrophotometer.
121. The ocular topical formulation of any one of embodiments 1-118, wherein the formulation has a percent transmittance of greater than 95% when tested with a UV-Vis spectrophotometer.
122. The ocular topical formulation of any one of embodiments 1-121, wherein the formulation comprises levcromakalim.
123. The ocular topical formulation of any one of embodiments 1-121, wherein the formulation comprises cromakalim.
124. A method for the treatment of an ocular disorder affecting the anterior or the posterior segment of the eye comprising administering an effective amount of (lev) cromakalim or a pharmaceutically acceptable salt thereof in a topical ocular formulation of any one of embodiments 1-123 to a host in need thereof.
125. The method of embodiment 124, wherein the host is human.
126. The method of embodiments 124, wherein the use of the topical formulation results in lower intraocular pressure.
127. The method of embodiment 124 wherein the ocular disorder is glaucoma.
128. The method of embodiment 127, wherein the glaucoma is glaucoma associated with normal intraocular pressure or normal tension glaucoma (NTG).
129. The method of embodiment 127 wherein the glaucoma is glaucoma associated with elevated intraocular pressure selected from the group primary open angle glaucoma (POAG), primary angle closure glaucoma (also known as chronic open angle glaucoma, chronic simple glaucoma and glaucoma simplex), pediatric glaucoma, pseudo-exfoliative glaucoma, pigmentary glaucoma, traumatic glaucoma, neovascular glaucoma, irido corneal endothelial glaucoma (ICE), uveitic glaucoma, glaucoma associated with diabetic retinopathy, Sturge, Weber Syndrome, steroid induced glaucoma, and acute glaucoma resulting from advanced cataracts and/or from intravitreal injections.
130. The method of embodiment 129, wherein the ocular disorder is Sturge Weber Syndrome or glaucoma induced by Sturge Weber Syndrome-induced glaucoma.
131. The method of embodiment 129, wherein the ocular disorder is diabetic retinopathy.
132. The method of embodiment 129, wherein the topical treatment is a primary or secondary or adjunctive treatment as part of the protocol for MIGS (Microinvasive Glaucoma Surgery), selected from the group consisting of miniature versions of trabeculectomy (microtrabeculectomies), trabecular bypass surgeries, totally internal or suprachoroidal shunts, milder/gentler versions of laser cyclo photocoagulation, and in alternative embodiments, Schlemm's canal stents that dilate Schlemm's canal, goniotomies, canaloplasties, and laser trabeculoplasties.

133. The method of embodiment 129, wherein the ocular disorder is Graves' ophthalmopathy, thyroid-associated orbitopathy (TAO), Graves' orbitopathy (GO), retrobulbar tumors, cavernous sinus thrombosis, orbital vein thrombosis, episcleral/orbital vein vasculitis, superior vena cava obstruction, superior vena cava thrombosis, carotid cavernous sinus fistula, dural cavernous sinus shunts, orbital varices, central retinal vein occlusion (CRVO), branch retinal vein occlusion (BRVO), artery occlusive/embolic-hypoperfusion diseases, or optic nerve damage due to ischemia (posterior and anterior ischemic optic neuropathy (NAION).

134. The method of embodiment 129 wherein the treatment with topical formulation provides cellular protection and/or neuroprotection to a host in need thereof.

135. Use of (lev)cromakalim or a pharmaceutically acceptable salt thereof as a formulation of any of the embodiments 1-123 in the manufacture of medicament to topically treat an ocular disorder in a host in need thereof.

136. The use of embodiment 135 wherein the ocular disorder is glaucoma.

137. The use of embodiment 136, wherein the glaucoma is glaucoma associated with normal intraocular pressure or normal tension glaucoma (NTG).

138. The use of embodiment 136 wherein the glaucoma is glaucoma associated with elevated intraocular pressure selected from the group primary open angle glaucoma (POAG), primary angle closure glaucoma (also known as chronic open angle glaucoma, chronic simple glaucoma and glaucoma simplex), pediatric glaucoma, pseudo-exfoliative glaucoma, pigmentary glaucoma, traumatic glaucoma, neovascular glaucoma, irido corneal endothelial glaucoma (ICE), uveitic glaucoma, glaucoma associated with diabetic retinopathy, Sturge, Weber Syndrome, steroid induced glaucoma, and acute glaucoma resulting from advanced cataracts and/or from intravitreal injections.

139. The use of embodiment 138, wherein the ocular disorder is Sturge Weber Syndrome or glaucoma induced by Sturge Weber Syndrome-induced glaucoma.

140. The use of embodiment 138, wherein the ocular disorder is diabetic retinopathy.

141. The use of embodiment 138, wherein the topical treatment is a primary or secondary or adjunctive treatment as part of the protocol for MIGS (Microinvasive Glaucoma Surgery), selected from the group consisting of miniature versions of trabeculectomy (microtrabeculectomies), trabecular bypass surgeries, totally internal or suprachoroidal shunts, milder/gentler versions of laser cyclo photocoagulation, and in alternative embodiments, Schlemm's canal stents that dilate Schlemm's canal, goniotomies, canaloplasties, and laser trabeculoplasties.

142. The use of embodiment 138, wherein the ocular disorder is Graves' ophthalmopathy, thyroid-associated orbitopathy (TAO), Graves' orbitopathy (GO), retrobulbar tumors, cavernous sinus thrombosis, orbital vein thrombosis, episcleral/orbital vein vasculitis, superior vena cava obstruction, superior vena cava thrombosis, carotid cavernous sinus fistula, dural cavernous sinus shunts, orbital varices, central retinal vein occlusion (CRVO), branch retinal vein occlusion (BRVO), artery occlusive/embolic-hypoperfusion diseases, or optic nerve damage due to ischemia (posterior and anterior ischemic optic neuropathy (NAION).

143. The use of embodiment 138 wherein the treatment with topical formulation provides cellular protection and/or neuroprotection to a host in need thereof.

144. An ocular topical formulation comprising (lev)cromakalim or a pharmaceutically acceptable salt thereof (0.015% w/v), Kolliphor® ELP (4% w/v), polysorbate 80 (1% w/v), polyvinylpyrrolidone (PVP) K-30 (2% w/v), poloxamer 407 (0.1% w/v), mannitol (3.3% w/v), sodium phosphate dibasic buffer, sodium phosphate monobasic buffer, and water, with a pH of about 6.5.

145. An ocular topical formulation comprising (lev)cromakalim or a pharmaceutically acceptable salt thereof (0.03% w/v), Kolliphor® ELP (4% w/v), polysorbate 80 (1% w/v), polyvinylpyrrolidone (PVP) K-30 (2% w/v), poloxamer 407 (0.1% w/v), mannitol (3.3% w/v), sodium phosphate dibasic buffer, sodium phosphate monobasic buffer, and water, with a pH of about 6.5.

146. An ocular topical formulation comprising (lev)cromakalim or a pharmaceutically acceptable salt thereof (0.075% w/v), Kolliphor® ELP (4% w/v), polysorbate 80 (1% w/v), polyvinylpyrrolidone (PVP) K-30 (2% w/v), poloxamer 407 (0.1% w/v), mannitol (3.3% w/v), sodium phosphate dibasic buffer, sodium phosphate monobasic buffer, and water, with a pH of about 6.5.

147. Use of (lev)cromakalim or a pharmaceutically acceptable salt thereof as a formulation of any of the embodiments 1-123 to topically treat an ocular disorder in a host in need thereof.

148. The use of embodiment 147 wherein the ocular disorder is glaucoma.

149. The use of embodiment 148, wherein the glaucoma is glaucoma associated with normal intraocular pressure or normal tension glaucoma (NTG).

150. The use of embodiment 148 wherein the glaucoma is glaucoma associated with elevated intraocular pressure selected from the group primary open angle glaucoma (POAG), primary angle closure glaucoma (also known as chronic open angle glaucoma, chronic simple glaucoma and glaucoma simplex), pediatric glaucoma, pseudo-exfoliative glaucoma, pigmentary glaucoma, traumatic glaucoma, neovascular glaucoma, irido corneal endothelial glaucoma (ICE), uveitic glaucoma, glaucoma associated with diabetic retinopathy, Sturge, Weber Syndrome, steroid induced glaucoma, and acute glaucoma resulting from advanced cataracts and/or from intravitreal injections.

151. The use of embodiment 147, wherein the ocular disorder is Sturge Weber Syndrome or glaucoma induced by Sturge Weber Syndrome-induced glaucoma.

152. The use of embodiment 147, wherein the ocular disorder is diabetic retinopathy.

153. The use of embodiment 147, wherein the topical treatment is a primary or secondary or adjunctive treatment as part of the protocol for MIGS (Microinvasive Glaucoma Surgery), selected from the group consisting of miniature versions of trabeculectomy (microtrabeculectomies), trabecular bypass surgeries, totally internal or suprachoroidal shunts, milder/gentler versions of laser cyclo photocoagulation, and in alternative embodiments, Schlemm's canal stents that dilate Schlemm's canal, goniotomies, canaloplasties, and laser trabeculoplasties.

154. The use of embodiment 147, wherein the ocular disorder is Graves' ophthalmopathy, thyroid-associated orbitopathy (TAO), Graves' orbitopathy (GO), retrobulbar tumors, cavernous sinus thrombosis, orbital vein thrombosis, episcleral/orbital vein vasculitis, superior vena cava obstruction, superior vena cava thrombosis, carotid cavernous sinus fistula, dural cavernous sinus shunts, orbital varices, central retinal vein occlusion (CRVO), branch retinal vein occlusion (BRVO), artery occlusive/embolic-hypoperfusion diseases, or optic nerve damage due to ischemia (posterior and anterior ischemic optic neuropathy (NAION).

155. The use of embodiment 147 wherein the treatment with topical formulation provides cellular protection and/or neuroprotection to a host in need thereof.

156. A (lev)cromakalim or a pharmaceutically acceptable salt thereof topical formulation of any of the embodiments 1-123 for use in the treatment of an ocular disorder in a host in need thereof.

157. The use of embodiment 156 wherein the ocular disorder is glaucoma.

158. The use of embodiment 156, wherein the glaucoma is glaucoma associated with normal intraocular pressure or normal tension glaucoma (NTG).

159. The use of embodiment 156 wherein the glaucoma is glaucoma associated with elevated intraocular pressure selected from the group primary open angle glaucoma (POAG), primary angle closure glaucoma (also known as chronic open angle glaucoma, chronic simple glaucoma and glaucoma simplex), pediatric glaucoma, pseudo-exfoliative glaucoma, pigmentary glaucoma, traumatic glaucoma, neovascular glaucoma, irido corneal endothelial glaucoma (ICE), uveitic glaucoma, glaucoma associated with diabetic retinopathy, Sturge, Weber Syndrome, steroid induced glaucoma, and acute glaucoma resulting from advanced cataracts and/or from intravitreal injections.

160. The use of embodiment 156, wherein the ocular disorder is Sturge Weber Syndrome or glaucoma induced by Sturge Weber Syndrome-induced glaucoma.

161. The use of embodiment 156, wherein the ocular disorder is diabetic retinopathy.

162. The use of embodiment 156, wherein the topical treatment is a primary or secondary or adjunctive treatment as part of the protocol for MIGS (Microinvasive Glaucoma Surgery), selected from the group consisting of miniature versions of trabeculectomy (microtrabeculectomies), trabecular bypass surgeries, totally internal or suprachoroidal shunts, milder/gentler versions of laser cyclo photocoagulation, and in alternative embodiments, Schlemm's canal stents that dilate Schlemm's canal, goniotomies, canaloplasties, and laser trabeculoplasties.

163. The use of embodiment 156, wherein the ocular disorder is Graves' ophthalmopathy, thyroid-associated orbitopathy (TAO), Graves' orbitopathy (GO), retrobulbar tumors, cavernous sinus thrombosis, orbital vein thrombosis, episcleral/orbital vein vasculitis, superior vena cava obstruction, superior vena cava thrombosis, carotid cavernous sinus fistula, dural cavernous sinus shunts, orbital varices, central retinal vein occlusion (CRVO), branch retinal vein occlusion (BRVO), artery occlusive/embolic-hypoperfusion diseases, or optic nerve damage due to ischemia (posterior and anterior ischemic optic neuropathy (NAION).

164. The use of embodiment 156 wherein the treatment with topical formulation provides cellular protection and/or neuroprotection to a host in need thereof.

VI. General Synthesis of (lev)cromakalim

The following is a general synthesis of (lev)cromakalim.

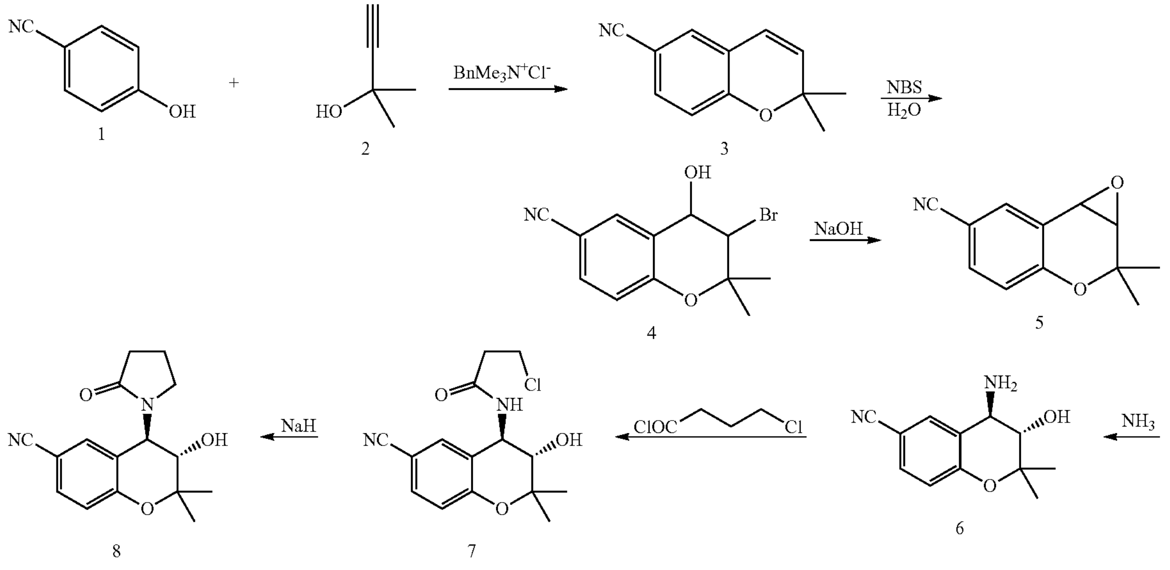

Reaction of 4-cyanophenol (4-Hydroxybenzonitrile) with 2-hydroxy-2-methyl-3-butyne under phase transfer catalyst probably proceeds to initial formation of a propargyl carbocation. The course of the reaction can be envisaged by assuming that this then attacks the aromatic ring; the resulting allylic cation can then capture the adjacent phenol oxygen and thus form the observed product (3). Treatment of that product with aqueous N-bromosuccinimide leads to the addition of the elements of hypobromous acid and formation of the bromohydrin (4) as a mixture of the trans enantiomers. This cyclizes to the epoxide 5 in the presence of sodium hydroxide (5). Ring opening of the oxirane with ammonia gives a mixture of the trans amino alcohols (6). These are probably resolved at this stage and the 3S,4R-enantiomer used in the next stage. That isomer is next acylated with 4-chrlorobutyl chloride to give the chloroamide (7). The anion from reaction of the amide with sodium hydride then displaces the chlorine on the end of the chain to form the pyrrolidine ring. There is thus obtained levcromakalim (8).

VII. Nonlimiting Illustrative Processes of Manufacture of (Lev)cromakalim Formulations of the Present Invention The ocular topical (lev)cromakalim formulations of the present invention can be prepared according to a variety of processes to achieve the desired results. In certain embodiments, the ocular topical (lev)cromakalim formulation is prepared using a process wherein (lev)cromakalim and the other components are first individually or in groups dissolved in ethanol or other low volatile organic solvent(s), mixed and then evaporated under vacuum to produce a film, which is then resuspended in phosphate buffer and/or deionized water, homogenized or mixed, which is then incubated and filtered to yield the formulation. Optionally, the resuspension can be autoclaved and optionally filtered.

In certain embodiments, the ocular formulation is prepared by dissolving (lev)cromakalim in a volatile solvent, followed by evaporation and drying under high vacuum to obtain a dry residue, which is then resuspended into combined aqueous solutions of excipients, then incubated, and filtered to yield the formulation. Optionally, the resuspension can be autoclaved and filtered.

In certain aspects of the specific embodiments, therapeutic levels of (lev)cromakalim in ocular topical formulations of the present invention can be achieved via the encapsulation of (lev)cromakalim into nanomicelles using a variety of processes. In certain embodiments, the nanomicellar formulations of (lev)cromakalim can be prepared using a 2-step encapsulation process. First, the base formulation of (lev) cromakalim and non-aqueous excipients are separately dissolved in ethanol or other compatible low volatile organic solvent(s). These solutions are combined in a glass round-bottom flask, vortexed or stirred to form a homogenous solution, and the solvent removed by rotary evaporation followed by high vacuum to produce a thin film. The film is then hydrated with double distilled water, aqueous excipients, and phosphate buffer and/or deionized water, homogenized or mixed, incubated, and then filtered through a 0.22 μm filter to yield the final formulation. Optionally, the fully hydrated formula can be autoclaved prior to filtration.

In certain embodiments, the ocular topical (lev)cromakalim formulation is prepared by direct dissolution in which a solution of (lev)cromakalim in ethanol is added to a vial or centrifuge, and the ethanol removed under vacuum to leave a fine solid coating. Aqueous solutions of excipients are then individually added to the dried (lev)cromakalim with rapid stirring, sonication, or homogenization. The solution is optionally autoclaved and then filtered through a 0.22 μm filter to yield the final formulation.

In certain embodiments, the nanomicellar formulations of (lev)cromakalim are prepared using the dialysis method which uses semipermeable membranes to selectively allow certain molecules to pass through. A solution of (lev)cromakalim and excipients is prepared in a water-miscible organic solvent and loaded into a dialysis bag, which is then submerged in a larger volume of deionized water. During this process the organic solvent is replaced by water which induces formation of micelles with entrapment of (lev) cromakalim. Unincorporated excipients and unloaded (lev) cromakalim will then diffuse out of the bag into the surrounding solution over time.

In certain embodiments, the volatile solvent used to dissolve (lev)cromakalim is selected from the group of acetonitrile, acetone, methylene chloride, chloroform, methanol, propanol, or other alcohol or ether-based solvents. Other solvents can be used that do not impart undue toxicity to the final product or leave an unacceptable residue.

In certain embodiments, the ocular formulation is homogenized or mixed through techniques including but not limited to heating, centrifuging, filtering, incubating, vortexing, standing, stirring, shaking, sonicating, or any combination thereof.

In certain embodiments, (lev)cromakalim formulation as described herein is an emulsion or a solution formed by stirring at the temperature of at least about 120° C., at least about 100° C., at least about 80° C., at least about 60° C., at least about 40° C., or at least about ambient temperature.

In certain embodiments, the ocular formulation can be formed by mixing the components together (which may have each or together been prior dissolved in a low volatile solvent including but not limited to ethanol) and then heating to remove the solvents, wherein the heat can include autoclave. In certain embodiments, the ocular formulation can be formed by heating the solution or the emulsion with a heating block.

In certain aspects of the embodiments, the present invention provides a solution or an emulsion wherein the undissolved components are removed by centrifugation at the speed of at least about 1000 rpm, at least about 1250 rpm, at least about 1500 rpm, at least about 1800 rpm, at least about 2000 rpm, at least about 2500 rpm, and at least about 3000 rpm.

In certain embodiments, the present invention provides a solution or an emulsion which is filtered using a filter of the pore size of at least about 0.2 μm, at least about 0.45 μm, at least about 0.7 μm, and at least about 1.2 μm. In certain nonlimiting embodiments the filter membrane may be made of nylon, polytetrafluoroethylene, or PTFE, polyvinylidene difluoride or PVDF, polyethersulfone or PES, cellulose acetate or CA, polypropylene, or PP, and/or glass fiber.

Concentrations of (lev)cromakalim in formulations described herein, can be extrapolated using the standard curve method. Table 1 shows the concentration of levcromakalim standards and measurement of area of the peak which indicates elution of levcromakalim. FIG. 4 shows the resulting levcromakalim standard curve using plotted as concentration vs area.

TABLE 1

HPLC measurements to plot Area vs Standard concentration

| Standard | Peak Area | | | | Concentration |
|---|---|---|---|---|---|
| Conc [mM] | 1 | 2 | 3 | Avg | (mg/mL) |
| 5 | 4.555 | 4.296062 | 5.257081 | 4.702714 | 1.43 |
| 2.5 | 2.282 | 2.324636 | 2.655283 | 2.42064 | 0.715 |

TABLE 1-continued

| HPLC measurements to plot Area vs Standard concentration | | | | | |
|---|---|---|---|---|---|
| Standard | Peak Area | | | | Concentration |
| Conc [mM] | 1 | 2 | 3 | Avg | (mg/mL) |
| 1.25 | 1.054 | 1.336725 | 1.277846 | 1.222857 | 0.3575 |
| 0.75 | 0.541 | 0.558182 | 0.692308 | 0.597163 | 0.2145 |

The following examples are provided to further illustrate aspects of the invention, which include non-limiting examples of (lev)cromakalim formulations with concentrations of <1 mg/mL, 1-1.5 mg/mL, and >1.5 mg/mL and their manufacture. These illustrative examples are non-limiting and should not be constructed as limiting any aspect of the invention.

Definitions

PBS Stock Solution: phosphate buffered saline was prepared with the concentration of NaCl: 1.37 M KCl: 27 mM $Na_2HPO_4$: 100 mM $KH_2PO_4$: 18 mM Stock Phosphate Non-Saline Buffer solution: non-saline phosphate buffer was prepared with the concentration of $Na_2HPO_4$: 70 mM $NaH_2PO_4$: 25 mM

Example 1—Ocular Formulations of Levcromakalim at the Concentration of <1 mg/mL or <3.5 mM

Example 1a

| Formula 1a | |
|---|---|
| Component | % Conc. |
| levcromakalim | 0.2% |
| PBS Stock Solution | 10% |
| deionized $H_2O$ | 89.8% |

A solution of levcromakalim in acetonitrile (0.6%) was added to a 5 mL vial. The solvent was removed via evaporation under a stream of nitrogen, and vial was placed under high vacuum for 24 hours for further evaporation resulting in a thin film. The film was then hydrated with 2 ml of deionized $H_2O$. 300 μL of PBS Stock Solution was then added, and the final volume was brought to 3 mL using deionized $H_2O$. The mixture was stirred with heat at 80° C. for 20 minutes. Then, the mixture was incubated at room temperature overnight and filtered through a 0.45 μm filter to provide a saturated solution. Levcromakalim concentration measured using the standard curve method was about 0.38 mg/mL or 1.3 mM.

Example 1b

| Formula 1b | |
|---|---|
| Component | % Conc. |
| levcromakalim | 0.2% |
| polysorbate 80 | 1% |
| PBS Stock Solution | 10% |
| deionized $H_2O$ | 88.8% |

A solution of leveromakalim in acetonitrile (0.6%) was added to a 5 mL vial. The solvent was removed via evaporation under a stream of nitrogen, and then the vial was placed under high vacuum for 24 hours for further evaporation resulting in a thin film. 300 μL of PBS Stock Solution and polysorbate 80 were then added, and the final volume was brought to 3 mL using deionized $H_2O$ such that the concentration of polysorbate 80 was about 1%. The mixture was stirred in a heating block at 80° C. for 20 minutes. Then, the mixture was incubated at room temperature overnight and then filtered through a 0.45 μm filter to provide a saturated solution. Levcromakalim concentration measured using the standard curve method was about 0.46 mg/mL or 1.6 mM.

Example 1c

| Formula 1c | |
|---|---|
| Component | % Conc. |
| levcromakalim | 0.2% |
| glycerin | 5% |
| PBS Stock Solution | 10% |
| deionized $H_2O$ | 84.8% |

A solution of levcromakalim in acetonitrile (1 mL of 6 mg/mL stock) was added to a 5 mL vial. The solvent was removed via evaporation under a stream of nitrogen, and then the vial was placed under high vacuum for 24 hours for further evaporation resulting in a thin film. 300 μL of PBS Stock Solution and glycerin were then added, and the final volume was brought to 3 mL using deionized $H_2O$ such that the concentration of glycerin was about 5%. The mixture was stirred in a heating block at 80° C. for 20 minutes. Then, the mixture was incubated at room temperature overnight and then filtered through a 0.45 μm filter to provide a saturated solution. Levcromakalim concentration measured using the standard curve method was about 0.34 mg/mL or 1.2 mM.

Example 1d

| Formula 1d | |
|---|---|
| Component | % Conc. |
| levcromakalim | 0.2% |
| poloxamer 407 | 0.1% |

-continued

| Formula 1d | |
|---|---|
| Component | % Conc. |
| PBS Stock Solution | 10% |
| deionized $H_2O$ | 89.7% |

A solution of leveromakalim in acetonitrile (1 mL of 6 mg/mL stock) was added to a 5 mL vial. The solvent was removed via evaporation under a stream of nitrogen, and then the vial was placed under high vacuum for 24 hours for further evaporation resulting in a thin film. 300 μL of PBS Stock Solution, and poloxamer 407 were then added. The final volume was brought to 3 mL using deionized $H_2O$ such that the concentration of poloxamer 407 was about 0.1%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 0.37 mg/mL or 1.3 mM.

Example 1e

| Formula 1e | |
|---|---|
| Component | % Conc. |
| levcromakalim | 0.2% |
| Tyloxapol | 0.1% |
| PBS Stock Solution | 10% |
| deionized $H_2O$ | 89.7% |

A solution of levcromakalim in acetonitrile (1 mL of 6 mg/mL stock) was added to a 5 mL vial. The solvent was removed via evaporation under a stream of nitrogen, and then the vial was placed under high vacuum for 24 hours for further evaporation resulting in a thin film. 300 μL of PBS Stock Solution, and tyloxapol were then added. The final volume was brought to 3 mL using deionized $H_2O$ such that the concentration of Tyloxapol was about 0.1%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 0.38 mg/mL or 1.3 mM.

Example 1f

| Formula 1f | |
|---|---|
| Component | % Conc. |
| levcromakalim | 0.2% |
| Kolliphor ® ELP | 5% |
| PBS Stock Solution | 10% |
| deionized $H_2O$ | 84.8% |

A solution of levcromakalim in acetonitrile (1 mL of 6 mg/mL stock) was added to a 5 mL vial. The solvent was removed via evaporation under a stream of nitrogen, and then the vial was placed under high vacuum for 24 hours for further evaporation resulting in a thin film. 300 μL of PBS Stock Solution and Kolliphor® ELP were then added. The final volume was brought to 3 mL using deionized $H_2O$ such that the concentration of Kolliphor® ELP was about 5%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 0.39 mg/mL 1.4 mM.

Example 1g

| Formula 1g | |
|---|---|
| Component | % Conc. |
| levcromakalim | 0.2% |
| Kolliphor ® RH 40 | 3% |
| Premulen ™ TR-1 | 0.2% |
| deionized $H_2O$ | 96.6% |

A solution of levcromakalim in ethanol (1 mL of 6 mg/mL stock); and EtOH-based solutions of Kolliphor® RH 40, and Premulen™ TR-1 were combined in a 5 mL vial. The solvent was removed via evaporation under a stream of nitrogen, and the vial was placed under high vacuum for 24 hours for further evaporation resulting in a thin film. The final volume was brought to 3 mL using deionized $H_2O$ such that the concentration of Kolliphor® RH 40 was about 2%, and Premulen™ TR-1 was about 0.2%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 0.59 mg/mL or 2.1 mM.

Example 1h

| Formula 1h | |
|---|---|
| Component | % Conc. |
| levcromakalim | 0.2% |
| hypromellose | 0.5% |
| PBS Stock Solution | 10% |
| deionized $H_2O$ | 89.3% |

A solution of levcromakalim in acetonitrile (1 mL of 6 mg/mL stock) was added to a 5 mL vial. The solvent was removed via evaporation under a stream of nitrogen, and the vial was placed under high vacuum for 24 hours for further evaporation resulting in a thin film. 300 μL of PBS Stock Solution, and hypromellose were then added, and final volume was brought to 3 mL using deionized $H_2O$ such that the concentration of hypromellose was about 0.5%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 0.7 mg/mL or 2.4 mM.

Example 1i

| Formula 1i | |
|---|---|
| Component | % Conc. |
| levcromakalim | 0.2% |
| polysorbate 80 | 1% |
| glycerin | 5% |
| EDTA | 0.1% |
| deionized $H_2O$ | 94.7% |

A solution of leveromakalim in acetonitrile (1 mL of 6 mg/mL stock) was aliquoted to a 5 mL vial. The solvent was removed via evaporation under a stream of nitrogen, and the vial was placed under high vacuum for 24 hours for further evaporation resulting in a thin film. Water-based solutions of polysorbate 80, glycerin, and EDTA were then added; and the final volume was brought to 3 mL using deionized $H_2O$ such that the concentration of polysorbate 80 was about 1%, glycerin was about 5%, and EDTA was about 0.1%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 0.43 mg/mL or 1.5 mM.

Example 1j

| Formula 1j | |
|---|---|
| Component | % Conc. |
| levcromakalim | 0.2% |
| tyloxapol | 2% |
| polysorbate 80 | 5% |
| hypromellose | 0.1% |
| deionized $H_2O$ | 92.7% |

A solution of levcromakalim in ethanol (1 mL of 6 mg/mL stock), and EtOH-based solutions of tyloxapol, polysorbate 80, and Hypromellose were combined in a 5 mL vial. The solvent was removed via evaporation under a stream of nitrogen, and the vial was placed under high vacuum for 24 hours for further evaporation resulting in a thin film. The final volume was brought to 3 mL using deionized $H_2O$ such that the concentration of tyloxapol was about 2%, polysorbate 80 was about 5%, and hypromellose was about 0.1%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 0.89 mg/mL or 3.1 mM.

Example 1k

-continued

| Formula 1k | |
|---|---|
| Component | % Conc. |
| levcromakalim | 0.2% |
| Kolliphor ® ELP | 2% |
| polysorbate 80 | 1% |
| Premulen ™ TR-1 | 0.2% |
| deionized $H_2O$ | 96.6% |

A solution of leveromakalim in ethanol (1 mL of 6 mg/mL stock), and EtOH-based solutions of Kolliphor® ELP, polysorbate 80, and Premulen™ TR-1 were combined in a 5 mL vial. The solvent was removed via evaporation under a stream of nitrogen, and the vial was placed under high vacuum for 24 hours for further evaporation resulting in a thin film. The final volume was brought to 3 mL using deionized $H_2O$ such that the concentration of Kolliphor® ELP was about 2%, polysorbate 80 was about 1%, and Premulen™ TR-1 was about 0.2%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 0.79 mg/mL or 2.8 mM.

Example 1l

| Formula 1l | |
|---|---|
| Component | % Conc. |
| levcromakalim | 0.2% |
| Kolliphor ® ELP | 2% |
| polysorbate 80 | 1% |
| Premulen ™ TR-2 | 0.2% |
| deionized $H_2O$ | 96.6% |

A solution of levcromakalim in ethanol (1 mL of 6 mg/mL stock), and EtOH-based solutions of Kolliphor® ELP, polysorbate 80, Premulen™ TR-2 were combined in a 5 mL vial. The solvent was removed via evaporation under a stream of nitrogen, and the vial was placed under high vacuum for 24 hours for further evaporation resulting in a thin film. The final volume was brought to 3 mL using deionized $H_2O$ such that the concentration of Kolliphor® ELP was about 2%, polysorbate 80 was about 1%, and Premulen™ TR-2 was about 0.2%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 0.68 mg/mL or 2.4 mM.

Example 1m

| Formula 1m | |
|---|---|
| Component | % Conc. |
| levcromakalim | 0.2% |
| glycerin | 5% |
| Kolliphor ® ELP | 5% |
| polysorbate 80 | 1% |
| hypromellose | 0.5% |

-continued

| Formula 1m | |
|---|---|
| Component | % Conc. |
| PBS Stock Solution | 10% |
| deionized $H_2O$ | 78.3% |

A solution of levcromakalim in acetonitrile (0.6%) was combined with EtOH-based solutions of glycerin, Kolliphor® ELP, polysorbate 80, and hypromellose. The solvent was removed by evaporation under a stream of nitrogen and drying under high vacuum for 24 hours to provide a thin film. 300 μL of PBS Stock Solution was added and the volume was adjusted with deionized $H_2O$ such that the concentration of glycerin was about 5%, Kolliphor® ELP was about 5%, polysorbate 80 was about 1%, and hypromellose was about 0.5%. The film was dissolved or suspended with rapid stirring or sonication. Levcromakalim concentration measured using the standard curve method was about 0.5 mg/mL or 1.7 mM.

Example 1n

| Formula 1n | |
|---|---|
| Component | % Conc. |
| levcromakalim | 0.2% |
| glycerin | 2.2% |
| castor oil | 1.25% |
| polysorbate 80 | 1% |
| Premulen ™ TR-1 | 0.05% |
| PBS Stock Solution | 10% |
| deionized $H_2O$ | 85.3% |

A solution of levcromakalim in ethanol (1 mL of 6 mg/mL stock) was combined with the EtOH-based solutions of glycerin, castor oil, polysorbate 80, and Premulen™ TR-1 aliquoted into a 5 mL vial. The solvent was removed via evaporation under a stream of nitrogen, and the vial was placed under high vacuum for 24 hours for further evaporation resulting in a thin film. 300 μL of PBS Stock Solution was then added, and the final volume was brought to 3 mL using deionized $H_2O$ such that the concentration of glycerin was about 2.2%, castor oil was about 1.25%, polysorbate 80 was about 1%, and Premulen™ TR-1 was about 0.05%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 0.56 mg/mL or 2 mM.

Example 1o

| Formula 1o | |
|---|---|
| Component | % Conc. |
| levcromakalim | 0.2% |
| NaCMC | 0.5% |
| PBS Stock Solution | 10% |
| deionized $H_2O$ | 89.3% |

A solution of levcromakalim in acetonitrile (1 mL of 6 mg/mL stock) was added to a 5 mL vial. The solvent was removed via evaporation under a stream of nitrogen, and then the vial was placed under high vacuum for 24 hours for further evaporation resulting in a thin film. 300 μL of PBS Stock Solution and sodium carboxymethylcellulose (NaCMC) were then added. The final volume was brought to 3 mL using deionized $H_2O$ such that the concentration of NaCMC was about 0.5%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 0.99 mg/mL or 3.4 mM.

Example 2—Ocular Formulations of Levcromakalim at the Concentration of 1-1.5 mg/mL or 3.5-5.2 mM Example 2a

| Formula 2a | |
|---|---|
| Component | % Conc. |
| levcromakalim | 0.2% |
| glycerin | 4% |
| Kolliphor ® ELP | 2% |
| polysorbate 80 | 1% |
| poloxamer 407 | 0.1% |
| hypromellose | 0.1% |
| Stock Phosphate Non-Saline Buffer solution | 10% |
| mannitol | 3.5% |
| BAK | 0.02% |
| deionized $H_2O$ | 79.08% |

A solution of levcromakalim in acetonitrile (0.6%) was added to a 3 mL vial. The solvent was removed by evaporation under a stream of nitrogen and drying under high vacuum for 24 hours to provide a thin film. 300 μL of the Stock Phosphate Non-Saline Buffer solution, and the water-based solutions of components were then added to dissolve or suspend the film with rapid stirring or sonication, which provided the formulation such that the concentration of glycerin was about 4%, Kolliphor® ELP was about 2%, polysorbate 80 was about 1%, poloxamer 407 was about 0.1%, hypromellose was about 0.1%, mannitol was about 3.5%, and benzalkonium chloride was about 0.02%. Levcromakalim concentration measured using the standard curve method was about 1.36 mg/mL or 4.7 mM.

Example 2b

| Formula 2b | |
|---|---|
| Component | % Conc. |
| levcromakalim | 0.2% |
| Kolliphor ® RH 40 | 2% |
| octoxynol-40 | 1% |
| Premulen ™ TR-2 | 0.2% |
| deionized $H_2O$ | 96.6% |

A solution of leveromakalim in ethanol (1 mL of 6 mg/mL stock), and EtOH-based solutions of Kolliphor® RH 40, octoxynol-40, and Premulen™ TR-2 were combined in a 5 mL vial. The solvent was removed via evaporation under a stream of nitrogen, and the vial was placed under high vacuum for 24 hours for further evaporation resulting in a thin film. The final volume was brought to 3 mL using deionized $H_2O$ such that the concentration of Kolliphor® RH 40 was about 2%, octoxynol-40 was about 1%, and Premulen™ TR-2 was about 0.2%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 1.23 mg/mL or 4.3 mM.

Example 2c

Formula 2c

| Component | % Conc. |
|---|---|
| levcromakalim | 0.2% |
| Kolliphor ® RH 40 | 5% |
| Kolliphor ® HS 15 | 1% |
| PVP | 2% |
| deionized $H_2O$ | 91.8% |

A solution of levcromakalim in ethanol (1 mL of 6 mg/mL stock), and EtOH-based solutions of Kolliphor® RH 40, Kolliphor® HS 15, and PVP were combined in a 5 mL vial. The solvent was removed via evaporation under a stream of nitrogen, and the vial was placed under high vacuum for 24 hours for further evaporation resulting in a thin film. The final volume was brought to 3 mL using deionized $H_2O$ such that the concentration of Kolliphor® RH 40 was about 5%, Kolliphor® HS 15 was about 1%, and PVP was about 2%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 1.17 mg/mL or 4.1 mM.

Example 2d

Formula 2d

| Component | % Conc. |
|---|---|
| levcromakalim | 0.2% |
| glycerin | 5% |
| Kolliphor ® ELP | 5% |
| polysorbate 80 | 1% |
| hypromellose | 0.05% |
| deionized $H_2O$ | 89.75% |

A solution of levcromakalim in acetonitrile (1 mL of 6 mg/mL stock) was added to a 5 mL vial. The solvent was removed via evaporation under a stream of nitrogen, and the vial was placed under high vacuum for 24 hours for further evaporation resulting in a thin film. Water-based solutions of glycerin, Kolliphor® ELP, polysorbate 80, hypromellose were then added, and final volume was brought to 3 mL using deionized $H_2O$ such that the concentration of glycerin was about 5%, Kolliphor® ELP was about 5%, polysorbate 80 was about 1%, and hypromellose was about 0.05%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 1.31 mg/mL or 4.6 mM.

Example 2e

Formula 2e

| Component | % Conc. |
|---|---|
| levcromakalim | 0.2% |
| Kolliphor ® ELP | 5% |
| polysorbate 80 | 1% |
| PVP | 2% |
| Stock Phosphate Non-Saline Buffer solution | 10% |
| deionized $H_2O$ | 81.8% |

A solution of levcromakalim in ethanol (1 mL of 6 mg/mL stock), and EtOH-based solutions of Kolliphor® ELP, polysorbate 80, PVP was added to a 5 mL vial. The solvent was removed via evaporation under a stream of nitrogen, and the vial was placed under high vacuum for 24 hours for further evaporation resulting in a thin film. 300 μL of the Stock Phosphate Non-Saline Buffer solution was then added, and the final volume was brought to 3 mL using deionized $H_2O$ such that the concentration of Kolliphor® ELP was about 5%, polysorbate 80 was about 1%, and PVP was about 2%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 1.1 mg/mL or 4 mM.

Example 2f

Formula 2f

| Component | % Conc. |
|---|---|
| levcromakalim | 0.2% |
| glycerin | 5% |
| Kolliphor ® ELP | 2.5% |
| polysorbate 80 | 1% |
| poloxamer 407 | 1% |
| hypromellose | 0.1% |
| deionized $H_2O$ | 90.2% |

A solution of levcromakalim in ethanol (1 mL of 6 mg/mL stock) was combined with the EtOH-based solutions of glycerin, Kolliphor® ELP, polysorbate 80, poloxamer 407, and hypromellose aliquoted into a 5 mL vial. The solvent was removed via evaporation under a stream of nitrogen, and the vial was placed under high vacuum for 24 hours for further evaporation resulting in a thin film. The final volume was brought to 3 mL using deionized $H_2O$ such that the concentration of glycerin was about 5%, Kolliphor® ELP was about 2.5%, polysorbate 80 was about 1%, poloxamer 407 was about 1%, and hypromellose was about 0.1%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 1.27 mg/mL or 4.4 mM.

Example 2g

| Formula 2g | |
|---|---|
| Component | % Conc. |
| levcromakalim | 0.2% |
| Kolliphor ® RH 40 | 4% |
| glycerin | 5% |
| PVP | 1% |
| Premulen ™ TR-2 | 0.1% |
| PBS Stock Solution | 10% |
| deionized $H_2O$ | 79.7% |

A solution of levcromakalim in ethanol (1 mL of 6 mg/mL stock) was combined with the EtOH-based Kolliphor® RH 40, glycerin, PVP, and Premulen™ TR-2 aliquoted into a 5 mL vial. The solvent was removed via evaporation under a stream of nitrogen, and the vial was placed under high vacuum for 24 hours for further evaporation resulting in a thin film. 300 μL of PBS Stock Solution was then added, and the final volume was brought to 3 mL using deionized $H_2O$ such that the concentration of Kolliphor® RH 40 was about 4%, glycerin was about 5%, PVP was about 1%, and Premulen™ TR-2 was about 0.1%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 1.05 mg/mL or 3.7 mM.

Example 2h

| Formula 2h | |
|---|---|
| Component | % Conc. |
| levcromakalim | 0.2% |
| Kolliphor ® HS 15 | 5% |
| octoxynol-40 | 1% |
| polysorbate 80 | 1% |
| Premulen ™ TR-2 | 0.1% |
| poloxamer 407 | 1% |
| PBS Stock Solution | 10% |
| deionized $H_2O$ | 81.7% |

A solution of leveromakalim in ethanol (1 mL of 6 mg/mL stock) was combined with the EtOH-based solutions of Kolliphor® HS 15, octoxynol-40, polysorbate 80, Premulen™ TR-2, and poloxamer 407 aliquoted into a 5 mL vial. The solvent was removed via evaporation under a stream of nitrogen, and the vial was placed under high vacuum for 24 hours for further evaporation resulting in a thin film. 300 μL of PBS Stock Solution was then added, and the final volume was brought to 3 mL using deionized $H_2O$ such that the concentration of Kolliphor® HS 15 was about 4%, octoxynol-40 was about 1%, polysorbate 80 was about 1%, Premulen™ TR-2 was about 0.1%, and poloxamer 407 was about 1%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 1.26 mg/mL or 4.4 mM.

Example 2i

| Formula 2i | |
|---|---|
| Component | % Conc. |
| levcromakalim | 0.15% |
| glycerin | 1% |
| Kolliphor ® ELP | 2% |
| polysorbate 80 | 1% |
| poloxamer 407 | 0.1% |
| PVP | 1% |
| mannitol | 2% |
| Stock Phosphate Non-Saline Buffer solution | 10% |
| deionized $H_2O$ | 82.75% |

Ethanol (EtOH) based solutions of levcromakalim, glycerin, Kolliphor® ELP, polysorbate 80, poloxamer 407, and PVP were combined in a 50 mL round bottom flask, stirred, and heated (if necessary) until homogenous. The solvent was evaporated under a stream of nitrogen until a film was obtained, which was further dried under high vacuum for 24 hours. The film was reformulated by addition of the water-based solution of mannitol. To the mixture, 1 mL of the Stock Phosphate Non-Saline Buffer solution, and deionized $H_2O$ was added to bring the volume to 10 mL such that the concentration of levcromakalim was about 0.15%, glycerin was about 1%, Kolliphor®-ELP was about 2%, polysorbate 80 was about 1%, poloxamer 407 was about 0.1%, PVP was about 1%, and mannitol was about 2%. The solution was transferred to a septa vial and heated to 120° C. in an autoclave for 15 minutes. The solution was incubated overnight at room temperature and filtered through a sterile 0.22 μm filter into a sterile vial. Levcromakalim concentration measured using the standard curve method was about 1.23 mg/mL or 4.3 mM.

Example 2j

| Formula 2j | |
|---|---|
| Component | % Conc. |
| levcromakalim | 0.15% |
| glycerin | 4% |
| Kolliphor ® ELP | 2% |
| polysorbate 80 | 1% |
| poloxamer 407 | 0.1% |
| hypromellose | 0.1% |
| mannitol | 3.5% |
| BAK | 0.02% |
| Stock Phosphate Non-Saline Buffer solution | 10% |
| deionized $H_2O$ | 79.13% |

Ethanol (EtOH) based solutions of levcromakalim, glycerin, Kolliphor® ELP, polysorbate 80, poloxamer 407, and Hypromellose) were combined in a 50 mL round bottom flask, stirred, and heated (if necessary) until homogenous. The solvent was evaporated under a stream of nitrogen until a film was obtained, which was further dried under high vacuum for 24 hours. The film was reformulated by addition of the aqueous components. To the mixture, 1 mL of the Stock Phosphate Non-Saline Buffer solution, and deionized $H_2O$ were added to bring the volume to 10 mL such that the concentration of levcromakalim was about 0.15%, glycerin was about 4%, Kolliphor®-ELP was about 2%, polysorbate 80 was about 1%, poloxamer 407 was about 0.1%, hypromellose was about 0.1%, mannitol was about 3.5%, benzalkonium chloride was about 0.02%. The solution was transferred to a septa vial and heated to 120° C. in an autoclave for 15 minutes. The solution was incubated overnight at room temperature and filtered through a sterile 0.22 μm filter into a sterile vial. Levcromakalim concentration measured using the standard curve method was about 1.31 mg/mL or 4.6 mM.

Example 3—Ocular Formulations of Leveromakalim at the Concentration of >1.5 mg/mL or >5.2 mM

Example 3a

| Formula 3a | |
|---|---|
| Component | % Conc. |
| levcromakalim | 0.2% |
| Kolliphor ® ELP | 5% |
| polysorbate 80 | 2% |
| PVP | 2% |
| deionized $H_2O$ | 90.8% |

A solution of levcromakalim in ethanol (1 mL of 6 mg/mL stock), and EtOH-based solutions of Kolliphor® ELP, polysorbate 80, PVP were combined in a 5 mL vial. The solvent was removed via evaporation under a stream of nitrogen, and the vial was placed under high vacuum for 24 hours for further evaporation resulting in a thin film. The final volume was brought to 3 mL using deionized $H_2O$ such that the concentration of Kolliphor® ELP was about 5%, Polysorbate 80 was about 2%, and PVP was about 2%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 1.7 mg/mL or 5.8 mM.

Example 3b

| Formula 3b | |
|---|---|
| Component | % Conc. |
| levcromakalim | 0.2% |
| Kolliphor ® ELP | 5% |
| polysorbate 80 | 1% |
| poloxamer 407 | 1% |
| Stock Phosphate Non-Saline Buffer solution | 10% |
| deionized $H_2O$ | 82.8% |

A solution of levcromakalim in ethanol (1 mL of 6 mg/mL stock), and EtOH-based solutions of Kolliphor® ELP, polysorbate 80, and poloxamer 407 were combined in a 5 mL vial. The solvent was removed via evaporation under a stream of nitrogen, and vial was placed under high vacuum for 24 h for further evaporation resulting in a thin film. 300 μL of the Stock Phosphate Non-Saline Buffer solution was then added, and final volume was brought to 3 mL using deionized $H_2O$ such that the concentration of Kolliphor® ELP was about 5%, polysorbate 80 was about 1%, and poloxamer 407 was about 1%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 2.1 mg/mL or 7.3 mM.

Example 3c

| Formula 3c | |
|---|---|
| Component | % Conc. |
| levcromakalim | 0.2% |
| Kolliphor ® ELP | 4% |
| polysorbate 80 | 1% |
| PVP | 2% |
| poloxamer 407 | 0.1% |
| PBS Stock Solution | 10% |
| deionized $H_2O$ | 82.7% |

A solution of levcromakalim in ethanol (1 mL of 6 mg/mL stock) was combined with the EtOH-based solutions of Kolliphor® ELP, polysorbate 80, PVP, and poloxamer 407 aliquoted into a 5 mL vial. The solvent was removed via evaporation under a stream of nitrogen, and the vial was placed under high vacuum for 24 hours for further evaporation resulting in a thin film. 300 μL of PBS Stock Solution was then added, and final volume was brought to 3 mL using deionized $H_2O$ such that the concentration of Kolliphor® ELP was about 4%, polysorbate 80 was about 1%, PVP was about 2%, and poloxamer 407 was about 0.1%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 1.8 mg/mL or 6.4 mM.

Example 3d

| Formula 3d | |
|---|---|
| Component | % Conc. |
| levcromakalim | 0.15% |
| Kolliphor ® ELP | 4% |
| polysorbate 80 | 1% |
| PVP | 2% |
| poloxamer 407 | 0.1% |
| mannitol | 3.5% |
| Stock Phosphate Non-Saline Buffer solution | 10% |
| deionized $H_2O$ | 79.25% |

Ethanol (EtOH) based solutions of leveromakalim, Kolliphor® ELP, polysorbate 80, PVP, and poloxamer 407 were combined in a 50 mL round bottom flask, stirred, and heated (if necessary) until homogenous. The solvent was evaporated under a stream of nitrogen until a film was obtained, which was further dried under high vacuum for 24 hours. The film was reformulated by addition of the aqueous components. To the mixture, 1 mL of the Stock Phosphate Non-Saline Buffer solution, and deionized $H_2O$ were added to bring the volume to 10 mL such that the concentration of levcromakalim was about 0.15%, Kolliphor®-ELP was about 4%, polysorbate 80 was about 1%, PVP was about 2%, poloxamer 407 was about 0.1%, and mannitol was about 3.5%. The solution was transferred to a septa vial and heated to 120° C. in an autoclave for 15 minutes. The solution was incubated overnight at room temperature and filtered through a sterile 0.22 μm filter into a sterile vial. Levcromakalim concentration measured using the standard curve method was about 1.6 mg/mL or 5.5 mM.

Example 3e

Formula 3e

| Component | % Conc. |
|---|---|
| levcromakalim | 0.2% |
| glycerin | 4% |
| Kolliphor ® ELP | 2% |
| polysorbate 80 | 1% |
| poloxamer 407 | 0.1% |
| hypromellose | 0.1% |
| PBS Stock Solution | 10% |
| deionized $H_2O$ | 82.8% |

A solution of leveromakalim in ethanol (1 mL of 6 mg/mL stock) was added to a 3 mL vial. EtOH-based solutions of glycerin, Kolliphor® ELP, polysorbate 80, poloxamer 407, Hypromellose were aliquoted into the 3 mL vial, stirred, and heated (if necessary) until homogenous. The solvent was removed by evaporation under a stream of nitrogen and drying under high vacuum for 24 hours to provide a film. 300 μL of PBS Stock Solution and water were then added to dissolve or suspend the film with rapid stirring or sonication, which provided the formulation such that the concentration of glycerin was about 4%, Kolliphor® ELP was about 2%, polysorbate 80 was about 1%, poloxamer 407 was about 0.1%, and hypromellose was about 0.1%. Levcromakalim concentration measured using the standard curve method was about 1.9 mg/mL or 6.5 mM.

Formula 3f

| Component | % Conc. |
|---|---|
| levcromakalim | 0.15% |
| Kolliphor ® ELP | 4% |
| polysorbate 80 | 1% |
| PVP | 2% |
| poloxamer 407 | 0.1% |
| mannitol | 3.5% |
| BAK | 0.02% |
| Stock Phosphate Non-Saline Buffer solution | 10% |
| deionized $H_2O$ | 79.23% |

Ethanol (EtOH) based solutions of levcromakalim, Kolliphor® ELP, polysorbate 80, PVP, and poloxamer 407 were combined in a 50 mL round bottom flask, stirred, and heated (if necessary) until homogenous. The solvent was evaporated under a stream of nitrogen until a film was obtained, which was further dried under high vacuum for 24 hours. The film was reformulated by addition of the water-based solutions of mannitol, and BAK. To the mixture, 1 mL of the Stock Phosphate Non-Saline Buffer solution, and deionized $H_2O$ were added to bring the volume to 10 mL such that the concentration of levcromakalim was about 0.15%, Kolliphor®-ELP was about 4%, polysorbate 80 was about 1%, PVP was about 2%, poloxamer 407 was about 0.1%, mannitol was about 3.5%, and benzalkonium chloride (BAK) was about 0.02%. The solution was transferred to a septa vial and heated to 120° C. in an autoclave for 15 minutes. The solution was incubated overnight at room temperature and filtered through a sterile 0.22 μm filter into a sterile vial. Leveromakalim concentration measured using the standard curve method was about 1.5 mg/mL or 5.4 mM.

Example 3g

Formula 3g

| Component | % Conc. |
|---|---|
| levcromakalim | 0.15% |
| glycerin | 4% |
| Kolliphor ® ELP | 2% |
| polysorbate 80 | 1% |
| poloxamer 407 | 0.1% |
| hypromellose | 0.1% |
| mannitol | 3.5% |
| Stock Phosphate Non-Saline Buffer solution | 10% |
| deionized $H_2O$ | 79.15% |

Ethanol (EtOH) based solutions of levcromakalim, glycerin, Kolliphor® ELP, polysorbate 80, poloxamer 407, and hypromellose were combined in a 50 mL round bottom flask, stirred, and heated (if necessary) until homogenous. The solvent was evaporated under a stream of nitrogen until a film was obtained, which was further dried under high vacuum for 24 hours. The film was reformulated by addition of the water-based solution of mannitol. To the mixture, 1 mL of the Stock Phosphate Non-Saline Buffer solution, and deionized $H_2O$ were added to bring the volume to 10 mL such that the concentration of levcromakalim was about 0.15%, glycerin was about 4%, Kolliphor® ELP was about 2%, polysorbate 80 was about 1%, poloxamer 407 was about 0.1%, hypromellose was about 0.1%, and mannitol was about 3.5%. The solution was transferred to a septa vial and heated to 120° C. in an autoclave for 15 minutes. The solution was incubated overnight at room temperature and filtered through a sterile 0.22 μm filter into a sterile vial. Levcromakalim concentration measured using the standard curve method was about 1.6 mg/mL or 5.7 mM.

Example 3h

Formula 3h

| Component | % Conc. |
|---|---|
| levcromakalim | 0.2% |
| Kolliphor ® ELP | 4% |
| polysorbate 80 | 1% |
| PVP | 2% |
| poloxamer 407 | 0.1% |
| Stock Phosphate Non-Saline Buffer solution | 10% |
| mannitol | 3.5% |
| BAK | 0.02% |
| deionized $H_2O$ | 79.18% |

A solution of leveromakalim in ethanol (1 mL of 6 mg/mL stock), and EtOH-based solutions of Kolliphor® ELP, polysorbate 80, PVP, and poloxamer 407 were combined in a 5 mL vial. The solvent was removed via evaporation under a stream of nitrogen, and the vial was placed under high vacuum for 24 hours for further evaporation resulting in a thin film. The water-based solutions of mannitol, BAK, and 300 μL of the Stock Phosphate Non-Saline Buffer solution were then added, and the final volume was brought to 3 mL using deionized $H_2O$ such that the concentration of Kolliphor® ELP was about 4%, polysorbate 80 was about 1%, PVP was about 2%, poloxamer 407 was about 1%, mannitol was about 3.5%, and benzalkonium chloride was about 0.02%. The mixture was stirred in a heating block at 80° C. for 20 minutes. Then, the mixture was incubated at room temperature overnight and filtered through a 0.45 μm filter to provide a saturated solution. Levcromakalim concentration measured using the standard curve method was about 1.7 mg/mL or 5.9 mM.

Example 4 Additional Formulations

Formula 4a

| Component | Conc. % |
|---|---|
| levcromakalim | 0.2% |
| hydrogenated castor oil-40 (HCO-40) | 1.0% |
| octoxynol-40 | 0.05% |
| sodium chloride | 0.1% |
| PVP-K90 | 0.6% |
| disodium EDTA | 0.05% |
| BAK | 0.003% |
| PBS | 0.4% |
| deionized $H_2O$ + phosphate buffer | 97.5% |

A solution of leveromakalim in ethanol (1 mL of 6 mg/mL stock), and EtOH-based solutions of hydrogenated castor oil-40, octoxynol-40, PVP, and disodium-EDTA are combined in a round bottom flask and mixed to homogenize. The solvent is removed by evaporation and further dried under high vacuum to obtain a thin film. The film is rehydrated by adding water-based solutions of sodium chloride, BAK, PBS, and about 2.5 mL deionized water and stirred overnight. The pH of the formulation is adjusted to neutral with additional phosphate buffer and the final volume was brought to 3 mL using deionized $H_2O$. The formulation was then filtered through 0.2 μm nylon filter. Levcromakalim concentration is measured using the standard curve method.

Example-4b

Formula-4b

| Component | Conc. % |
|---|---|
| Levcromakalim | 0.15% |
| hydrogenated castor oil-40 | 1.0% |
| octoxynol-40 (HCO-40) | 0.05% |
| sodium chloride | 0.1% |
| PVP-K90 | 0.6% |
| disodium EDTA | 0.05% |
| BAK | 0.003% |
| PBS | 0.4% |
| deionized $H_2O$ + phosphate buffer | 97.6% |

Ethanol-based solution of levcromakalim, and EtOH-based solutions of hydrogenated castor oil-40, octoxynol-40, PVP, and disodium-EDTA are combined in a round bottom flask and mixed to homogenize. The solvent is removed by evaporation and further dried under high vacuum to obtain a thin film. The film is rehydrated by adding water-based solutions of sodium chloride, BAK, PBS, and about 2.5 mL deionized water and stirred overnight. pH of the formulation is adjusted to neutral with additional phosphate buffer and the final volume was brought to 3 mL using deionized $H_2O$. The formulation was then filtered through 0.2 μm nylon filter. Leveromakalim concentration is measured using the standard curve method.

Example 4c

Formula 4c

| Component | Conc. % |
|---|---|
| Levcromakalim | 0.2% |
| hydrogenated castor oil-40 (HCO-40) | 4.0% |
| octoxynol-40 | 0.01% |
| deionized $H_2O$ + phosphate buffer | 95.5% |

A solution of levcromakalim in ethanol (1 mL of 6 mg/mL stock), and EtOH-based solutions of hydrogenated castor oil-40 and octoxynol-40 are combined in a round bottom flask and mixed to homogenize. The solvent is removed by evaporation and further dried under high vacuum to obtain a thin film. The film is rehydrated with about 2.5 deionized water and stirred overnight. pH of the formulation is adjusted to neutral with phosphate buffer and the final volume was brought to 3 mL using deionized $H_2O$. The formulation was then filtered through 0.2 μm nylon filter. Levcromakalim concentration is measured using the standard curve method.

Example 4d

Formula 4d

| Component | Conc. % |
|---|---|
| levcromakalim | 0.2% |
| hydrogenated castor oil-60 (HCO-60) | 1.0% |
| octoxynol-40 | 0.05% |
| sodium chloride | 0.1% |
| PVP-K90 | 0.6% |
| disodium EDTA | 0.05% |
| BAK | 0.003% |
| PBS | 0.4% |
| deionized $H_2O$ + phosphate buffer | 97.5% |

A solution of leveromakalim in ethanol (1 mL of 6 mg/mL stock), and EtOH-based solutions of hydrogenated castor oil-60, octoxynol-40, PVP, and disodium-EDTA are combined in a round bottom flask and mixed to homogenize. The solvent is removed by evaporation and further dried under high vacuum to obtain a thin film. The film is rehydrated by adding water-based solutions of sodium chloride, BAK, PBS, and about 2.5 mL deionized water and stirred overnight. pH of the formulation is adjusted to neutral with additional phosphate buffer and the final volume was brought to 3 mL using deionized $H_2O$. The formulation was then filtered through 0.2 μm nylon filter. Levcromakalim concentration is measured using the standard curve method.

Example 4e

| Formula 4e | |
|---|---|
| Component | Conc. % |
| levcromakalim | 0.2% |
| hydrogenated castor oil-80 (HCO-80) | 1.0% |
| octoxynol-40 | 0.05% |
| sodium chloride | 0.1% |
| PVP-K90 | 0.6% |
| disodium EDTA | 0.05% |
| BAK | 0.003% |
| PBS | 0.4% |
| deionized $H_2O$ + phosphate buffer | 97.5% |

A solution of levcromakalim in ethanol (1 mL of 6 mg/mL stock), and EtOH-based solutions of hydrogenated castor oil-80, octoxynol-40, PVP, and disodium-EDTA are combined in a round bottom flask and mixed to homogenize. The solvent is removed by evaporation and further dried under high vacuum to obtain a thin film. The film is rehydrated by adding water-based solutions of sodium chloride, BAK, PBS, and about 2.5 mL deionized water and stirred overnight. pH of the formulation is adjusted to neutral with additional phosphate buffer and the final volume was brought to 3 mL using deionized $H_2O$. The formulation was then filtered through 0.2 μm nylon filter. Levcromakalim concentration is measured using the standard curve method.

Example 4f

| Formula 4f | |
|---|---|
| Component | Conc. % |
| levcromakalim | 0.2% |
| hydrogenated castor oil-100 (HCO-100) | 1.0% |
| octoxynol-40 | 0.05% |
| sodium chloride | 0.1% |
| PVP-K90 | 0.6% |
| disodium EDTA | 0.05% |
| BAK | 0.003% |
| PBS | 0.4% |
| deionized $H_2O$ + phosphate buffer | 97.5% |

A solution of levcromakalim in ethanol (1 mL of 6 mg/mL stock), and EtOH-based solutions of hydrogenated castor oil-100, octoxynol-40, PVP, and disodium-EDTA are combined in a round bottom flask and mixed to homogenize. The solvent is removed by evaporation and further dried under high vacuum to obtain a thin film. The film is rehydrated by adding water-based solutions of sodium chloride, BAK, PBS, and about 2.5 mL deionized water and stirred overnight. pH of the formulation is adjusted to neutral with additional phosphate buffer and the final volume was brought to 3 mL using deionized $H_2O$. The formulation was then filtered through 0.2 μm nylon filter. Levcromakalim concentration is measured using the standard curve method.

VIII. In Vivo Evaluation

Example 5 In Vivo Assessments of Ocular Formulations 3f and 3d in Mice

| Formulation 3f | |
|---|---|
| Component | % Conc. |
| Levcromakalim | 0.15% |
| Kolliphor ® ELP | 4% |
| polysorbate 80 | 1% |
| PVP | 2% |
| poloxamer 407 | 0.1% |
| Mannitol | 3.5% |
| BAK | 0.02% |
| Stock Phosphate Non-Saline Buffer solution | 10% |
| deionized $H_2O$ | 79.23% |

| Formulation 3d | |
|---|---|
| Component | % Conc. |
| Levcromakalim | 0.15% |
| Kolliphor ® ELP | 4% |
| polysorbate 80 | 1% |
| PVP | 2% |
| poloxamer 407 | 0.1% |
| Mannitol | 3.5% |
| Stock Phosphate Non-Saline Buffer solution | 10% |
| deionized $H_2O$ | 79.25% |

Levcromakalim (*DMSO* + Cremophor) Formulation

Leveromakalim (>98%, molecular weight 286.33 g/mol; molecular weight of disodium salt −332.3 g/mol) was purchased from MilliporeSigma (Cat #$C_{1055}$). A 100 mM stock solution was prepared by mixing 28.63 mg of levcromakalim into 1 mL of DMSO (MilliporeSigma, Cat. #D2650) for a concentration of 28.63 mg/mL. The stock solution was diluted 20-fold with 10% Cremophor EL (MilliporeSigma, Cat #238470) in sterile PBS (Corning Cat #21-040-CV), to make a 5 mM working solution (1.43 mg/l ml in 5% DMSO/10% Cremophor EL/85% PBS)

Ocular formulation of levcromakalim with Benzalkonium chloride (BAK) formulations 3f (Osmolarity=245 Osm/L) and its analogous formulation without BAK 3d (Osmolarity=280 Osm/L) were administered in efficacy experiments to determine their ability to lower intraocular pressure (IOP) in a group of normotensive mice. Levcromakalim formulation (0.5 mM) made by serial dilution of levcromakalim (DMSO+Cremophor) formulation was used as a positive control and vehicle of each formulation was used as a negative control.

Dosing: Mice (n=5 per group; 3 females and 2 males) received once daily 5 L drops of 0.5 mM (0.015% levcromakalim) formulated in 1 of the 2 formulations (Formulation 3f and 3d) in one eye in the morning. The contralateral eye was dosed with the formulation vehicle alone (without the inclusion of levcromakalim) as a control. Positive control mice (n=5; 2 females and 3 males) were administered levcromakalim (0.5 mM) formulation made by serial dilution of levcromakalim (DMSO+Cremophor) formulation, in one eye with the contralateral receiving serially diluted analogous DMSO+Cremophor in sterile PBS alone as a vehicle control.

Timing: Baseline IOPs were measured for 3 days prior to dosing using the iCare TonoPen rebound tonometer. Mice were dosed with the above formulations for 5 days to determine efficacy. Following a 3-day washout period, mice (n=5 per group) were given further doses of 0.005 mM, 0.05 mM, and 5.0 mM for 5 days per period with the contralateral eye receiving matched vehicle control. These animals were compared to positive control mice that were administered levcromakalim at 0.005 mM, 0.05 mM, and 5.0 mM formulated by serial dilution of levcromakalim (DMSO+Cremophor) formulation in one eye with the contralateral receiving serially diluted analogous DMSO+Cremophor in sterile PBS alone as a vehicle control. IOPs were measured and analyzed daily at 1 h and 23 h post-dosing. The comparison of the IOP lowering is summarized in the table as described herein.

Analysis: IOPs were measured daily at 1 h and 23 h post-dosing at approximately 10:30 am. Data depicted shows the average IOPs from Days 3 and 4 of dosing (per dosing period). FIG. 1 depicts IOP lowering data of formulations 3f and 3d with vehicle as a negative control and DMSO+Cremophor formulation as a positive control. FIG. 3 depicts comparison of IOP lowering by different concentrations of levcromakalim formulated in formulations 3f, 3d, and levcromakalim (>98% levcromakalim) formulated in DMSO and Cremophor EL.

Statistics: Daily IOP was calculated by taking the average of the 1- and 23-h time points (i.e., calculating the mean±SD). Baseline IOP was calculated for each eye by calculating the mean±SD daily IOP of the three daily pretreatment measurements. Intraocular pressure during the treatment period was determined for each eye by calculating the mean±SD daily IOP of day 3 and 4 treatments.

TABLE 2

IOP Lowering by Ocular Formulations 3f and 3d in Mice

| | % IOP decrease vs baseline | | | |
|---|---|---|---|---|
| Formulation | 0.005 mM | 0.05 mM | 0.5 mM | 5 mM |
| Formulation 3f | 17.69 ± 2.12 | 20.46 ± 3.06 | 23.94 ± 2.61% | 25.55 ± 0.76 |
| Formulation 3d | 19.32 ± 7.11 | 26.90 ± 3.65 | 31.21 ± 3.16% | 29.55 ± 2.11 |
| Levcromakalim (DMSO + Cremophor) formulation | 19.99 ± 8.43 | 21.45 ± 1.48 | 25.55 ± 2.56% | 23.60 ± 2.94 |

Example 6 In Vivo Assessments of Ocular Formulations 2j and 3g in Mice

Formulation 2j

| Component | % Conc. |
|---|---|
| Levcromakalim | 0.15% |
| Glycerin | 4% |
| Kolliphor ® ELP | 2% |
| polysorbate 80 | 1% |
| poloxamer 407 | 0.1% |
| Hypromellose | 0.1% |
| Mannitol | 3.5% |
| BAK | 0.02% |
| Stock Phosphate Non-Saline Buffer solution | 10% |
| deionized $H_2O$ | 79.13% |

-continued

Formulation 3g

| Component | % Conc. |
|---|---|
| Levcromakalim | 0.15% |
| Glycerin | 4% |
| Kolliphor ® ELP | 2% |
| polysorbate 80 | 1% |
| poloxamer 407 | 0.1% |
| Hypromellose | 0.1% |
| Mannitol | 3.5% |
| Stock Phosphate Non-Saline Buffer solution | 10% |
| deionized $H_2O$ | 79.15% |

Ocular formulation of levcromakalim with Benzalkonium chloride (BAK), formulation 2j (Osmolarity=723 Osm/L) and its analogous formulation without BAK, formulation 3g (Osmolarity=762 Osm/L) were administered in efficacy experiments to determine their ability to lower intraocular pressure (IOP) in a group of normotensive mice. Levcromakalim formulation in DMSO and Cremophor EL was used as a positive control and vehicle of each formulation was used as a negative control.

Dosing: Mice (n=5 per group; 3 females and 2 males) received once daily 5 L drops of 0.5 mM (0.015% levcromakalim) formulated in 1 of the 2 formulations (Formulation 2j and 3g) in one eye in the morning. The contralateral eye was dosed with the formulation vehicle alone (without the inclusion of levcromakalim) as a control. Positive control mice (n=5; 2 females and 3 males) were administered levcromakalim (0.5 mM) formulation made by serial dilution of levcromakalim (DMSO+Cremophor) formulation, in one eye with the contralateral receiving serially diluted analogous DMSO+Cremophor in sterile PBS alone as a vehicle control Timing: Baseline IOPs were measured for 3 days prior to dosing using the iCare TonoPen rebound tonometer. Mice were dosed with the above formulations for 5 days to determine efficacy. These animals were compared to positive control mice that were administered levcromakalim (0.5 mM) formulated by serial dilution of levcromakalim (DMSO+Cremophor) formulation in one eye with the contralateral receiving serially diluted analogous DMSO+Cremophor in sterile PBS alone as a vehicle control. IOPs were measured and analyzed daily at 1 h and 23 h post-dosing. The comparison of the IOP lowering is summarized in the table as described herein.

Analysis: IOPs were measured daily at 1 h and 23 h post-dosing at approximately 10:30 am. Data depicted shows the average IOPs from Days 3 and 4 of dosing (per dosing period). FIG. 2 depicts IOP lowering data of formulations 2j and 3g with vehicle as a negative control and DMSO+Cremophor formulation as a positive control.

Statistics: Daily IOP was calculated by taking the average of the 1- and 23-h time points (i.e., calculating the mean±SD). Baseline IOP was calculated for each eye by calculating the mean±SD daily IOP of the three daily pretreatment measurements. Intraocular pressure during the treatment period was determined for each eye by calculating the mean SD daily IOP of day 3 and 4 treatments.

TABLE 3

IOP Lowering by Ocular Formulations 2j and 3g in Mice

| Formulation | % IOP decrease vs baseline |
|---|---|
| Formulation 2j | 22.13 ± 2.06% |
| Formulation 3g | 25.19 ± 3.12% |
| Levcromakalim (DMSO + Cremophor) formulation | 25.55 ± 2.56% |

Example 7 Aqueous Humor Dynamics (AHD) in C57BL/6J Mice Following Treatment with Formulation 3d in Mice Formulation 3d

| Component | % Conc. |
|---|---|
| Levcromakalim | 0.15% |
| Kolliphor ® ELP | 4% |
| polysorbate 80 | 1% |
| PVP | 2% |
| poloxamer 407 | 0.1% |
| Mannitol | 3.5% |
| Stock Phosphate Non-Saline Buffer solution | 10% |
| deionized $H_2O$ | 79.25% |

Study Objective: The objective of this study was to determine the effect of topical ophthalmic administration of formulation 3d on aqueous humor dynamics in a normotensive mammal (mouse).

Study design: C57BL/6J mice were used in this study. This data can be compared to the studies published in Roy Chowdhury et al, 2015, PLOS ONE; Roy Chowdhury et al, 2017, IOVS).

Method: Wild-type C57BL/6J mice (n=7) were obtained from Jackson Laboratories (Bar Harbor, ME, USA). Following one day of baseline IOP measurements, a 5-μL bolus of formulation 3d (0.5 mM) was applied topically to both eyes of each animal (n=4) once daily for 3 consecutive days.

In a separate cohort (n=3), a 5-μL bolus of vehicle was applied topically to both eyes once daily for 3 consecutive days. Following day 3 treatment, IOP was measured, and animals were anesthetized by intraperitoneal injection of ketamine (100 mg/kg), xylazine (10 mg/kg) and acepromazine (1 mg/kg). AHD (aqueous humor dynamics) was assessed by constant flow infusion as previously described. (Millar et al, 2011, IOVS; Roy Chowdhury et al 2017, IOVS). All data were recorded and analyzed with LabScribe4 software (World Precision Instruments). Outflow facility and episcleral venous pressure were measured, and uveoscleral outflow and aqueous humor flow rate were calculated. Drug tolerability was assessed by visual observation daily.

Results: Mice treated with 0.5 mM formulation 3d showed an IOP decrease from 16.46±0.5 mmHg to 12.25±0.89 mmHg. In contrast, mice treated with vehicle showed no change from baseline IOP (16.33±0.30 mmHg to 16.39±0.49 mmHg). Mice treated with formulation 3d showed a decrease in episcleral venous pressure (4.05±0.42 mmHg) compared to vehicle-treated controls (9.81±1.12 mmHg). Reduction of episcleral venous pressure was statistically significant (p=0.0002). No significant change was found in outflow facility, uveoscleral outflow or aqueous humor flow rate. Daily clinical assessments found no differences between drug-treated and vehicle-treated control mice.

TABLE 4

Aqueous Humor Dynamics (AHD) Parameters Following Treatment with Formulation 3d and Vehicle in Mice.

| | Formulation 3d treated cohort (n = 4) | | Vehicle treated cohort (n = 3) | | p- |
|---|---|---|---|---|---|
| | Average | Stdev | Average | Stdev | value |
| IOP Baseline (mmHg) | 16.5 | 0.50 | 16.3 | 0.30 | 0.60 |
| IOP Treatment (mmHg) | 12.3 | 0.89 | 16.4 | 0.49 | <0.001 |
| Outflow Facility (μl/min/mmHg) | 0.06 | 0.01 | 0.04 | 0.01 | 0.11 |
| Uveoscleral outflow (μl/min) | 0.05 | 0.03 | 0.06 | 0.02 | 0.57 |
| Aqueous Flow Rate (μl/min) | 0.51 | 0.15 | 0.31 | 0.15 | 0.15 |
| Episcleral Venous Pressure(mmHg) | 4.05 | 0.42 | 9.81 | 1.12 | <0.001 |

The data in Table 4 shows that formulation 3d lowers IOP by reducing episcleral venous pressure (EVP) in normotensive C57/BL6J mice. No significant change was found in outflow facility, uveoscleral outflow or aqueous humor flow rate.

Example 8 Exploratory Study to Assess Safety and Tolerability of Formulation 3d in Humans Exploratory study of levcromakalim formulation 3d were conducted in Mexico under the direction of a board-certified ophthalmologist with practices in Mexico City in accordance with GCP and ICH guidelines. Initially, a randomized, masked, study was conducted to examine the ocular and systemic safety and tolerability of two concentrations of topical ophthalmic delivery of formulation 3d (0.5 mM and 5 mM), as a topical ophthalmic intraocular pressure (IOP) lowering agent. Of the 14 subjects that received formulation 3d, two patients experienced AEs. Neither AL was considered serious, and no patients discontinued the study due to an AE. The onset of IOP lowering was demonstrated quickly, within 4 hours following the first topical administration of formulation 3d. Both concentrations of formulation 3d were well tolerated and demonstrated an IOP lowering effect throughout the 14-day treatment period.

Study Objective: The primary objective of this study was to evaluate the ocular and systemic safety and tolerability of two masked concentrations of formulation 3d administered once daily (QD) in both eyes (OU) for 14 days in 14 healthy humans. Another objective of this study was to evaluate the IOP lowering ability of formulation 3d in humans.

Study Design: Humans without significant comorbidities or significant ocular pathology were screened for this study. The first 3 study subjects enrolled had visual impairment, and formulation 3d QAM OU (0.5 or 5 mM) was administered to these subjects for 7 days. Following confirmation of acceptable safety and tolerability, 14 subjects were enrolled and administered formulation 3d (0.5 or 5 mM) for 14 days.

Inclusion Criteria for First 3 Enrollments:

1) 20 years of age or older
2) Have visual impairment such that BCVA is 20/200 or worse, ocular, and/or cortical (CNS) pathology i.e., amblyopia, retinal or cornea pathology and or advanced cataracts in at least one eye. Only the visually impaired eye would be treated. If both eyes qualify, both can be treated. The visual impairment should not be due to severe corneal pathology that could impact accurate IOP measurements.

Inclusion Criteria for Volunteers: 14 Volunteers were Selected Post Screen 1) 20 years of age or older
2) Have an IOP ≥17 mmHg at morning screening visit

TABLE 5

Human Subject Disposition

| | Formulation 3d 0.5 mM | Formulation 3d 5 mM | Patients |
|---|---|---|---|
| Screened, n | — | — | 17 |
| Screened but not | — | — | 3 |
| Enrolled and Treated, n | 8 | 6 | 14 |
| Completed visit, n (%) | | | |
| Day 1 | 8 (100) | 6 (100.0) | 14 (100) |
| Day 4 | 7 (88) | 6 (100.0) | 13 (93) |
| Day 7 | 7 (88) | 6 (100.0) | 13 (93) |
| Day 14 | 7 (88) | 6 (100.0) | 13 (93) |
| Withdrawn Early or Lost to Follow-up, n (%) | 1 (13) | 0 (0) | 1 (7) |

As indicated in Table 5, the first 3 study subjects enrolled had visual impairment such that best corrected visual acuity (BCVA) is 20/200 or worse in at least one eye (defined in inclusion/exclusion). Following confirmation of safety and tolerability following study completion for the first 3 enrolled subjects, 14 volunteers were enrolled, randomized, and masked to receive one of two concentrations of formulation 3d (0.5 mM or 5 mM).

Method: Formulation 3d was provided in 0.5 mM and 5 mM concentrations, as a low and a high concentration (all treatment groups were provided masked bottles in bottles labeled A or B. Bottle A contained 0.5 mM formulation 3d and bottle B contained 5 mM formulation 3d.

Formulation 3d was administered once daily at 08:00 H, ±90 minutes QAM for 14 days (+2 days) in both eyes (OU). Safety and tolerability were observed through the collection of adverse events (AE). IOP was determined by Goldmann applanation tonometry (GAT) and iCare rebound tonometry. Clinical assessments included vital signs (blood pressure/BP, and heart rate/HR), IOP, BCVA (using early treatment of diabetic retinopathy study/ETDRS charts), slit lamp biomicroscopy and ophthalmoscopy, review of concomitant medications, and review of AEs. As the primary objective of this study was to evaluate the ocular and systemic safety and tolerability of two concentrations of formulation 3d, the exploratory endpoints included AEs, BCVA, slit lamp, and dilated ophthalmoscopy.

Safety: Two AEs were documented during the study, with one AE occurring in a visually impaired patient and the other AE reported in a generally healthy study participant. No subjects discontinued the study due to an AE. The systemic hypotensive AE in Subject 1, a participant in the 5 mM treatment group is a finding that correlates with earlier published findings when the active is given orally (Hamilton T C, Beerahee A, Moen J S, et al. Levcromakalim. Cardiovasc Drug Rev. 1993; 11(2)199-222).

There were no significant or adverse safety signals from the ophthalmic assessments or vital signs apart from the two reported AEs. In both treatment groups there were a few incidences of transient mild hyperemia on slit lamp assessment, that generally dissipated during the day and were deemed not clinically significant. In most instances the investigator attributed hyperemia to the use of topical anesthetic used during the study assessments.

Formulation 3d was shown to have an acceptable safe and tolerable profile with daily ophthalmic administration. There were only 2 AEs and the hypotensive event in Subject 1 correlates with published findings with the active when given orally (Hamilton 1993). There were no other adverse safety findings observed in this study.

Efficacy: Table 6 shows the IOP lowering efficacy of formulation 3d. Mean baseline IOP was 19.3 mmHg across all patients and 19.4 in the 5 mM treatment group and 19.2 in the 0.5 mM treatment group.

In the 5 mM, higher concentration treatment group, maximal IOP lowering was observed via Goldmann applanation tonometry (GAT) at the Day 7 visit with a −5.7 mmHg decrease (a decrease of 29% from baseline) at the pre-dose (AM) and 8-hour post-dose (late afternoon) timepoints. By iCare rebound tonometry, a maximal IOP decrease of −5.64 mmHg (a decrease of 29% from baseline) was identified at the Day 7 4-hour post-dose (mid-day) timepoint. In the 0.5 mM, lower concentration treatment group, maximal IOP lowering was observed via Goldmann applanation tonometry (GAT) at the Day 1 visit with a −5.67 mmHg decrease (a decrease of 29% from baseline) at the 8-hour post-dose (late afternoon) timepoint. By iCare rebound tonometry, a maximal IOP decrease of −5.39 mmHg (a decrease of 27% from baseline) was identified at the Day 14 4-hour post-dose (mid-day) timepoint. Onset of IOP lowering is demonstrated quickly, within 4 hours from the first dose of study drug administration on Day 1. Both treatment groups (5 mM and 0.5 mM) demonstrated IOP lowering efficacy.

TABLE 6

Intraocular Pressure (mmHg), Change from Baseline in the Study Eye in Humans (All Healthy Volunteers)

| | IOP | | Day 1 (n = 5) | | Day 7 (n = 5) | | | Day 14 (n = 5) | | |
|---|---|---|---|---|---|---|---|---|---|---|
| | Method | Baseline | 4 hr | 8 hr | 23 hr | 4 hr | 8 hr | 23 hr | 4 hr | 8 hr |
| 5 mM | iCare | 19.4 | −2.86 (−14%) | −3.99 (−20%) | −5.47 (−28%) | −5.64 (−29%) | −5.14 (−26%) | −2.91 (−14%) | −4.79 (−25%) | −4.73 (−24%) |
| | Goldmann | 19.4 | −2.90 (−14%) | −4.00 (−21%) | −5.70 (−29%) | −5.40 (−28%) | −5.70 (−29%) | −3.60 (−18%) | −5.30 (−27%) | −5.50 (−28%) |
| 0.5 mM | iCare | 19.3 | −3.84 (−19%) | −4.65 (−23%) | −4.48 (−22%) | −5.06 (−24%) | −5.02 (−24%) | −4.48 (−22%) | −5.39 (−27%) | −5.03 (−25%) |

TABLE 6-continued

| Intraocular Pressure (mmHg), Change from Baseline in the Study Eye in Humans (All Healthy Volunteers) | | | | | | | | | |
|---|---|---|---|---|---|---|---|---|---|
| IOP | | Day 1 (n = 5) | | Day 7 (n = 5) | | | Day 14 (n = 5) | | |
| Method | Baseline | 4 hr | 8 hr | 23 hr | 4 hr | 8 hr | 23 hr | 4 hr | 8 hr |
| Goldmann | 19.1 | −3.84 (−14%) | −5.67 (−21%) | −4.48 (−29%) | −5.06 (−28%) | −5.02 (−29%) | −4.48 (−18%) | −5.39 (−29%) | −5.03 (−27%) |

Hr: hour;
IOP: intraocular pressure;
mM: millimoles;
mmHg: millimeters Mercury

Of the 14 humans who received formulation 3d, two patients experienced AEs. Neither AE was considered serious, and no patients discontinued the study due to an AE. In both treatment groups there were a few incidences of transient mild hyperemia on slit lamp assessment, that generally dissipated by the next timepoint and were deemed not clinically significant. In most instances the investigator attributed hyperemia to the use of topical anesthetic used during the study assessments. Onset of IOP lowering is demonstrated quickly, within 4 hours following the first topical administration of study drug. Both concentrations (5 mM and 0.5 mM) have an IOP lowering effect throughout the 14-day treatment period.

Example 9 Masked Clinical Study to Assess Safety, Tolerability, and Ocular Hypotensive Efficacy of Formulation 3d in Humans A single-center, randomized, masked, vehicle-controlled study was conducted in human subjects to examine the ocular and systemic safety and tolerability of two concentrations of formulation 3d (0.5 mM and 2.5 mM) QAM for 7 days followed by BID for 7 days of dosing in 21 Humans who did not have any significant comorbidities or significant ocular pathology. No ocular or systemic AEs occurred in any of the 21 patients. Both the 0.5 mM and 2.5 mM formulation 3d treatment groups demonstrated IOP lowering efficacy in Human subjects.

Study Objective: The primary objective of this study was to evaluate the ocular and systemic safety and tolerability of two masked concentrations of formulation 3d administered once daily (QD) in both eyes (OU) for 7 days followed by dosing twice daily (BID) OU for 7 days. Another objective of this study was to evaluate the IOP lowering ability of formulation 3d.

Study Design: Subjects who didn't have any significant comorbidities or significant ocular pathology were screened on day 0, followed by visits on Day 1 (initiation of dosing), Day 7, and Day14 (end of study treatment).

Inclusion Criteria: Subjects were screen and 21 subjects who met the following criteria were selected.

1) 20 years of age or older
2) Have an IOP ≥17 mmHg at morning screening visit

TABLE 7

| Subject Disposition | | | | |
|---|---|---|---|---|
| | Formulation 3d (0.5 mM) | Formulation 3d (2.5 mM) | Vehicle | Patients |
| Screened, n | 7 | 7 | 7 | 27 |
| Screened but not | — | — | — | 6 |
| Enrolled and Treated, n | 7 | 7 | 7 | 21 |

TABLE 7-continued

| Subject Disposition | | | | |
|---|---|---|---|---|
| | Formulation 3d (0.5 mM) | Formulation 3d (2.5 mM) | Vehicle | Patients |
| Completed visit, n (%) | | | | |
| Day 1 | 7 | 7 | 7 | 21 (100) |
| Day 4 | 7 | 7 | 7 | 21 (100) |
| Day 7 | 7 | 7 | 7 | 21 (100) |
| Day 14 | 7 | 7 | 7 | 21 (100) |
| Withdrawn Early or Lost to Follow-up, n (%) | 0 | 0 | 0 | 0 (0) |

As indicated in Table 7, 21 enrolled subjects were randomized to either formulation 3d or vehicle. Formulation 3d (0.5 mM and 2.5 mM masked concentrations) or vehicle QAM OU were administered according to randomization for 7 days followed by BID OU dosing for another 7 days.

Method: Formulation 3d was provided to the human subjects in 0.5 mM and 2.5 mM concentrations, a low and a high concentration (all treatment groups were provided masked bottles in bottles labeled A, B, or C), supplied in non-preserved dropper bottles to be administered once daily at 08:00 H, ±90 minutes QAM OU for 7 days (+2 days) followed by BID administration for another 7 days (+2 days). A bottle of study drug was dispensed at visit 2 (day 1) and visit 3 (day 7). Patients were administered the same assigned treatment (A, B, or C) throughout the study. Safety and tolerability were observed through the collection of data which include adverse events (AEs), vital signs, and ophthalmic exams including best corrected visual acuity (BCVA), slit lamp, and ophthalmoscopy. At Screening and on days 1, 7 and 14, subjects' IOP were measured (pre-treatment on Day 1), Noon, and 4 PM by Goldmann applanation tonometry (GAT) and iCare rebound tonometry.

Clinical assessments included vital signs (blood pressure/BP, and heart rate/HR), IOP, BCVA (using early treatment of diabetic retinopathy study/ETDRS charts), slit lamp biomicroscopy and ophthalmoscopy, review of concomitant medications, and review of AEs. As the primary objective of this study was to evaluate the ocular and systemic safety and tolerability of two concentrations and two dosing regimens of formulation 3d, the exploratory endpoints included AEs, BCVA, slit lamp, and dilated ophthalmoscopy.

Safety: No significant ocular or systemic AEs such as hyperemia (eye redness), instillation pain, burning or stinging, corneal surface adverse events, or systemic adverse events were observed in the human subjects. Mild transient hyperemia following the morning dosing during the study visits was observed in 4 of 7 subjects in the 2.5 mM cohort only. This typically resolved within 20 minutes and always by the noon timepoint assessment. No changes on slit lamp exam were observed in the 0.5 mM formulation 3d or vehicle cohorts.

Efficacy: Table 8, Table 9, FIG. 5, FIG. 6, FIG. 7, and FIG. 8 show the IOP lowering efficacy of formulation 3d. Mean baseline IOP (GAT) was 17.0 mmHg across all subjects; 17.0 mmHg in the 2.5 mM formulation 3d treatment group, 16.7 mmHg in the lower concentration, 0.5 mM, formulation 3d treatment group, and 17.2 mmHg in the vehicle comparator treatment group.

At Day 7 (following QD dosing period) mean diurnal IOP lowering as measured by GAT was −2.1 mmHg (−12%), −2.1 mmHg (−13%), and −1.6 mmHg (−9%) in the 2.5 mM formulation 3d, 0.5 mM formulation 3d, and vehicle treatment groups, respectively, compared to baseline (FIG. 5). At Day 14 (following BID dosing period) mean diurnal IOP lowering was −2.6 mmHg (−15%), −3.5 mmHg (−21%), and −1.5 mmHg (−9%), in the 2.5 mM formulation 3d, 0.5 mM formulation 3d, and vehicle treatment groups, respectively, compared to baseline (FIG. 5 and FIG. 7).

The mean diurnal IOP lowering (GAT) for 0.5 mM formulation 3d group was significantly lower than the vehicle control group (p=0.003). Both formulation 3d treatment groups (2.5 mM and 0.5 mM) demonstrated IOP lowering efficacy (GAT and iCare). IOP in the 2.5 mM treatment group was significantly lower at the 4 PM timepoint on Day 7 (QAM dosing regimen) and at 4 PM on Day 14 (BID dosing regimen) compared to vehicle control. IOP in the 0.5 mM treatment group was significantly at noon and at 4 PM on Day 14 (BID dosing regimen) compared to vehicle control (Table 8, FIG. 6, and FIG. 8).

TABLE 8

Mean IOP Lowering (GAT) from Baseline (mmHg) of Formulation 3d (2.5 and 0.5 mM) and Vehicle Control (On days 7 and 14 and at each timepoint) in Humans

| Formulation | Day 7 (QAM Dosing) | | | Day 14 (BID Dosing) | | |
|---|---|---|---|---|---|---|
| 3d conc. | 8 AM | Noon | 4 PM | 8 AM | Noon | 4 PM |
| 2.5 mM | −1.0 (±1.4)<br>p = 0.14 | −1.9 (±1.9)<br>p = 0.31 | −3.4 (±2.0)<br>p = 0.03 | −2.2 (±1.4)<br>p = 0.20 | −1.9 (±1.8)<br>p = 0.20 | −3.6 (±2.1)<br>p = 0.02 |
| 0.5 mM | −1.4 (±1.2)<br>p = 0.29 | −2.4 (±1.8)<br>p = 0.15 | −2.5 (±2.5)<br>p = 0.21 | −2.6 (±1.4)<br>p = 0.08 | −3.2 (±1.7)<br>p < 0.01 | −4.6 (±1.9)<br>p < 0.001 |
| Vehicle Control | −1.9 (±2.5) | −1.4 (±3.1) | −1.7 (±2.5) | −1.6 (±2.4) | −1.1 (±2.5) | −1.8 (±2.4) |

BID: twice daily;
GAT: Goldmann applanation tonometry;
IOP: intraocular pressure;
mM: millimolar;
mmHg: millimeters of Mercury;
QAM: once daily in the morning;
SD: standard deviation

TABLE 9

IOP (mmHg) Listing by Subject and Visit (iCARE) in Humans

| Subject | Treatment | | Screen | | | Day 1 | | | Day 7 | | | Day 14 | | |
|---|---|---|---|---|---|---|---|---|---|---|---|---|---|---|
| number | assignment | Eye | V1A/ | V1B/ | V1C/ | V2A/ | V2B/ | V2C/ | V3A/ | V3B/ | V3C/ | V4A/ | V4B/ | V4C/ |
| 1 | 2.5 mM | OD | 18.3 | 15.8 | 18.5 | 16 | 11.1 | 10.7 | 14.1 | 13.3 | 12.7 | 14.5 | 12.8 | 10.3 |
| | | OS | 14.7 | 16.6 | 19.7 | 14 | 10.4 | 10.4 | 12.7 | 11.2 | 10.2 | 14.5 | 12.6 | 13.5 |
| 2 | 0.5 mM | OD | 16 | 15 | 10 | 16.7 | 9.9 | 12 | 13.9 | 12.5 | 10.4 | 11.1 | 9.5 | 9 |
| | | OS | 16 | 15 | 14.7 | 17.2 | 9.7 | 14 | 15.3 | 13 | 11 | 11.1 | 10.7 | 9.2 |
| 3 | Vehicle | OD | 24.3 | 17 | 19.3 | 18.2 | 18.5 | 19 | 24.3 | 20.2 | 23.3 | 21.7 | 20.9 | 18.8 |
| | | OS | 27 | 19.6 | 18.4 | 20.6 | 19 | 18.4 | 24.4 | 22 | 20.5 | 25.5 | 20.5 | 21.2 |
| 4 | 2.5 mM | OD | 23.6 | 18.9 | 18.9 | 17.3 | 17.8 | 17.6 | 20.1 | 15.2 | 17.3 | 18.3 | 13.9 | 13.8 |
| | | OS | 18.5 | 17.1 | 18.3 | 17.8 | 17.7 | 17.5 | 20.1 | 15.7 | 16.3 | 14.9 | 13.9 | 13.4 |
| 5 | 0.5 mM | OD | 21.5 | 18 | 17 | 17.9 | 16.7 | 16.3 | 17.3 | 16 | 14.3 | 15.4 | 15.4 | 14.1 |
| | | OS | 19.5 | 16.2 | 18.1 | 18.4 | 15.7 | 16.7 | 16.5 | 13.3 | 13.9 | 12 | 14.5 | 12.5 |
| 6 | Vehicle | OD | 18.8 | 18.5 | 15.7 | 16.4 | 16.4 | 16.2 | 17.7 | 17.1 | 17.8 | 18.3 | 16.7 | 17.9 |
| | | OS | 19.1 | 17.3 | 15.4 | 16.5 | 16.7 | 14.1 | 17.9 | 16 | 14.8 | 15.4 | 15.2 | 16 |
| 7 | 2.5 mM | OD | 16.9 | 17.2 | 16.3 | 17.1 | 12.2 | 10 | 14.8 | 13.6 | 13.3 | 16 | 15.8 | 15.5 |
| | | OS | 17.3 | 15.1 | 20.1 | 17 | 14.5 | 13.3 | 16.3 | 14.3 | 12 | 17.4 | 16.9 | 15.5 |
| 8 | 0.5 mM | OD | 19.2 | 18.6 | 16.2 | 17.8 | 17.6 | 14.1 | 17.3 | 16.4 | 15.3 | 17.2 | 15.5 | 14.3 |
| | | OS | 17.6 | 17.9 | 16.7 | 17.1 | 14 | 13.5 | 17.1 | 15 | 14.1 | 15.1 | 14.1 | 13.7 |
| 9 | Vehicle | OD | 17 | 17.4 | 13.4 | 14.5 | 12.5 | 12.6 | 12.4 | 13 | 13.5 | 12.2 | 13 | 11.7 |
| | | OS | 20 | 18.4 | 13.6 | 13.6 | 12.8 | 14.3 | 12.7 | 12.1 | 12.2 | 10.4 | 12.3 | 13.9 |
| 10 | 2.5 mM | OD | 16.5 | 16 | 16.3 | 17.7 | 13.4 | 11 | 17.7 | 16.2 | 15.3 | 15.1 | 14.8 | 14.2 |
| | | OS | 17 | 16 | 16.7 | 17.3 | 15.5 | 12.3 | 17.1 | 16.2 | 16.3 | 16.7 | 14.2 | 15.4 |
| 11 | 0.5 mM | OD | 16.5 | 18.4 | 14.4 | 18.3 | 15.9 | 15 | 18.2 | 15.3 | 14.1 | 15.4 | 14.1 | 13.9 |
| | | OS | 18 | 16.8 | 15.9 | 17.9 | 16.4 | 16 | 18.5 | 17.2 | 14.6 | 14.7 | 14 | 13.6 |
| 12 | Vehicle | OD | 17.2 | 15.4 | 17.8 | 16.8 | 13 | 14.6 | 15.8 | 15.2 | 11.7 | 15 | 14 | 13 |
| | | OS | 14.2 | 12.2 | 14.4 | 16.1 | 12.9 | 13.3 | 13.5 | 13.1 | 10.2 | 14 | 13.4 | 12.3 |
| 13 | 2.5 mM | OD | 17 | 13.7 | 13.6 | 18.3 | 15.5 | 14.4 | 18.2 | 15.5 | 11.3 | 16.4 | 14.4 | 13.3 |
| | | OS | 17 | 16.6 | 16.3 | 17.3 | 15.3 | 16.3 | 16.6 | 13.6 | 12 | 16.8 | 15.9 | 12.7 |

TABLE 9-continued

IOP (mmHg) Listing by Subject and Visit (iCARE) in Humans

| Subject number | Treatment assignment | Eye | Screen V1A/ | Screen V1B/ | Screen V1C/ | Day 1 V2A/ | Day 1 V2B/ | Day 1 V2C/ | Day 7 V3A/ | Day 7 V3B/ | Day 7 V3C/ | Day 14 V4A/ | Day 14 V4B/ | Day 14 V4C/ |
|---|---|---|---|---|---|---|---|---|---|---|---|---|---|---|
| 14 | 0.5 mM | OD | 16.5 | 16.8 | 16 | 16.3 | 11.6 | 12.4 | 15.2 | 14.2 | 13.4 | 16.2 | 13.3 | 11.8 |
| | | OS | 14 | 14 | 15 | 17 | 15.6 | 12 | 13.6 | 13.1 | 12.4 | 13.4 | 11.3 | 9.5 |
| 15 | Vehicle | OD | 18 | 15.3 | 13.8 | 16.2 | 15.4 | 15.2 | 18 | 17 | 15.7 | 16.5 | 17.1 | 16.4 |
| | | OS | 16.3 | 19 | 16.6 | 17 | 15.3 | 14.5 | 19.3 | 17.1 | 17.2 | 18.3 | 15.7 | 15.9 |
| 16 | 2.5 mM | OD | 16.5 | 16.5 | 16.3 | 16.5 | 14.4 | 13.7 | 18.3 | 15.6 | 15.8 | 17.1 | 18.2 | 15.7 |
| | | OS | 18.2 | 18.6 | 19.7 | 16.3 | 15.4 | 13.3 | 16.7 | 18.7 | 17.8 | 17.4 | 18.7 | 16.9 |
| 17 | 0.5 mM | OD | 17 | 17.5 | 17.1 | 16.3 | 15.8 | 15.1 | 15.1 | 17.1 | 17.3 | 16.7 | 16.2 | 16 |
| | | OS | 17 | 17 | 16.8 | 17 | 15.5 | 15.5 | 16.5 | 17 | 17 | 17 | 14.9 | 15 |
| 18 | Vehicle | OD | 17.6 | 14.4 | 17.1 | 18.1 | 15.7 | 14 | 13.3 | 15.6 | 15.2 | 14.3 | 15.5 | 15.3 |
| | | OS | 14 | 16.5 | 16.2 | 16.6 | 16.6 | 14.1 | 14.7 | 14.6 | 15.4 | 15 | 13.7 | 16.3 |
| 19 | 2.5 mM | OD | 19.8 | 19 | 16 | 17.8 | 16.2 | 17.8 | 19.3 | 13.7 | 14.6 | 17.5 | 15.1 | 14.6 |
| | | OS | 18 | 17 | 15 | 17.5 | 15.2 | 17.5 | 15 | 15.1 | 13.8 | 17.3 | 15.2 | 13.8 |
| 20 | 0.5 mM | OD | 19.8 | 19.2 | 21.8 | 17.9 | 13.4 | 15 | 19 | 14 | 13.6 | 16 | 15.7 | 15.6 |
| | | OS | 17.1 | 20 | 21.3 | 16.5 | 15.2 | 14.9 | 16.5 | 13.1 | 13.2 | 14 | 15 | 14.4 |
| 21 | Vehicle | OD | 17.5 | 17 | 18.3 | 16.7 | 16.7 | 15 | 14.1 | 12.8 | 15.2 | 15 | 14.5 | 12.6 |
| | | OS | 19.6 | 19.6 | 19.6 | 17.8 | 16.1 | 14 | 15.1 | 12.8 | 13.3 | 14.8 | 15.7 | 13.8 |

A: approximately 8 AM timepoint;
B: approximately noon timepoint (4 hours after A);
C: approximately 4 PM timepoint (8 hours after A);
IOP: intraocular pressure;
mM: millimolar;
mmHg: millimeters of Mercury;
OD: right eye;
OS: left eye;
V: visit No ocular or systemic AEs occurred. Mild transient hyperemia was seen sporadically in the 2.5 mM group, and not felt to be an AE. This occurred following the morning dosing during the study visits in 4 of 7 subjects in the 2.5 mM cohort. No changes on slit lamp exam were observed in the 0.5 mM formulation 3d or vehicle cohorts. The 2.5 mM treatment group demonstrated significantly lower IOP at the 4 PM timepoint on Day 7 (QAM dosing regimen) and on Day 14 (BID dosing regimen) while 0.5 mM appeared significant at Noon and at 4 PM on Day 14 (BID dosing regimen) compared to vehicle control. Both concentrations (2.5 mM and 0.5 mM) have an IOP lowering effect throughout the 7-day and 14-day treatment period.

Example 10 Five-Day Tolerability Study of Formulation 3d by Ocular Topical Instillation in Rabbits Toxicokinetic characteristics of formulation 3d was evaluated in Dutch Belted (DB) rabbits. The effect of formulation 3d on ocular safety and systemic PK following BID bilateral dosing was evaluated in DB rabbits treated with two doses, 0.02 mg/eye/dose and 0.06 mg/eye/dose.

Dosing

Formulation 3d was administered in rabbits through topical ophthalmic (T.O.) instillation oculus uterque (OU, both eyes) twice a day (BID) for 5 consecutive days. Two doses (0.05% [0.02 mg/eye/dose; 0.04 mg/eye/day] and 0.15% [0.06 mg/eye/dose; 0.12 mg/eye/day]) of formulation 3d via T.O. for 5 consecutive days.

Observations

Both doses were well tolerated in rabbits with no drug related adverse events. There was no mortality, no formulation 3d-related clinical signs or changes in body weight or food consumption, and no ocular changes considered to be test item-related as evaluated by gross ocular examination, ophthalmology, or tonometry. No macroscopic findings were present in the tissues examined.

Results

Peak plasma exposures in the study were low with measured concentrations at 3.29 ng/mL or less (lower limit of quantitation=0.5 ng/mL), and no quantifiable values for samples collected later than 4 hours post-dose. In male rabbits, observed $AUC_{tlast}$ and the maximum plasma concentration ($C_{max}$) values increased in a less-than-dose-proportional manner with increasing dose administered, while in females $C_{max}$ and $AUC_{tlast}$ were similar in both dose groups. AUC and AUC/Dose values were slightly higher on Day 5 as compared to Day 1 although due to high variability, the dose accumulation over 5 days seem unlikely (Table).

TABLE 10

Summary of TK Parameters of Levcromakalim in Plasma following T.O. Administrations of Formulation 3d in Rabbits

| Group (Dose [mg/eye/dose]) | Day | $T_{max}$ (h) | $C_{max}$ (ng/mL) | $C_{max}$/Dose (ng/mL/mg) | $AUC_{tlast}$ (h*ng/mL) | $AUC_{tlast}$/Dose (h*ng/mL/mg) | $t_{last}$ | $t_{1/2}$ |
|---|---|---|---|---|---|---|---|---|
| Males | | | | | | | | |
| 1 (0.02) | 1 | 1.00 ± 0.87 | 1.25 ± 0.32 | 31.17 ± 7.97 | 1.62 ± 0.74 | 40.52 ± 18.50 | 2.00 ± 1.00 | 0.91 ± NR |
| | 5 | 0.83 ± 0.29 | 1.24 ± 0.25 | 31.08 ± 6.20 | 2.09 ± 0.46 | 52.15 ± 11.48 | 2.33 ± 0.58 | 1.33 ± NR |

TABLE 10-continued

Summary of TK Parameters of Levcromakalim in Plasma following T.O. Administrations of Formulation 3d in Rabbits

| Group (Dose [mg/eye/dose]) | Day | $T_{max}$ (h) | $C_{max}$ (ng/mL) | $C_{max}$/Dose (ng/mL/mg) | $AUC_{tlast}$ (h*ng/mL) | $AUC_{tlast}$/Dose (h*ng/mL/mg) | $t_{last}$ | $t_{1/2}$ |
|---|---|---|---|---|---|---|---|---|
| 2 (0.06) | 1 | 0.67 ± 0.29 | 2.44 ± 0.70 | 20.36 ± 5.84 | 4.74 ± 2.99 | 39.49 ± 24.89 | 3.00 ± 1.00 | 1.36 ± 0.37 |
| | 5 | 0.67 ± 0.29 | 2.37 ± 0.80 | 19.78 ± 6.65 | 5.67 ± 3.09 | 47.24 ± 25.78 | 3.33 ± 1.15 | 1.44 ± 0.15 |
| Females | | | | | | | | |
| 1 (0.02) | 1 | 1.50 ± 0.87 | 0.95 ± 0.19 | 23.67 ± 4.69 | 1.77 ± 0.71 | 44.27 ± 17.82 | 3.00 ± 0.00 | NR |
| | 5 | 1.17 ± 0.76 | 1.17 ± 0.13 | 29.25 ± 3.19 | 2.75 ± 0.70 | 68.63 ± 17.44 | 3.33 ± 0.58 | 3.00 ± NR |
| 2 (0.06) | 1 | 1.00 ± 0.87 | 0.84 ± 0.29 | 7.00 ± 2.43 | 1.31 ± 1.72 | 10.90 ± 14.35 | 1.83 ± 1.89 | 1.84 ± NR |
| | 5 | 0.50 ± 0.00 | 1.28 ± 0.35 | 10.67 ± 2.88 | 2.70 ± 1.36 | 22.51 ± 11.35 | 3.00 ± 1.00 | 1.68 ± NR |

$AUC_{tlast}$ = area under the drug concentration-time curve to the last measurable concentration;
$C_{max}$ = maximum plasma concentration;
h = hour;
mg = milligram;
mL = milliliter;
ng = nanogram;
NR = Not reported;
$t_{1/2}$ = half-life;
TK = toxicokinetic;
$t_{last}$ = time of last measured drug concentration;
$T_{max}$ = time to peak drug concentration;
T.O. = topical ophthalmic
Daily doses were 0.02 and 0.06 mg/eye/dose or 0.04 and 0.12 mg/eye/day, for Groups 1 and 2, respectively.

Both doses of formulation 3d (0.05% [1.7 mM], 0.02 mg/eye/dose [Group 1] and 0.15% [5 mM], 0.06 mg/eye/dose [Group 2]) were well tolerated in rabbits with no significant changes observed upon ophthalmic and gross ocular examination during the 5-day dosing period. Levcromakalim was only detected up to 4 hours post-dose in plasma for both concentrations (1.7 mM and 5 mM). Area under the drug concentration-time curve (AUC) and AUC/Dose values were slightly higher on Day 5 as compared to Day 1; however, the high variability made it difficult to make any definitive conclusions on accumulation over the 5 days of dosing.

This study demonstrates the ability of formulation 3d topical solution to deliver the active pharmaceutical ingredient (API), levcromakalim, measurably into the body in rabbits. No significant ocular or systemic AEs such as hyperemia (eye redness) was observed in this study.

Example 11 Evaluation of Tolerability, Safety, and Pharmacokinetics of Formulation 3d Through a 15-day Non-GLP Study in the Dutch Belted Rabbits Effect of formulation 3d on ocular safety, tolerability and systemic PK following 14 day QD dosing was evaluated in DB rabbits treated with levcromakalim formulation 3d dosed at 0 mM (formulation buffer), 0.05 mM (0.0015%), 0.5 mM (0.015%), and 5 mM (0.15%).

Method

Rabbits received once daily topical doses of formulation 3d at 0 mM (formulation buffer), [0.0015% (0.05 mM, 0.0006 mg/eye/dose), 0.015% (0.5 mM, 0.006 mg/eye/dose), 0.15% (5 mM, 0.06 mg/eye/dose)] in the left eyes, while the right eyes received formulation buffer.

Ocular-related safety endpoints included ocular examinations (baseline, Days 3, 7, 10, and 14), tonometry (BID for 5 days before the onset of dosing, and 4- and 23-hours post-dose for the duration of the study, with the exception of weekend days and Day 15), and histopathology. In the high dose animals, plasma was collected from 3 animals each at 30 minutes and 1, 2, 4-, 6-, 8-, and 23-hours post-dose on Days 1 and 15. Animals were euthanized on Day 15 and the left eyes (n=2 eyes/group) were collected from all treated groups and processed for ocular tissue PK analysis.

Observations

IOPs remained within the normal range for this strain and species at all timepoints pre- and post-dosing. No other signs of histologic abnormalities were observed. Ocular examination scores were '0' in all animals at all timepoints, indicating a lack of inflammation. Ophthalmic examinations on various days during treatment showed no signs of any adverse events (AEs) (0 score on all animals and timepoints), except for two instances of incidental conjunctival inflammation (one control and one treated with the lowest dose).

Results

Results of the bioanalysis indicated low levels of leveromakalim were detected at the 30-minute, 1-hour, 2-hour, and 4-hour timepoints following a single dose of formulation 3d (high dose, 5 mM). After 4 hours, no levcromakalim was detected in plasma. Plasma levels of levcromakalim on Day 15 following 14 days of once daily dosing were similar to Day 1 with levcromakalim being detectable at low plasma levels out to 4 hours post dose and no accumulation. There was an exception at the 2-hour timepoint for one animal, which showed a concentration of 991.60 ng/mL. This appears to be an anomaly as concentrations of levcromakalim from the other timepoints for this animal and all other animals were in the normal range. The cause of this high reading is unknown.

Formulation 3d treatment resulted in low levels of levcromkalim systemically. In ocular tissues, levcromakalim could be detected up to 4 hours post dose without evidence of accumulation. In ocular tissues, low levels of levcromakalim were detected in aqueous humor (AH) (0.88-1.78 ng/mL), iris ciliary-body (ICB) (0.75-0.92 ng/mL), retina (0.69 ng/mL) and retinal pigment epithelium (RPE)/choroid (0.50-6.63 ng/mL) up to 4 hours post-dose on Day 15. Overall, formulation 3d was well tolerated without AEs, when dosed at three different concentrations QD.

This study demonstrates that formulation 3d, has a surprisingly benign toxicology profile with no notable adverse events up to its maximally formulatable concentration (5 mM) in rabbits. No significant ocular or systemic AEs such as hyperemia (eye redness) was observed in this study.

Example 12 a 28 Day Repeated Dose Toxicology Study by Ocular Topical Administration of Formulation 3d in Dutch Belted Rabbits Plasma concentrations of levcromakalim were evaluated in DB rabbits after twice a day (BID) oculus uterque (OU, both eyes) topical ophthalmic (T.O.) administration of formulation 3d for 28 days at dose levels of 0, 0.012, 0.03, and 0.06 mg/eye/dose.

Method

Plasma concentrations of levcromakalim were evaluated in DB rabbits after BID OU T.O. administration of three concentrations of formulation 3d at dose levels of 0, 0.012, 0.03, and 0.06 mg/eye/dose (0, 0.024, 0.06, and 0.12 mg/eye/day respectively or 0.030% [1.0 mM], 0.075% [2.5 mM], or 0.15% [5 mM] respectively) for 28 days. Plasma was collected from 3 animals/dose group at pre-dose, 0.5, 1, 2, 3, 4, 6, and 12 hours post-first dose on Days 1 and 28.

Observations

Formulation 3d was well-tolerated in rabbits at levels of 0.012, 0.03 and 0.06 mg/eye/dose (0.024, 0.06 and 0.12 mg/eye/day), respectively, with no adverse changes observed during the 28-day dosing period or after a 2-week recovery period. No findings were observed for any endpoint, including clinical observations, body weights, food consumption, ophthalmology, ERG, tonometry, clinical pathology, macroscopic and/or microscopic evaluation, and histopathology of a comprehensive list of systemic tissues.

Results

Peak plasma exposures were low with measured concentrations at 4.942 ng/mL or less (lower limit of quantitation=0.500 ng/mL), and no quantifiable values for samples collected later than 6 hours post-dose (Table). Generally, $AUC_{tlast}$ and $C_{max}$ increased with increasing dose level, but in a less than dose-proportional manner. High variability in the study made it difficult to conclude whether any differences are seen in AUC and $C_{max}$ values between females and males. $AUC_{tlast}$ and $C_{max}$ values were slightly lower on Day 28 as compared to Day 1, except for males in Group 4 ($R_{AUC}$=1.083, $R_{Cmax}$=0.986); indicating no observed systemic levcromakalim accumulation over the 28 days of BID T.O. formulation 3d dosing.

TABLE 11

Summary of Toxicokinetic (TK) Parameters of levcromakalim in Plasma following BID T.O. Bilateral Administrations of formulation 3d for 28 Days in Rabbits

| Dose (mg/eye/dose) | Day | $T_{max}$ (h) | $C_{max}$ (ng/mL) | $C_{max}$/Dose (ng/mL/mg) | $AUC_{tlast}$ (h*ng/mL) | $AUC_{tlast}$/Dose (h*ng/mL/mg) | $t_{last}$ | $t_{1/2}$ |
|---|---|---|---|---|---|---|---|---|
| Males | | | | | | | | |
| 0.012 | 1 | 1.17 ± 0.76 | 0.77 ± 0.31 | 32.12 ± 12.98 | 0.94 ± 0.75 | 39.23 ± 31.19 | 1.50 ± 0.87 | NR |
| | 28 | 0.33 ± 0.29 | 0.37 ± 0.32 | 15.40 ± 13.37 | 0.14 ± 0.008 | 5.78 ± 0.35 | 0.500 ± NC | NR |
| 0.03 | 1 | 0.67 ± 0.29 | 2.26 ± 0.46 | 28.88 ± 7.62 | 3.96 ± 1.22 | 66.06 ± 20.41 | 3.00 ± 1.00 | 1.28 ± 0.33 |
| | 28 | 0.50 ± NC | 1.68 ± 0.29 | 28.05 ± 4.76 | 2.53 ± 1.20 | 42.11 ± 20.08 | 2.33 ± 1.15 | 2.88 ± 1.89 |
| 0.06 | 1 | 0.70 ± 0.27 | 2.61 ± 1.02 | 21.78 ± 8.48 | 5.64 ± 2.04 | 47.04 ± 17.04 | 3.60 ± 0.55 | 1.72 ± 0.30 |
| | 28 | 0.60 ± 0.22 | 2.58 ± 0.84 | 21.48 ± 7.02 | 6.11 ± 3.53 | 50.96 ± 29.44 | 4.20 ± 1.09 | 2.29 ± 0.53 |
| Females | | | | | | | | |
| 0.012 | 1 | 1.67± 0.58 | 0.64 ± 0.08 | 26.67 ± 3.25 | 0.57 ± 0.47 | 23.74 ± 19.58 | 2.00 ± NC | 1.84 ± NC |
| | 28 | 0.33 ± 0.29 | 0.56 ± 0.48 | 23.21 ± 20.10 | 0.051 ± 0.42 | 21.11 ± 17.54 | 2.25 ± 2.47 | NR |
| 0.03 | 1 | 0.67 ± 0.29 | 1.75 ± 1.12 | 29.22 ± 18.60 | 3.99 ± 2.10 | 66.44 ± 35.00 | 3.67 ± 0.58 | 1.70 ± 0.94 |
| | 28 | 0.67 ± 0.29 | 1.76 ± 0.15 | 29.41 ± 2.44 | 3.58 ± 0.79 | 59.64 ± 13.25 | 3.33 ± 0.58 | 2.19 ± 0.61 |

TABLE 11-continued

Summary of Toxicokinetic (TK) Parameters of levcromakalim in Plasma following BID T.O. Bilateral Administrations of formulation 3d for 28 Days in Rabbits

| Dose (mg/eye/dose) | Day | $T_{max}$ (h) | $C_{max}$ (ng/mL) | $C_{max}$/Dose (ng/mL/mg) | $AUC_{tlast}$ (h*ng/mL) | $AUC_{tlast}$/Dose (h*ng/mL/mg) | $t_{last}$ | $t_{1/2}$ |
|---|---|---|---|---|---|---|---|---|
| 0.06 | 1 | 1.00 ± 0.00 | 2.85 ± 1.31 | 23.73 ± 10.94 | 8.89 ± 4.14 | 74.06 ± 34.54 | 4.80 ± 1.09 | 1.77 ± 0.26 |
| | 28 | 1.20 ± 0.76 | 2.06 ± 0.29 | 17.13 ± 2.40 | 6.05 ± 1.81 | 50.39 ± 15.06 | 4.80 ± 1.09 | 1.97 ± 0.74 |

$AUC_{tlast}$ = area under the drug concentration-time curve to the last measurable concentration;
$C_{max}$ = maximum plasma concentration;
h = hour;
mg = milligram;
mL = milliliter;
ng = nanogram;
NR = Not reported;
$t_{1/2}$ = half-life;
TK = toxicokinetic;
$t_{last}$ = time of last measured drug concentration;
$T_{max}$ = time to peak drug concentration;
T.O. = topical ophthalmic
Daily doses were 0.03, 0.012 and 0.06 mg/eye/dose, or 0.06, 0.024, and 0.12 mg/eye/day, for Groups 2, 3, and 4, respectively.

The no observed adverse effect level (NOAEL) was determined to be 0.06 mg/eye/dose (0.12 mg/eye/day). It may be noted that this top dose 0.12 mg/eye/day, was also the maximum feasible dose based on dose volume and solubility considerations. At the NOAEL, the mean $C_{max}$ and AUC values for males were 2.58 ng/mL and 6.11 h*ng/mL, respectively, and for females were 2.06 ng/mL and 6.05 h*ng/mL, respectively, after 28 days of dosing. Similar to previous studies, plasma exposure levels of levcromakalim were low, only quantifiable through 6 hours post-dose, and demonstrated no accumulation over 28 days of formulation 3d dosing.

This study demonstrates that this novel formulation, formulation 3d, has a surprisingly benign toxicology profile with no notable adverse events up to its maximally formulatable concentration (5 mM) in rabbits. No significant ocular or systemic AEs such as hyperemia (eye redness) was observed in this study.

Example 13 Exemplary Topical Ocular Composition of Levcromakalim for Humans

Levcromakalim ophthalmic solution for topical administration was manufactured under cGMP conditions in strengths of 0.015%, 0.030%, and 0.075% containing 0.0 mg/mL, 0.15 mg/mL, 0.30 mg/mL, and 0.75 mg/mL of levcromakalim respectively.

The levcromakalim ophthalmic solution was filled into a low-density polyethylene blow fill seal (BFS) single use unit dose container. A description of the formulations is provided in Table 12.

TABLE 12

Description of Levcromakalim Ophthalmic Solution, 0.0%, 0.015%, 0.030%, and 0.075%

| Strength (Concentration and Unit Dose) | Description |
|---|---|
| 0.0% (0 mg/mL) BFS unit dose (Vehicle Control) | A clear, colorless 300 μL unit dose BFS of levcromakalim ophthalmic solution at a concentration at a concentration of 0.0% (0.0 mg/mL) in an iso-osmotic phosphate buffered solution at pH 6.5 |
| 0.015% (0.15 mg/mL) (0.4 mM) BFS unit dose | A clear, colorless 300 μL unit dose BFS of levcromakalim ophthalmic solution at a concentration of 0.015% (0.15 mg/mL) in an iso-osmotic phosphate buffered solution at pH 6.5 |
| 0.030% (0.30 mg/mL) (0.8 mM) BFS unit dose | A clear, colorless 300 μL unit dose BFS of levcromakalim ophthalmic solution at a concentration of 0.030% (0.30 mg/mL) in an iso-osmotic phosphate buffered solution at pH 6.5 |
| 0.075% (0.75 mg/mL) (2.1 mM) BFS unit dose | A clear, colorless 300 μL unit dose BFS of levcromakalim ophthalmic solution at a concentration of 0.075% (0.75 mg/mL) in an iso-osmotic phosphate buffered solution at pH 6.5 |

The composition of formulation 3d ophthalmic solution at 0.0% (vehicle control), 0.015%, 0.030%, and 0.075% strengths is presented in Table 13. A unit dose consists of 310 mg of formulation 3d ophthalmic solution in a BFS container closure system. For human application, a dose consists of a single drop of approximately 30 L administrated topically is intended for each eye.

TABLE 13

Levcromakalim Ophthalmic Solution: Unit Dose Composition

| | 0.0% Levcromakalim Ophthalmic Solution, 300 µL | | 0.015% Levcromakalim Ophthalmic Solution, 300 µL | | 0.030% Levcromakalim Ophthalmic Solution, 300 µL | | 0.075% Levcromakalim Ophthalmic Solution, 300 µL | | | |
|---|---|---|---|---|---|---|---|---|---|---|
| | mg per unit dose | % w/v | mg per unit dose | % w/v | mg per unit dose | % w/v | mg per unit dose | % w/v | Pharmaceutical Function | Quality Standards |
| Levcromakalim | 0.0 mg | 0.0% | 0.045 mg | 0.015% | 0.090 mg | 0.030% | 0.225 mg | 0.075% | API | Module 3.2.S, levcromakalim |
| Kolliphor ELP | 12 mg | 4.0% | 12 mg | 4.0% | 12 mg | 4.0% | 12 mg | 4.0% | Solubilizer | USP [a] |
| Polysorbate 80 | 3 mg | 1.0% | 3 mg | 1.0% | 3 mg | 1.0% | 3 mg | 1.0% | Solubilizer | NF |
| Povidone (PVP) K30 | 6 mg | 2.0% | 6 mg | 2.0% | 6 mg | 2.0% | 6 mg | 2.0% | Solubilizer | USP |
| Poloxamer 407 | 0.3 mg | 0.10% | 0.3 mg | 0.10% | 0.3 mg | 0.10% | 0.3 mg | 0.10% | Solubilizer | BP, EP, JP, NF |
| Mannitol | 9.9 mg | 3.3% | 9.9 mg | 3.3% | 9.9 mg | 3.3% | 9.9 mg | 3.3% | Osmotic modifier | BP, EP, JP, USP |
| Sodium Phosphate Dibasic Heptahydrate | 0.287 mg | 0.0958% | 0.287 mg | 0.0958% | 0.287 mg | 0.0958% | 0.287 mg | 0.0958% | pH Buffering Agent | USP |
| Sodium Phosphate Monobasic Monohydrate | 0.266 mg | 0.0887% | 0.266 mg | 0.0887% | 0.266 mg | 0.0887% | 0.266 mg | 0.0887% | pH Buffering Agent | BP, USP |
| 1N HCl | N/A | QS to pH 6.5 | N/A | QS to pH 6.5 | N/A | QS to pH 6.5 | N/A | QS to pH 6.5 | pH adjustment if needed | USP/NF |
| Water for Injection | QS to 300 µL | QS to 100% | QS to 300 µL | QS to 100% | QS to 300 µL | QS to 100% | QS to 300 µL | QS to 100% | Carrier | WFI |

API = Active Pharmaceutical Ingredient;
BP = British Pharmacopeia;
EP = European Pharmacopoeia;
JP = Japanese Pharmacopeia;
N/A: Not Applicable;
NF = National Formulary;
QS = Quantity Sufficient;
USP = United States Pharmacopeia;
WFI = Water for injection
[a] Kolliphor ELP meets the USP/NF requirements for polyoxyl 35 castor oil The specific gravity of the formulations was measured during formulation development and converted to density. The density of the formulations was 1.02 g/mL.

Formulation components in the levcromakalim ophthalmic solution 0.0%0 (vehicle control), 0.015%, 0.030%, and 0.075% strengths are presented in Table 14.

TABLE 14

Levcromakalim Ophthalmic Formulation Components

| Formulation components | Levcromakalim Ophthalmic Solution 0.0% (vehicle control), 0.015%, 0.030%, and 0.075% (% w/v) | Maximum Level[a] listed in the FDA Inactive Ingredient Database (IID) for Approved Drug Products/ for "Ophthalmic/ Solution, Drops" Route of Administration |
|---|---|---|
| Kolliphor ELP[b] | 4.0% | 5.0% w/v 6D4M1DAL6O[b] |
| Polysorbate 80 | 1.0% | 1.0% w/v UNII: 6OZP39ZG8H |
| Povidone (PVP) K-30 | 2.0% | 2.0% w/v UNII: U725QWY32X |
| Poloxamer 407 | 0.10% | 0.1% w/v UNII: TUF2IVW3M2 |
| Mannitol | 3.3% | 4.6% w/v UNII: 3OWL53L36A |
| Sodium Phosphate Dibasic Heptahydrate | 0.0958% | 2.5% w/v UNII: 70WT22SF4B |
| Sodium Phosphate Monobasic Monohydrate | 0.0887% | 1.3% w/v UNII: 593YOG76RN |

[a]FDA's electronic Inactive Ingredient Database for approved drug products (database last updated Jan. 21, 2021)
[b]Listing for USP polyoxyl 35 castor oil All of the excipients used in leveromakalim ophthalmic solution formulations are within the limits for the topical ophthalmic (drops) route of administration.

This specification has been described with reference to embodiments of the invention. However, one of ordinary skill in the art appreciates that various modifications and changes can be made without departing from the scope of the invention as set forth herein. Accordingly, the specification is to be regarded in an illustrative rather than a restrictive sense, and all such modifications are intended to be included within the scope of invention.

We claim:

1. A method of treating an ocular-related neurodegenerative disease affecting the posterior segment of the eye comprising administering an effective amount of an aqueous clear ocular topical pharmaceutical solution to a human in need thereof, wherein the pharmaceutical solution comprises an acceptable amount for ophthalmic topical administration of:

(a) levcromakalim at a concentration between about 0.05 mM to about 5 mM;
(b) an ethoxylated glycerol ester;
(c) a polyethoxylated furanose fatty acid ester;
(d) a polymeric lactam;
(e) a nonionic tri-block copolymer of a central hydrophobic chain of polyoxypropylene flanked by two hydrophilic chains of polyoxyethylene;
(f) a polyol; and
(g) water and phosphate buffer as aqueous components;

wherein the pH of the pharmaceutical solution is between 6 to 8.

2. The method of claim 1, wherein the ocular-related neurodegenerative disease is ischemia.

3. The method of claim 1, wherein the ocular-related neurodegenerative disease is non-arteritic anterior ischemic optic neuropathy (NAION).

4. The method of claim 1, wherein the ocular-related neurodegenerative disease is retinal ischemia.

5. The method of claim 1, wherein the ocular-related neurodegenerative disease is age-related macular degeneration.

6. The method of claim 5, wherein the age-related macular degeneration is wet age-related macular degeneration.

7. The method of claim 5, wherein the age-related macular degeneration is dry age-related macular degeneration.

8. The method of claim 1, wherein the ocular-related neurodegenerative disease is optic nerve drusen.

9. The method of claim 1, wherein the ocular-related neurodegenerative disease is an inherited optic neuropathy.

10. The method of claim 9, wherein the inherited optic neuropathy is selected from the group consisting of Leber's hereditary optic neuropathy (LHON), dominant optic atrophy, Behr's syndrome, and Berk-Tabatznik syndrome.

11. The method of claim 1, wherein the concentration of levcromakalim is about 0.075% w/v.

12. The method of claim 1, wherein the concentration of levcromakalim is about 0.03% w/v.

13. The method of claim 1, wherein the concentration of levcromakalim is about 0.015% w/v.

14. The method of claim 1, wherein the ethoxylated glycerol ester is a polyoxyl-ethylated castor oil.

15. The method of claim 14, wherein the polyoxyl-ethylated castor oil is at a concentration of up to about 5% w/v.

16. The method of claim 1, wherein the polymeric lactam is polyvinylpyrrolidone (PVP).

17. The method of claim 1, wherein the polyol is mannitol.

18. The method of claim 1, wherein the pharmaceutical solution further comprises a pH adjusting agent, which is hydrochloric acid.

19. The method of claim 1, wherein the pH of the pharmaceutical solution is about 6.5.

20. A method of treating diabetic retinopathy comprising administering an effective amount of an aqueous clear ocular topical pharmaceutical solution to a human in need thereof, wherein the pharmaceutical solution comprises an acceptable amount for ophthalmic topical administration of:

(a) levcromakalim at a concentration between about 0.05 mM to about 5 mM;
(b) an ethoxylated glycerol ester;
(c) a polyethoxylated furanose fatty acid ester;
(d) a polymeric lactam;
(e) a nonionic tri-block copolymer of a central hydrophobic chain of polyoxypropylene flanked by two hydrophilic chains of polyoxyethylene;
(f) a polyol; and
(g) water and phosphate buffer as aqueous components;

wherein the pH of the pharmaceutical solution is between 6 to 8.

21. The method of claim 20, wherein the concentration of levcromakalim is about 0.075% w/v.

22. The method of claim 20, wherein the concentration of levcromakalim is about 0.03% w/v.

23. The method of claim 20, wherein the concentration of levcromakalim is about 0.015% w/v.

24. The method of claim 20, wherein the ethoxylated glycerol ester is a polyoxyl-ethylated castor oil.

25. The method of claim 24, wherein the polyoxyl-ethylated castor oil is at a concentration of up to about 5% w/v.

26. The method of claim 20, wherein the polymeric lactam is polyvinylpyrrolidone (PVP).

27. The method of claim 20, wherein the polyol is mannitol.

28. The method of claim 20, wherein the pharmaceutical solution further comprises a pH adjusting agent, which is hydrochloric acid.

29. The method of claim 20, wherein the pH of the pharmaceutical solution is about 6.5.

* * * * *